United States Patent
Fujino et al.

(10) Patent No.: US 9,753,040 B2
(45) Date of Patent: Sep. 5, 2017

(54) POLYNUCLEOTIDE CONSTRUCT CAPABLE OF DISPLAYING FAB IN A CELL-FREE TRANSLATION SYSTEM, AND METHOD FOR MANUFACTURING AND SCREENING FAB USING SAME

(75) Inventors: Yasuhiro Fujino, Osaka (JP); Risako Fujita, Osaka (JP); Kouichi Wada, Osaka (JP); Kotomi Oda, Osaka (JP); Takuya Ueda, Tokyo (JP); Yoshihiro Shimizu, Tokyo (JP); Takashi Kanamori, Tokyo (JP)

(73) Assignees: Mitsubishi Tanabe Pharma Corporation, Osaka (JP); The University of Tokyo, Tokyo (JP)

( * ) Notice: Subject to any disclaimer, the term of this patent is extended or adjusted under 35 U.S.C. 154(b) by 950 days.

(21) Appl. No.: 13/990,654

(22) PCT Filed: Nov. 30, 2011

(86) PCT No.: PCT/JP2011/077725
§ 371 (c)(1),
(2), (4) Date: Jul. 11, 2013

(87) PCT Pub. No.: WO2012/074029
PCT Pub. Date: Jun. 7, 2012

(65) Prior Publication Data
US 2013/0288908 A1 Oct. 31, 2013

(30) Foreign Application Priority Data
Dec. 1, 2010 (JP) .................. 2010-268763

(51) Int. Cl.
*G01N 33/68* (2006.01)
*C12N 15/10* (2006.01)
*C07K 16/46* (2006.01)

(52) U.S. Cl.
CPC ....... *G01N 33/6854* (2013.01); *C07K 16/468* (2013.01); *C12N 15/1041* (2013.01);
(Continued)

(58) Field of Classification Search
CPC ........... G01N 33/6854; G01N 33/6857; C12N 15/1062; C12N 15/1041; C12N 15/1075;
(Continued)

(56) References Cited

U.S. PATENT DOCUMENTS

2005/0119455 A1 6/2005 Fuh et al.
2005/0136428 A1 6/2005 Crea

FOREIGN PATENT DOCUMENTS

JP 2005-535301 A 11/2005
JP 2008-271903 A 11/2008
(Continued)

OTHER PUBLICATIONS

Fowler et al., "High-resolution mapping of protein sequence-function relationships," *Nature Methods*, 7(9): 741-746 (2010).
(Continued)

*Primary Examiner* — Jeremy C Flinders
(74) *Attorney, Agent, or Firm* — Leydig, Voit & Mayer, Ltd.

(57) ABSTRACT

The polynucleotide construct of (1) or (2) below is used to perform ribosome display, CIS display and/or mRNA display in order to screen a Fab against an antigen of interest: (1) a polynucleotide construct which monocistronically comprises a ribosome-binding sequence, Fab first chain-coding sequence, linker peptide-coding sequence, Fab second chain-coding sequence and scaffold-coding sequence in this order, and further comprises at its 3'-end a structure necessary for maintaining a complex with the Fab encoded by itself; and (2) a polynucleotide construct which comprises a Fab first chain-expressing cistron and a Fab second
(Continued)

chain-expressing cistron each containing a ribosome-binding sequence, a Fab first chain-coding sequence or Fab second chain-coding sequence, and a scaffold-coding sequence in this order, the first Fab-expressing cistron further comprising at its 3'-end a ribosome stall sequence, said Fab second chain-expressing cistron further comprising at its 3'-end a structure necessary for maintaining a complex with the Fab encoded by itself.

23 Claims, 22 Drawing Sheets

(52) U.S. Cl.
CPC ..... *C12N 15/1062* (2013.01); *C12N 15/1075* (2013.01); *G01N 33/6857* (2013.01); *C07K 2317/31* (2013.01); *C07K 2317/55* (2013.01)

(58) Field of Classification Search
CPC .............. C07K 16/468; C07K 2317/31; C07K 2317/55
See application file for complete search history.

(56) References Cited

FOREIGN PATENT DOCUMENTS

| JP | 2011-182794 A | 9/2011 |
|---|---|---|
| WO | WO 2008/104184 A2 | 9/2008 |

OTHER PUBLICATIONS

Hust et al., "Single chain Fab (scFab) fragment," *BMC Biotechnology*, 7: 14, doi 10.1186/1472-6750-7-14 (Mar. 8, 2007).

McCafferty et al., "Phage antibodies: filamentous phage displaying antibody variable domains," *Nature*, 348: 552-554 (1990).

Pal et al., "Comprehensive and Quantitative Mapping of Energy Landscapes for Protein-Protein Interactions by Rapid Combinatorial Scanning," *The Journal of Biological Chemistry*, 281(31): 22378-22385 (2006).

Smith et al., "Filamentous Fusion Phage: Novel Expression Vectors That Display Cloned Antigens on the Virion Surface," *Science*, 228: 1315-1317 (1985).

Sumida et al., "Bicistronic DNA display for in vitro selection of Fab fragments," *Nucleic Acids Research*, 37(22): e147, doi:10.1093|nar|gkp776 (Sep. 29, 2009).

Uemura et al., "Approach to the affinity maturation and the specificity conversion of antibody by the synthetic CDR library," *Journal of Japanese Biochemical Society, Shoroku CD*, 4T15P-6 (4P-727) (2009).

Whitehead et al., "Optimization of affinity, specificity and function of designed influenza inhibitors using deep sequencing," *Nature Biotechnology*, 30(6): 543-548 and supplementary information pp. 1-39 [doi:10.1038/nbt.2214] (2012).

Wodak, "Next-generation protein engineering targets influenza," *Nature Biotechnology*, 30(6): 502-504 (2012).

Xu et al., "Affinity and Cross-Reactivity Engineering of CTLA4-Ig to Modulate T Cell Costimulation," *The Journal of Immunology*, 189: 4470-4477 (2012).

Japanese Patent Office, International Search Report in International Patent Application No. PCT/JP2011/077725 (Mar. 6, 2012).

International Bureau of WIPO, International Preliminary Report on Patentability in Patent Application No. PCT/JP2011/077725 (Jun. 4, 2013).

Burtet et al., *J. Biochem.*, 142(6): 665-669 (2007).
Fallot et al., *Nucleic Acids Research*, 37(20): e134 (2009).
Garrard et al., *Gene*, 128(1): 103-109 (1993).
Shimizu et al., *FEBS Journal*, 273(18): 4133-4140 (2006).
European Patent Office, Extended European Search Report in European Patent Application No. 11845270.5 (Oct. 31, 2014).

| | CDR position | Parent amino acid | Beneficial amino acid | Mixed base codon | Base diversity | Protein diversity |
|---|---|---|---|---|---|---|
| 1 | L1-7 | S | T | WCT | 2 | 2 |
| 2 | L2-1 | A | G | GST | 2 | 2 |
| 3 | L3-2 | Y | A | KMT | 4 | 4 |
| 4 | L3-3 | I | RADES | RNM | 18 | 11 |
| 5 | H1-1 | T | R | ASA | 2 | 2 |
| 6 | H1-3 | E | G | GRG | 2 | 2 |
| 7 | H1-8 | G | SA | RST | 4 | 4 |
| 8 | H2-14 | W | LYV | KDS | 12 | 9 |
| 9 | H2-15 | G | T | RSC | 4 | 4 |
| 10 | H2-18 | T | VAS | RBY | 12 | 8 |
| 11 | H3-26M | L | | MTG | 2 | 2 |
| 12 | H3-27 | Y | G | KRC | 4 | 4 |

Theoretical diversity      $1.9 \times 10^7$    $4.9 \times 10^6$

International definition of mixed base codon
R=A/G, Y=C/T, M=A/C, K=G/T, S=C/G, W=A/T,
B=C/G/T, D=A/G/T, H=A/C/T, V=A/C/G,
N=A/C/G/T

Fig.27

① Preparation of fragments 1 to 7 by PCR

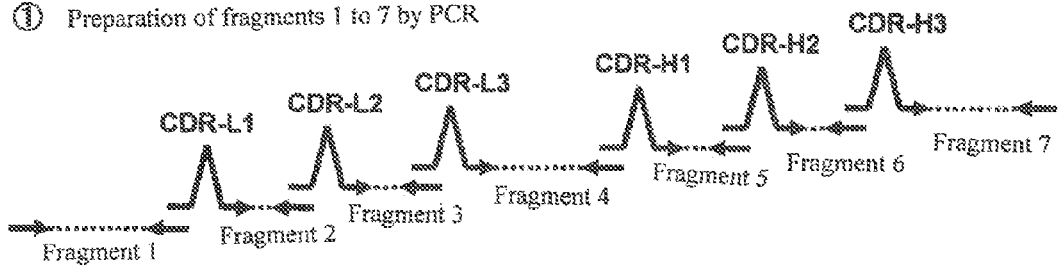

② Linking of fragments 1 to 7 by overlapping extension to produce the full-length DNA

③ Amplification of the Ymacs-secondary library by PCR

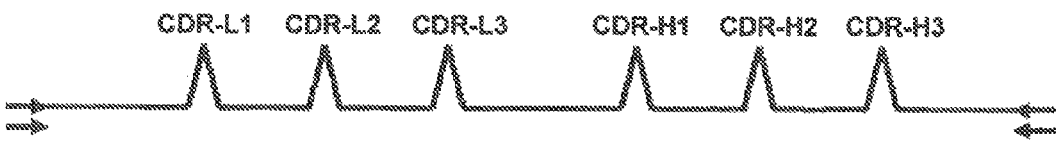

Fig.29

Fab-TT
kon = 3.14 x 10⁵
koff = 2.29 x 10⁻³
KD = 7.28 x 10⁻⁹

Ymacs #10
kon = 6.36 x 10⁵
koff < 1.00 x 10⁻⁵
KD < 1.57 x 10⁻¹¹

Fig.32
Ymacs #10
kon = 1.45 x 10$^6$
koff = 2.71 x 10$^{-5}$
KD = 1.87 x 10$^{-11}$
Ymacs #19
kon = 3.64 x 10$^6$
koff = 1.26 x 10$^{-5}$
KD = 3.45 x 10$^{-12}$
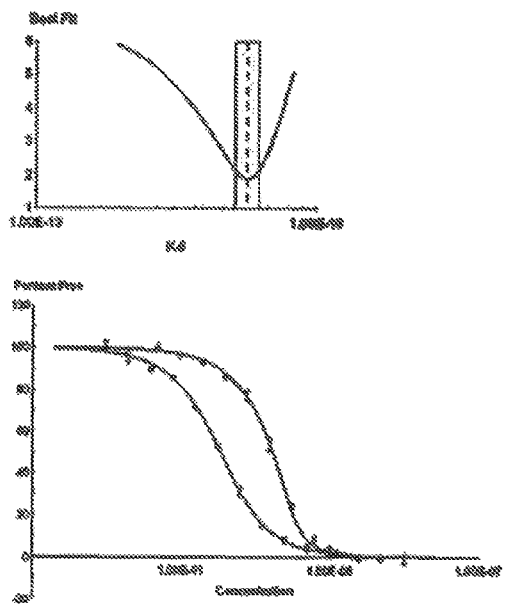
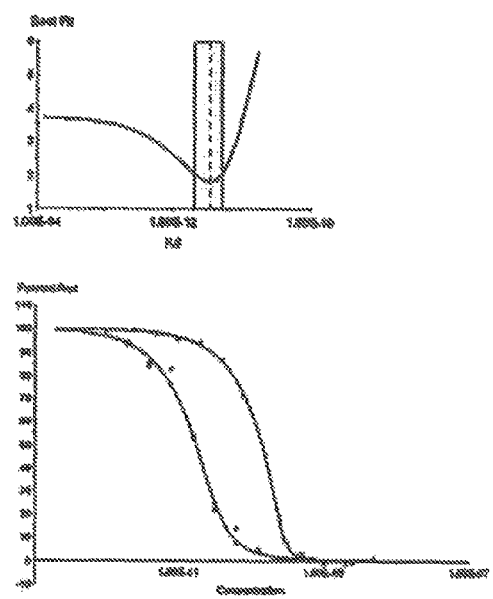

SEQUENCE LISTING

```
<160> NUMBER OF SEQ ID NOS: 73

<210> SEQ ID NO 1
<211> LENGTH: 1786
<212> TYPE: DNA
<213> ORGANISM: Artificial sequence
<220> FEATURE:
<223> OTHER INFORMATION: pTrc Fab-HH
<220> FEATURE:
<221> NAME/KEY: CDS
<222> LOCATION: (112)..(855)
<220> FEATURE:
<221> NAME/KEY: CDS
<222> LOCATION: (955)..(1767)

<400> SEQUENCE: 1
gctgttgaca attaatcatc cggctcgtat aatgtgtgga attgtgagcg gataacaatt      60
tcacacagga aacagaccta ggaattctaa ctttaagaag gagatatacc a atg aaa     117
                                                           Met Lys
                                                             1 tac ctg ctg ccg acc gtt gct gct ggt ctg ctc ctc gct gcc cag          165
Tyr Leu Leu Pro Thr Val Ala Ala Gly Leu Leu Leu Ala Ala Gln
        5                  10                   15 ccg gcg atg gcc atg gat atc cag atg acc cag tcc ccg agt tct cta      213
Pro Ala Met Ala Met Asp Ile Gln Met Thr Gln Ser Pro Ser Ser Leu
    20                  25                  30 tct gct tct gtg ggc gat agg gtc acc atc acc tgc cgt gcc agt cag      261
Ser Ala Ser Val Gly Asp Arg Val Thr Ile Thr Cys Arg Ala Ser Gln
35                  40                  45                  50 gat gtg aac acc gcc gtt gca tgg tat caa caa aaa cca gga aaa gcc      309
Asp Val Asn Thr Ala Val Ala Trp Tyr Gln Gln Lys Pro Gly Lys Ala
                55                  60                  65 ccg aag ctg ctg att tat agc gcc tct ttt ctg tat tct gga gtt cct      357
Pro Lys Leu Leu Ile Tyr Ser Ala Ser Phe Leu Tyr Ser Gly Val Pro
            70                  75                  80 tct cgc ttc tcc gga tcc cgt tct ggc act gat ttt act cta act att      405
Ser Arg Phe Ser Gly Ser Arg Ser Gly Thr Asp Phe Thr Leu Thr Ile
        85                  90                  95 agt agt cta cag ccg gag gac ttc gcc acc tat tat tgc caa caa cat      453
Ser Ser Leu Gln Pro Glu Asp Phe Ala Thr Tyr Tyr Cys Gln Gln His
    100                 105                 110 tac acc acc cct ccg act ttc ggc cag ggt acc aag gtg gaa att aaa      501
Tyr Thr Thr Pro Pro Thr Phe Gly Gln Gly Thr Lys Val Glu Ile Lys
115                 120                 125                 130 cgt act gtg gct gca cca tct gtc ttc atc ttc ccg cca tct gat gag      549
Arg Thr Val Ala Ala Pro Ser Val Phe Ile Phe Pro Pro Ser Asp Glu
                135                 140                 145 cag ttg aaa tct gga act gcc tct gtt gtg tgc ctg ctg aat aac ttc      597
Gln Leu Lys Ser Gly Thr Ala Ser Val Val Cys Leu Leu Asn Asn Phe
            150                 155                 160 tat ccc aga gag gcc aaa gta cag tgg aag gtg gat aac gcc ctc caa      645
Tyr Pro Arg Glu Ala Lys Val Gln Trp Lys Val Asp Asn Ala Leu Gln
        165                 170                 175
```

```
tcg ggt aac tcc cag gag agt gtc aca gag cag gac agc aag gac agc    693
Ser Gly Asn Ser Gln Glu Ser Val Thr Glu Gln Asp Ser Lys Asp Ser
    180                 185                 190 acc tac agc ctc agc agc acc ctg acg ctg agc aaa gca gac tac gag    741
Thr Tyr Ser Leu Ser Ser Thr Leu Thr Leu Ser Lys Ala Asp Tyr Glu
195                 200                 205                 210 aaa cac aaa gtc tac gcc tgc gaa gtc acc cat cag ggc ctg agc tcg    789
Lys His Lys Val Tyr Ala Cys Glu Val Thr His Gln Gly Leu Ser Ser
                215                 220                 225 ccc gtc aca aag agc ttc aac agg gga gag ggt ggt gaa cag aaa ctg    837
Pro Val Thr Lys Ser Phe Asn Arg Gly Glu Gly Gly Glu Gln Lys Leu
            230                 235                 240 att agc gaa gaa gat ctg tagtcatccg gctcgtataa tgtgtggaat           885
Ile Ser Glu Glu Asp Leu
            245 tgtgagcgga taacaatttc acacaggaaa cagacctagg aattctaact ttaagaagga  945 gatatacca atg aaa tac ctg ctg ccg acc gtt gct gct ggt ctg ctg ctc  996
           Met Lys Tyr Leu Leu Pro Thr Val Ala Ala Gly Leu Leu Leu
               250                 255                 260 ctc gct gcc cag ccg gcg atg gcc atg gaa gtt caa ctg gtg gag tct   1044
Leu Ala Ala Gln Pro Ala Met Ala Met Glu Val Gln Leu Val Glu Ser
            265                 270                 275 ggc ggt ggc ctg gtt caa cca gga ggc tca ctc cgt ttg tcc tgc gca   1092
Gly Gly Gly Leu Val Gln Pro Gly Gly Ser Leu Arg Leu Ser Cys Ala
280                 285                 290 gca tcc gga ttt aac att aaa gat acc tat atc cac tgg gtg cgt cag   1140
Ala Ser Gly Phe Asn Ile Lys Asp Thr Tyr Ile His Trp Val Arg Gln
295                 300                 305                 310 gct cct ggt aag ggc ctg gaa tgg gtt gcc cgt att tat cct acc aac   1188
Ala Pro Gly Lys Gly Leu Glu Trp Val Ala Arg Ile Tyr Pro Thr Asn
                315                 320                 325 ggc tat act cgt tat gcc gat agc gtc aag ggt cgt ttt act ata agt   1236
Gly Tyr Thr Arg Tyr Ala Asp Ser Val Lys Gly Arg Phe Thr Ile Ser
            330                 335                 340 gcg gat acc tct aaa aac acc gcg tac ctg cag atg aac agt cta aga   1284
Ala Asp Thr Ser Lys Asn Thr Ala Tyr Leu Gln Met Asn Ser Leu Arg
            345                 350                 355 gcg gaa gat act gcc gtc tac tac tgc agc cgc tgg ggc ggc gat ggc   1332
Ala Glu Asp Thr Ala Val Tyr Tyr Cys Ser Arg Trp Gly Gly Asp Gly
360                 365                 370 ttt tac gcg atg gat tac tgg ggc cag gga act ttg gtt act gtt tcc   1380
Phe Tyr Ala Met Asp Tyr Trp Gly Gln Gly Thr Leu Val Thr Val Ser
375                 380                 385                 390 tcc gct agt acc aag ggc cca tcg gtc ttc ccc ctg gca ccc tcc tcc   1428
Ser Ala Ser Thr Lys Gly Pro Ser Val Phe Pro Leu Ala Pro Ser Ser
                395                 400                 405 aag agc acc tct ggg ggc aca gcg gcc ctg ggc tgc ctg gtc aag gac   1476
Lys Ser Thr Ser Gly Gly Thr Ala Ala Leu Gly Cys Leu Val Lys Asp
            410                 415                 420 tac ttc ccc gaa ccg gtg acg gtg tcg tgg aac tca ggc gcc ctg acc   1524
Tyr Phe Pro Glu Pro Val Thr Val Ser Trp Asn Ser Gly Ala Leu Thr
            425                 430                 435 agc ggc gtg cac acc ttc ccg gct gtc cta cag tcc tca gga ctc tac   1572
Ser Gly Val His Thr Phe Pro Ala Val Leu Gln Ser Ser Gly Leu Tyr
            440                 445                 450 tcc ctc agc agc gtg gtg acc gtg ccc tcc agc agc ttg ggc acc cag   1620
Ser Leu Ser Ser Val Val Thr Val Pro Ser Ser Ser Leu Gly Thr Gln
455                 460                 465                 470 acc tac atc tgc aac gtg aat cac aag ccc agc aac acc aag gtg gac   1668
Thr Tyr Ile Cys Asn Val Asn His Lys Pro Ser Asn Thr Lys Val Asp
```

```
                Thr Tyr Ile Cys Asn Val Asn His Lys Pro Ser Asn Thr Lys Val Asp
                                475                 480                 485 aag aaa gtt gaa ccg ggt agt ggt ggg gac tac aaa gac gat gac gat        1716
Lys Lys Val Glu Pro Gly Ser Gly Gly Asp Tyr Lys Asp Asp Asp Asp
            490                 495                 500 aaa tca tct gat tat aag gat gac gat gac aag cat cac cat cat cac        1764
Lys Ser Ser Asp Tyr Lys Asp Asp Asp Asp Lys His His His His His
        505                 510                 515 cat tagtctagag tcgacctgc                                               1786
His
```

```
<210> SEQ ID NO 2
<211> LENGTH: 248
<212> TYPE: PRT
<213> ORGANISM: Artificial sequence
<220> FEATURE:
<223> OTHER INFORMATION: Synthetic Construct

<400> SEQUENCE: 2

Met Lys Tyr Leu Leu Pro Thr Val Ala Ala Gly Leu Leu Leu Leu Ala
1               5                   10                  15

Ala Gln Pro Ala Met Ala Met Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Gly Gly Glu Gln
225                 230                 235                 240

Lys Leu Ile Ser Glu Glu Asp Leu
                245

<210> SEQ ID NO 3
<211> LENGTH: 271
<212> TYPE: PRT
<213> ORGANISM: Artificial sequence
<220> FEATURE:
<223> OTHER INFORMATION: Synthetic Construct
```

<400> SEQUENCE: 3

```
Met Lys Tyr Leu Leu Pro Thr Val Ala Ala Gly Leu Leu Leu Ala
1               5                   10                  15

Ala Gln Pro Ala Met Ala Met Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Gly Ser Gly Gly Asp Tyr Lys Asp Asp Asp Lys Ser
                245                 250                 255

Ser Asp Tyr Lys Asp Asp Asp Lys His His His His His His
            260                 265                 270
```

<210> SEQ ID NO 4
<211> LENGTH: 1792
<212> TYPE: DNA
<213> ORGANISM: Artificial sequence
<220> FEATURE:
<223> OTHER INFORMATION: pTrc FabTT
<220> FEATURE:
<221> NAME/KEY: CDS
<222> LOCATION: (112)..(855)
<220> FEATURE:
<221> NAME/KEY: CDS
<222> LOCATION: (955)..(1773)

<400> SEQUENCE: 4

```
gctgttgaca attaatcatc cggctcgtat aatgtgtgga attgtgagcg gataacaatt      60
tcacacagga aacagaccta ggaattctaa ctttaagaag gagatatacc a atg aaa     117
                                                         Met Lys
                                                           1 tac ctg ctg ccg acc gtt gct gct ggt ctg ctc ctc gct gcc cag          165
Tyr Leu Leu Pro Thr Val Ala Ala Gly Leu Leu Leu Ala Ala Gln
        5                   10                  15
```

| | | | |
|---|---|---|---|
| ccg gcg atg gcc atg gat atc cag atg acc cag tcc ccg agt tct cta<br>Pro Ala Met Ala Met Asp Ile Gln Met Thr Gln Ser Pro Ser Ser Leu<br>20                         25                        30 | 213 |

```
ccg gcg atg gcc atg gat atc cag atg acc cag tcc ccg agt tct cta     213
Pro Ala Met Ala Met Asp Ile Gln Met Thr Gln Ser Pro Ser Ser Leu
 20                  25                  30 tct gct tct gtg ggc gat agg gtc acc atc acc tgc cgt gcc agt cag     261
Ser Ala Ser Val Gly Asp Arg Val Thr Ile Thr Cys Arg Ala Ser Gln
 35                  40                  45                  50 gat att aaa aat tat ttg tct tgg tat caa caa caa cca gga aat gcc     309
Asp Ile Lys Asn Tyr Leu Ser Trp Tyr Gln Gln Gln Pro Gly Asn Ala
                 55                  60                  65 ccg aag cca ctg att tat gct ggt tct aac cgc caa tct gga gtt cct     357
Pro Lys Pro Leu Ile Tyr Ala Gly Ser Asn Arg Gln Ser Gly Val Pro
         70                  75                  80 tct cgc ttc tcc gga tct gga tct gaa act gat ttt act cta act att     405
Ser Arg Phe Ser Gly Ser Gly Ser Glu Thr Asp Phe Thr Leu Thr Ile
             85                  90                  95 agt agt cta cag ccg gag gac ttc gcc acc tat tat tgc caa caa act     453
Ser Ser Leu Gln Pro Glu Asp Phe Ala Thr Tyr Tyr Cys Gln Gln Thr
        100                 105                 110 tac atc tac cct atc act ttc ggc cag ggt acc aag gtg gaa att aaa     501
Tyr Ile Tyr Pro Ile Thr Phe Gly Gln Gly Thr Lys Val Glu Ile Lys
115                 120                 125                 130 cgt act gtg gct gca cca tct gtc ttc atc ttc ccg cca tct gat gag     549
Arg Thr Val Ala Ala Pro Ser Val Phe Ile Phe Pro Pro Ser Asp Glu
                135                 140                 145 cag ttg aaa tct gga act gcc tct gtt gtg tgc ctg ctg aat aac ttc     597
Gln Leu Lys Ser Gly Thr Ala Ser Val Val Cys Leu Leu Asn Asn Phe
            150                 155                 160 tat ccc aga gag gcc aaa gta cag tgg aag gtg gat aac gcc ctc caa     645
Tyr Pro Arg Glu Ala Lys Val Gln Trp Lys Val Asp Asn Ala Leu Gln
        165                 170                 175 tcg ggt aac tcc cag gag agt gtc aca gag cag gac agc aag gac agc     693
Ser Gly Asn Ser Gln Glu Ser Val Thr Glu Gln Asp Ser Lys Asp Ser
    180                 185                 190 acc tac agc ctc agc agc acc ctg acg ctg agc aaa gca gac tac gag     741
Thr Tyr Ser Leu Ser Ser Thr Leu Thr Leu Ser Lys Ala Asp Tyr Glu
195                 200                 205                 210 aaa cac aaa gtc tac gcc tgc gaa gtc acc cat cag ggc ctg agc tcg     789
Lys His Lys Val Tyr Ala Cys Glu Val Thr His Gln Gly Leu Ser Ser
                215                 220                 225 ccc gtc aca aag agc ttc aac agg gga gag ggt ggt gaa cag aaa ctg     837
Pro Val Thr Lys Ser Phe Asn Arg Gly Glu Gly Gly Glu Gln Lys Leu
            230                 235                 240 att agc gaa gaa gat ctg tagtcatccg gctcgtataa tgtgtggaat            885
Ile Ser Glu Glu Asp Leu
            245 tgtgagcgga taacaatttc acacaggaaa cagacctagg aattctaact ttaagaagga   945 gatatacca atg aaa tac ctg ctg ccg acc gtt gct gct ggt ctg ctg ctc   996
            Met Lys Tyr Leu Leu Pro Thr Val Ala Ala Gly Leu Leu Leu
            250                 255                 260 ctc gct gcc cag ccg gcg atg gcc atg gaa gtt caa ctg gtg gag tct    1044
Leu Ala Ala Gln Pro Ala Met Ala Met Glu Val Gln Leu Val Glu Ser
        265                 270                 275 ggc ggt ggc ctg gtt caa cca gga ggc tca ctc cgt ttg tcc tgc gca    1092
Gly Gly Gly Leu Val Gln Pro Gly Gly Ser Leu Arg Leu Ser Cys Ala
    280                 285                 290 gca tcc gga ttt act att gaa cgt tat gcg atg ggt tgg gtg cgt cag    1140
Ala Ser Gly Phe Thr Ile Glu Arg Tyr Ala Met Gly Trp Val Arg Gln
295                 300                 305                 310
```

| | | | | | | | | | | | | | | | | |
|---|---|---|---|---|---|---|---|---|---|---|---|---|---|---|---|---|
| gct | cct | ggt | aag | ggc | ctg | gaa | tgg | gtt | ggt | acg | att | tat | cct | tgg | ggc | 1188 |
| Ala | Pro | Gly | Lys | Gly | Leu | Glu | Trp | Val | Gly | Thr | Ile | Tyr | Pro | Trp | Gly | |
| | | | 315 | | | | | 320 | | | | | 325 | | | |
| gat | tat | act | gat | tat | gcc | gat | agc | gtc | aag | ggt | cgt | ttt | act | ata | agt | 1236 |
| Asp | Tyr | Thr | Asp | Tyr | Ala | Asp | Ser | Val | Lys | Gly | Arg | Phe | Thr | Ile | Ser | |
| | | 330 | | | | | 335 | | | | | 340 | | | | |
| aga | gat | aat | tct | aaa | aac | acc | ctc | tac | ctg | cag | atg | aac | agt | cta | aga | 1284 |
| Arg | Asp | Asn | Ser | Lys | Asn | Thr | Leu | Tyr | Leu | Gln | Met | Asn | Ser | Leu | Arg | |
| | | | 345 | | | | | 350 | | | | | 355 | | | |
| gat | gaa | gat | act | gcc | gtc | tac | tac | tgc | gct | cgc | tct | aac | tac | ccg | aac | 1332 |
| Asp | Glu | Asp | Thr | Ala | Val | Tyr | Tyr | Cys | Ala | Arg | Ser | Asn | Tyr | Pro | Asn | |
| | | 360 | | | | | 365 | | | | | 370 | | | | |
| ggt | atg | tac | tac | gtt | atg | gaa | tac | tgg | ggc | cag | gga | act | ttg | gtt | act | 1380 |
| Gly | Met | Tyr | Tyr | Val | Met | Glu | Tyr | Trp | Gly | Gln | Gly | Thr | Leu | Val | Thr | |
| 375 | | | | | 380 | | | | | 385 | | | | | 390 | |
| gtt | tcc | tcc | gct | agt | acc | aag | ggc | cca | tcg | gtc | ttc | ccc | ctg | gca | ccc | 1428 |
| Val | Ser | Ser | Ala | Ser | Thr | Lys | Gly | Pro | Ser | Val | Phe | Pro | Leu | Ala | Pro | |
| | | | | 395 | | | | | 400 | | | | | 405 | | |
| tcc | tcc | aag | agc | acc | tct | ggg | ggc | aca | gcg | gcc | ctg | ggc | tgc | ctg | gtc | 1476 |
| Ser | Ser | Lys | Ser | Thr | Ser | Gly | Gly | Thr | Ala | Ala | Leu | Gly | Cys | Leu | Val | |
| | | | 410 | | | | | 415 | | | | | 420 | | | |
| aag | gac | tac | ttc | ccc | gaa | ccg | gtg | acg | gtg | tcg | tgg | aac | tca | ggc | gcc | 1524 |
| Lys | Asp | Tyr | Phe | Pro | Glu | Pro | Val | Thr | Val | Ser | Trp | Asn | Ser | Gly | Ala | |
| | | 425 | | | | | 430 | | | | | 435 | | | | |
| ctg | acc | agc | ggc | gtg | cac | acc | ttc | ccg | gct | gtc | cta | cag | tcc | tca | gga | 1572 |
| Leu | Thr | Ser | Gly | Val | His | Thr | Phe | Pro | Ala | Val | Leu | Gln | Ser | Ser | Gly | |
| | | 440 | | | | | 445 | | | | | 450 | | | | |
| ctc | tac | tcc | ctc | agc | agc | gtg | gtg | acc | gtg | ccc | tcc | agc | agc | ttg | ggc | 1620 |
| Leu | Tyr | Ser | Leu | Ser | Ser | Val | Val | Thr | Val | Pro | Ser | Ser | Ser | Leu | Gly | |
| 455 | | | | | 460 | | | | | 465 | | | | | 470 | |
| acc | cag | acc | tac | atc | tgc | aac | gtg | aat | cac | aag | ccc | agc | aac | acc | aag | 1668 |
| Thr | Gln | Thr | Tyr | Ile | Cys | Asn | Val | Asn | His | Lys | Pro | Ser | Asn | Thr | Lys | |
| | | | | 475 | | | | | 480 | | | | | 485 | | |
| gtg | gac | aag | aaa | gtt | gaa | ccg | ggt | agt | ggt | ggg | gac | tac | aaa | gac | gat | 1716 |
| Val | Asp | Lys | Lys | Val | Glu | Pro | Gly | Ser | Gly | Gly | Asp | Tyr | Lys | Asp | Asp | |
| | | | 490 | | | | | 495 | | | | | 500 | | | |
| gac | gat | aaa | tca | tct | gat | tat | aag | gat | gac | gat | gac | aag | cat | cac | cat | 1764 |
| Asp | Asp | Lys | Ser | Ser | Asp | Tyr | Lys | Asp | Asp | Asp | Asp | Lys | His | His | His | |
| | | 505 | | | | | 510 | | | | | 515 | | | | |
| cat | cac | cat | tagtctagag | tcgacctgc | | | | | | | | | | | | 1792 |
| His | His | His | | | | | | | | | | | | | | |
| | | 520 | | | | | | | | | | | | | | |

<210> SEQ ID NO 5
<211> LENGTH: 248
<212> TYPE: PRT
<213> ORGANISM: Artificial sequence
<220> FEATURE:
<223> OTHER INFORMATION: Synthetic Construct

<400> SEQUENCE: 5

Met Lys Tyr Leu Leu Pro Thr Val Ala Ala Gly Leu Leu Leu Leu Ala
1               5                   10                  15

Ala Gln Pro Ala Met Ala Met Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Ile Lys Asn Tyr Leu Ser Trp Tyr Gln Gln Pro Gly
    50                  55                  60

Asn Ala Pro Lys Pro Leu Ile Tyr Ala Gly Ser Asn Arg Gln Ser Gly

```
                65                  70                  75                  80
Val Pro Ser Arg Phe Ser Gly Ser Gly Ser Glu Thr Asp Phe Thr Leu
                    85                  90                  95

Thr Ile Ser Ser Leu Gln Pro Glu Asp Phe Ala Thr Tyr Tyr Cys Gln
                100                 105                 110

Gln Thr Tyr Ile Tyr Pro Ile Thr Phe Gly Gln Gly Thr Lys Val Glu
                115                 120                 125

Ile Lys Arg Thr Val Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Gly Gly Glu Gln
225                 230                 235                 240

Lys Leu Ile Ser Glu Glu Asp Leu
                245

<210> SEQ ID NO 6
<211> LENGTH: 273
<212> TYPE: PRT
<213> ORGANISM: Artificial sequence
<220> FEATURE:
<223> OTHER INFORMATION: Synthetic Construct

<400> SEQUENCE: 6

Met Lys Tyr Leu Leu Pro Thr Val Ala Ala Gly Leu Leu Leu Leu Ala
1               5                   10                  15

Ala Gln Pro Ala Met Ala Met Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Thr Ile Glu Arg Tyr Ala Met Gly Trp Val Arg Gln Ala Pro
        50                  55                  60

Gly Lys Gly Leu Glu Trp Val Gly Thr Ile Tyr Pro Trp Gly Asp Tyr
65                  70                  75                  80

Thr Asp Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Asp Glu
                100                 105                 110

Asp Thr Ala Val Tyr Tyr Cys Ala Arg Ser Asn Tyr Pro Asn Gly Met
            115                 120                 125

Tyr Tyr Val Met Glu Tyr Trp Gly Gln Gly Thr Leu Val Thr Val Ser
        130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
```

-continued

```
                180                 185                 190
Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Gly Ser Gly Gly Asp Tyr Lys Asp Asp Asp Asp
                245                 250                 255

Lys Ser Ser Asp Tyr Lys Asp Asp Asp Asp Lys His His His His His
            260                 265                 270

His

<210> SEQ ID NO 7
<211> LENGTH: 1792
<212> TYPE: DNA
<213> ORGANISM: Artificial sequence
<220> FEATURE:
<223> OTHER INFORMATION: pTrc FabHT
<220> FEATURE:
<221> NAME/KEY: CDS
<222> LOCATION: (112)..(855)
<220> FEATURE:
<221> NAME/KEY: CDS
<222> LOCATION: (955)..(1773)

<400> SEQUENCE: 7
gctgttgaca attaatcatc cggctcgtat aatgtgtgga attgtgagcg gataacaatt      60
tcacacagga aacagaccta ggaattctaa ctttaagaag gagatatacc a atg aaa     117
                                                          Met Lys
                                                            1 tac ctg ctg ccg acc gtt gct gct ggt ctg ctc ctc gct gcc cag          165
Tyr Leu Leu Pro Thr Val Ala Ala Gly Leu Leu Leu Ala Ala Gln
          5                  10                  15 ccg gcg atg gcc atg gat atc cag atg acc cag tcc ccg agt tct cta     213
Pro Ala Met Ala Met Asp Ile Gln Met Thr Gln Ser Pro Ser Ser Leu
         20                  25                  30 tct gct tct gtg ggc gat agg gtc acc atc acc tgc cgt gcc agt cag     261
Ser Ala Ser Val Gly Asp Arg Val Thr Ile Thr Cys Arg Ala Ser Gln
 35                  40                  45                  50 gat gtg aac acc gcc gtt gca tgg tat caa caa aaa cca gga aaa gcc     309
Asp Val Asn Thr Ala Val Ala Trp Tyr Gln Gln Lys Pro Gly Lys Ala
                 55                  60                  65 ccg aag ctg ctg att tat agc gcc tct ttt ctg tat tct gga gtt cct     357
Pro Lys Leu Leu Ile Tyr Ser Ala Ser Phe Leu Tyr Ser Gly Val Pro
             70                  75                  80 tct cgc ttc tcc gga tcc cgt tct ggc act gat ttt act cta act att     405
Ser Arg Phe Ser Gly Ser Arg Ser Gly Thr Asp Phe Thr Leu Thr Ile
         85                  90                  95 agt agt cta cag ccg gag gac ttc gcc acc tat tat tgc caa caa cat     453
Ser Ser Leu Gln Pro Glu Asp Phe Ala Thr Tyr Tyr Cys Gln Gln His
            100                 105                 110 tac acc acc cct ccg act ttc ggc cag ggt acc aag gtg gaa att aaa     501
Tyr Thr Thr Pro Pro Thr Phe Gly Gln Gly Thr Lys Val Glu Ile Lys
115                 120                 125                 130 cgt act gtg gct gca cca tct gtc ttc atc ttc ccg cca tct gat gag     549
Arg Thr Val Ala Ala Pro Ser Val Phe Ile Phe Pro Pro Ser Asp Glu
                135                 140                 145 cag ttg aaa tct gga act gcc tct gtt gtg tgc ctg ctg aat aac ttc     597
Gln Leu Lys Ser Gly Thr Ala Ser Val Val Cys Leu Leu Asn Asn Phe
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     | 150 |     |     |     | 155 |     |     |     | 160 |     |     |     |     |
| tat | ccc | aga | gag | gcc | aaa | gta | cag | tgg | aag | gtg | gat | aac | gcc | ctc | caa | 645 |
| Tyr | Pro | Arg | Glu | Ala | Lys | Val | Gln | Trp | Lys | Val | Asp | Asn | Ala | Leu | Gln |
|     |     | 165 |     |     |     |     | 170 |     |     |     |     | 175 |     |     |     |
| tcg | ggt | aac | tcc | cag | gag | agt | gtc | aca | gag | cag | gac | agc | aag | gac | agc | 693 |
| Ser | Gly | Asn | Ser | Gln | Glu | Ser | Val | Thr | Glu | Gln | Asp | Ser | Lys | Asp | Ser |
|     | 180 |     |     |     |     | 185 |     |     |     |     | 190 |     |     |     |     |
| acc | tac | agc | ctc | agc | agc | acc | ctg | acg | ctg | agc | aaa | gca | gac | tac | gag | 741 |
| Thr | Tyr | Ser | Leu | Ser | Ser | Thr | Leu | Thr | Leu | Ser | Lys | Ala | Asp | Tyr | Glu |
| 195 |     |     |     |     | 200 |     |     |     |     | 205 |     |     |     |     | 210 |
| aaa | cac | aaa | gtc | tac | gcc | tgc | gaa | gtc | acc | cat | cag | ggc | ctg | agc | tcg | 789 |
| Lys | His | Lys | Val | Tyr | Ala | Cys | Glu | Val | Thr | His | Gln | Gly | Leu | Ser | Ser |
|     |     |     |     | 215 |     |     |     |     | 220 |     |     |     |     | 225 |     |
| ccc | gtc | aca | aag | agc | ttc | aac | agg | gga | gag | ggt | ggt | gaa | cag | aaa | ctg | 837 |
| Pro | Val | Thr | Lys | Ser | Phe | Asn | Arg | Gly | Glu | Gly | Gly | Glu | Gln | Lys | Leu |
|     |     | 230 |     |     |     |     | 235 |     |     |     |     | 240 |     |     |     |
| att | agc | gaa | gaa | gat | ctg | tagtcatccg | gctcgtataa | tgtgtggaat |  |  |  |  |  |  | 885 |
| Ile | Ser | Glu | Glu | Asp | Leu |
|     |     | 245 |     |     |     | tgtgagcgga taacaatttc acacaggaaa cagacctagg aattctaact ttaagaagga    945

|     |     |     |     |     |     |     |     |     |     |     |     |     |     |     |     |
| --- | --- | --- | --- | --- | --- | --- | --- | --- | --- | --- | --- | --- | --- | --- | --- |
| gatatacca | atg | aaa | tac | ctg | ctg | ccg | acc | gtt | gct | gct | ggt | ctg | ctg | ctc |   | 996 |
|           | Met | Lys | Tyr | Leu | Leu | Pro | Thr | Val | Ala | Ala | Gly | Leu | Leu | Leu |
|           |     | 250 |     |     |     |     | 255 |     |     |     |     | 260 |     |     |
| ctc | gct | gcc | cag | ccg | gcg | atg | gcc | atg | gaa | gtt | caa | ctg | gtg | gag | tct | 1044 |
| Leu | Ala | Ala | Gln | Pro | Ala | Met | Ala | Met | Glu | Val | Gln | Leu | Val | Glu | Ser |
|     |     |     | 265 |     |     |     |     | 270 |     |     |     |     | 275 |     |     |
| ggc | ggt | ggc | ctg | gtt | caa | cca | gga | ggc | tca | ctc | cgt | ttg | tcc | tgc | gca | 1092 |
| Gly | Gly | Gly | Leu | Val | Gln | Pro | Gly | Gly | Ser | Leu | Arg | Leu | Ser | Cys | Ala |
|     | 280 |     |     |     |     | 285 |     |     |     |     | 290 |     |     |     |     |
| gca | tcc | gga | ttt | act | att | gaa | cgt | tat | gcg | atg | ggt | tgg | gtg | cgt | cag | 1140 |
| Ala | Ser | Gly | Phe | Thr | Ile | Glu | Arg | Tyr | Ala | Met | Gly | Trp | Val | Arg | Gln |
| 295 |     |     |     |     | 300 |     |     |     |     | 305 |     |     |     |     | 310 |
| gct | cct | ggt | aag | ggc | ctg | gaa | tgg | gtt | ggt | acg | att | tat | cct | tgg | ggc | 1188 |
| Ala | Pro | Gly | Lys | Gly | Leu | Glu | Trp | Val | Gly | Thr | Ile | Tyr | Pro | Trp | Gly |
|     |     |     |     | 315 |     |     |     |     | 320 |     |     |     |     | 325 |     |
| gat | tat | act | gat | tat | gcc | gat | agc | gtc | aag | ggt | cgt | ttt | act | ata | agt | 1236 |
| Asp | Tyr | Thr | Asp | Tyr | Ala | Asp | Ser | Val | Lys | Gly | Arg | Phe | Thr | Ile | Ser |
|     |     | 330 |     |     |     |     | 335 |     |     |     |     | 340 |     |     |     |
| aga | gat | aat | tct | aaa | aac | acc | ctc | tac | ctg | cag | atg | aac | agt | cta | aga | 1284 |
| Arg | Asp | Asn | Ser | Lys | Asn | Thr | Leu | Tyr | Leu | Gln | Met | Asn | Ser | Leu | Arg |
|     | 345 |     |     |     |     | 350 |     |     |     |     | 355 |     |     |     |     |
| gat | gaa | gat | act | gcc | gtc | tac | tac | tgc | gct | cgc | tct | aac | tac | ccg | aac | 1332 |
| Asp | Glu | Asp | Thr | Ala | Val | Tyr | Tyr | Cys | Ala | Arg | Ser | Asn | Tyr | Pro | Asn |
| 360 |     |     |     |     | 365 |     |     |     |     | 370 |     |     |     |     |     |
| ggt | atg | tac | tac | gtt | atg | gaa | tac | tgg | ggc | cag | gga | act | ttg | gtt | act | 1380 |
| Gly | Met | Tyr | Tyr | Val | Met | Glu | Tyr | Trp | Gly | Gln | Gly | Thr | Leu | Val | Thr |
| 375 |     |     |     | 380 |     |     |     |     | 385 |     |     |     |     | 390 |     |
| gtt | tcc | tcc | gct | agt | acc | aag | ggc | cca | tcg | gtc | ttc | ccc | ctg | gca | ccc | 1428 |
| Val | Ser | Ser | Ala | Ser | Thr | Lys | Gly | Pro | Ser | Val | Phe | Pro | Leu | Ala | Pro |
|     |     |     | 395 |     |     |     |     | 400 |     |     |     |     | 405 |     |     |
| tcc | tcc | aag | agc | acc | tct | ggg | ggc | aca | gcg | gcc | ctg | ggc | tgc | ctg | gtc | 1476 |
| Ser | Ser | Lys | Ser | Thr | Ser | Gly | Gly | Thr | Ala | Ala | Leu | Gly | Cys | Leu | Val |
|     | 410 |     |     |     |     | 415 |     |     |     |     | 420 |     |     |     |     |
| aag | gac | tac | ttc | ccc | gaa | ccg | gtg | acg | gtg | tcg | tgg | aac | tca | ggc | gcc | 1524 |
| Lys | Asp | Tyr | Phe | Pro | Glu | Pro | Val | Thr | Val | Ser | Trp | Asn | Ser | Gly | Ala |
| 425 |     |     |     |     | 430 |     |     |     |     | 435 |     |     |     |     |     |
| ctg | acc | agc | ggc | gtg | cac | acc | ttc | ccg | gct | gtc | cta | cag | tcc | tca | gga | 1572 |
| Leu | Thr | Ser | Gly | Val | His | Thr | Phe | Pro | Ala | Val | Leu | Gln | Ser | Ser | Gly |
|     |     | 440 |     |     |     |     | 445 |     |     |     |     | 450 |     |     |     |

```
ctc tac tcc ctc agc agc gtg gtg acc gtg ccc tcc agc agc ttg ggc      1620
Leu Tyr Ser Leu Ser Ser Val Val Thr Val Pro Ser Ser Ser Leu Gly
455                 460                 465                 470 acc cag acc tac atc tgc aac gtg aat cac aag ccc agc aac acc aag      1668
Thr Gln Thr Tyr Ile Cys Asn Val Asn His Lys Pro Ser Asn Thr Lys
                475                 480                 485 gtg gac aag aaa gtt gaa ccg ggt agt ggt ggg gac tac aaa gac gat      1716
Val Asp Lys Lys Val Glu Pro Gly Ser Gly Gly Asp Tyr Lys Asp Asp
                490                 495                 500 gac gat aaa tca tct gat tat aag gat gac gat gac aag cat cac cat      1764
Asp Asp Lys Ser Ser Asp Tyr Lys Asp Asp Asp Asp Lys His His His
                505                 510                 515 cat cac cat tagtctagag tcgacctgc                                     1792
His His His
    520

<210> SEQ ID NO 8
<211> LENGTH: 248
<212> TYPE: PRT
<213> ORGANISM: Artificial sequence
<220> FEATURE:
<223> OTHER INFORMATION: Synthetic Construct

<400> SEQUENCE: 8

Met Lys Tyr Leu Leu Pro Thr Val Ala Ala Gly Leu Leu Leu Leu Ala
1               5                   10                  15

Ala Gln Pro Ala Met Ala Met Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Gln Asp Val Asn Thr Ala Val Ala Trp Tyr Gln Gln Lys Pro Gly
        50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Gly Gly Glu Gln
225                 230                 235                 240

Lys Leu Ile Ser Glu Glu Asp Leu
                245
```

```
<210> SEQ ID NO 9
<211> LENGTH: 273
<212> TYPE: PRT
<213> ORGANISM: Artificial sequence
<220> FEATURE:
<223> OTHER INFORMATION: Synthetic Construct

<400> SEQUENCE: 9

Met Lys Tyr Leu Leu Pro Thr Val Ala Ala Gly Leu Leu Leu Ala
1               5                   10                  15

Ala Gln Pro Ala Met Ala Met Glu Val Gln Leu Val Glu Ser Gly Gly
            20                  25                  30

Gly Leu Val Gln Pro Gly Gly Ser Leu Arg Leu Ser Cys Ala Ala Ser
            35                  40                  45

Gly Phe Thr Ile Glu Arg Tyr Ala Met Gly Trp Val Arg Gln Ala Pro
    50                  55                  60

Gly Lys Gly Leu Glu Trp Val Gly Thr Ile Tyr Pro Trp Gly Asp Tyr
65                  70                  75                  80

Thr Asp Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Asp Glu
            100                 105                 110

Asp Thr Ala Val Tyr Tyr Cys Ala Arg Ser Asn Tyr Pro Asn Gly Met
            115                 120                 125

Tyr Tyr Val Met Glu Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Gly Ser Gly Gly Asp Tyr Lys Asp Asp Asp Asp
                245                 250                 255

Lys Ser Ser Asp Tyr Lys Asp Asp Asp Lys His His His His
            260                 265                 270
His

<210> SEQ ID NO 10
<211> LENGTH: 1786
<212> TYPE: DNA
<213> ORGANISM: Artificial sequence
<220> FEATURE:
<223> OTHER INFORMATION: pTrc FabTH
<220> FEATURE:
<221> NAME/KEY: CDS
<222> LOCATION: (112)..(855)
<220> FEATURE:
<221> NAME/KEY: CDS
<222> LOCATION: (955)..(1767)

<400> SEQUENCE: 10
```

```
gctgttgaca attaatcatc cggctcgtat aatgtgtgga attgtgagcg gataacaatt      60
tcacacagga aacagaccta ggaattctaa ctttaagaag gagatatacc a atg aaa     117
                                                         Met Lys
                                                           1 tac ctg ctg ccg acc gtt gct gct ggt ctg ctg ctc ctc gct gcc cag     165
Tyr Leu Leu Pro Thr Val Ala Ala Gly Leu Leu Leu Leu Ala Ala Gln
          5                  10                  15 ccg gcg atg gcc atg gat atc cag atg acc cag tcc ccg agt tct cta     213
Pro Ala Met Ala Met Asp Ile Gln Met Thr Gln Ser Pro Ser Ser Leu
         20                  25                  30 tct gct tct gtg ggc gat agg gtc acc atc acc tgc cgt gcc agt cag     261
Ser Ala Ser Val Gly Asp Arg Val Thr Ile Thr Cys Arg Ala Ser Gln
 35                  40                  45                  50 gat att aaa aat tat ttg tct tgg tat caa caa caa cca gga aat gcc     309
Asp Ile Lys Asn Tyr Leu Ser Trp Tyr Gln Gln Gln Pro Gly Asn Ala
                 55                  60                  65 ccg aag cca ctg att tat gct ggt tct aac cgc caa tct gga gtt cct     357
Pro Lys Pro Leu Ile Tyr Ala Gly Ser Asn Arg Gln Ser Gly Val Pro
         70                  75                  80 tct cgc ttc tcc gga tct gga tct gaa act gat ttt act cta act att     405
Ser Arg Phe Ser Gly Ser Gly Ser Glu Thr Asp Phe Thr Leu Thr Ile
         85                  90                  95 agt agt cta cag ccg gag gac ttc gcc acc tat tat tgc caa caa act     453
Ser Ser Leu Gln Pro Glu Asp Phe Ala Thr Tyr Tyr Cys Gln Gln Thr
100                 105                 110 tac atc tac cct atc act ttc ggc cag ggt acc aag gtg gaa att aaa     501
Tyr Ile Tyr Pro Ile Thr Phe Gly Gln Gly Thr Lys Val Glu Ile Lys
115                 120                 125                 130 cgt act gtg gct gca cca tct gtc ttc atc ttc ccg cca tct gat gag     549
Arg Thr Val Ala Ala Pro Ser Val Phe Ile Phe Pro Pro Ser Asp Glu
                135                 140                 145 cag ttg aaa tct gga act gcc tct gtt gtg tgc ctg ctg aat aac ttc     597
Gln Leu Lys Ser Gly Thr Ala Ser Val Val Cys Leu Leu Asn Asn Phe
            150                 155                 160 tat ccc aga gag gcc aaa gta cag tgg aag gtg gat aac gcc ctc caa     645
Tyr Pro Arg Glu Ala Lys Val Gln Trp Lys Val Asp Asn Ala Leu Gln
            165                 170                 175 tcg ggt aac tcc cag gag agt gtc aca gag cag gac agc aag gac agc     693
Ser Gly Asn Ser Gln Glu Ser Val Thr Glu Gln Asp Ser Lys Asp Ser
        180                 185                 190 acc tac agc ctc agc agc acc ctg acg ctg agc aaa gca gac tac gag     741
Thr Tyr Ser Leu Ser Ser Thr Leu Thr Leu Ser Lys Ala Asp Tyr Glu
195                 200                 205                 210 aaa cac aaa gtc tac gcc tgc gaa gtc acc cat cag ggc ctg agc tcg     789
Lys His Lys Val Tyr Ala Cys Glu Val Thr His Gln Gly Leu Ser Ser
                215                 220                 225 ccc gtc aca aag agc ttc aac agg gga gag ggt ggt gaa cag aaa ctg     837
Pro Val Thr Lys Ser Phe Asn Arg Gly Glu Gly Gly Glu Gln Lys Leu
            230                 235                 240 att agc gaa gaa gat ctg tagtcatccg gctcgtataa tgtgtggaat            885
Ile Ser Glu Glu Asp Leu
            245 tgtgagcgga taacaatttc acacaggaaa cagacctagg aattctaact ttaagaagga   945 gatatacca atg aaa tac ctg ctg ccg acc gtt gct gct ggt ctg ctg ctc    996
         Met Lys Tyr Leu Leu Pro Thr Val Ala Ala Gly Leu Leu Leu
           250                 255                 260 ctc gct gcc cag ccg gcg atg gcc atg gaa gtt caa ctg gtg gag tct   1044
Leu Ala Ala Gln Pro Ala Met Ala Met Glu Val Gln Leu Val Glu Ser
                265                 270                 275
```

```
ggc ggt ggc ctg gtt caa cca gga ggc tca ctc cgt ttg tcc tgc gca      1092
Gly Gly Gly Leu Val Gln Pro Gly Gly Ser Leu Arg Leu Ser Cys Ala
            280                 285                 290 gca tcc gga ttt aac att aaa gat acc tat atc cac tgg gtg cgt cag      1140
Ala Ser Gly Phe Asn Ile Lys Asp Thr Tyr Ile His Trp Val Arg Gln
295                 300                 305                 310 gct cct ggt aag ggc ctg gaa tgg gtt gcc cgt att tat cct acc aac      1188
Ala Pro Gly Lys Gly Leu Glu Trp Val Ala Arg Ile Tyr Pro Thr Asn
                315                 320                 325 ggc tat act cgt tat gcc gat agc gtc aag ggt cgt ttt act ata agt      1236
Gly Tyr Thr Arg Tyr Ala Asp Ser Val Lys Gly Arg Phe Thr Ile Ser
            330                 335                 340 gcg gat acc tct aaa aac acc gcg tac ctg cag atg aac agt cta aga      1284
Ala Asp Thr Ser Lys Asn Thr Ala Tyr Leu Gln Met Asn Ser Leu Arg
345                 350                 355 gcg gaa gat act gcc gtc tac tac tgc agc cgc tgg ggc ggc gat ggc      1332
Ala Glu Asp Thr Ala Val Tyr Tyr Cys Ser Arg Trp Gly Gly Asp Gly
                360                 365                 370 ttt tac gcg atg gat tac tgg ggc cag gga act ttg gtt act gtt tcc      1380
Phe Tyr Ala Met Asp Tyr Trp Gly Gln Gly Thr Leu Val Thr Val Ser
375                 380                 385                 390 tcc gct agt acc aag ggc cca tcg gtc ttc ccc ctg gca ccc tcc tcc      1428
Ser Ala Ser Thr Lys Gly Pro Ser Val Phe Pro Leu Ala Pro Ser Ser
                395                 400                 405 aag agc acc tct ggg ggc aca gcg gcc ctg ggc tgc ctg gtc aag gac      1476
Lys Ser Thr Ser Gly Gly Thr Ala Ala Leu Gly Cys Leu Val Lys Asp
            410                 415                 420 tac ttc ccc gaa ccg gtg acg gtg tcg tgg aac tca ggc gcc ctg acc      1524
Tyr Phe Pro Glu Pro Val Thr Val Ser Trp Asn Ser Gly Ala Leu Thr
        425                 430                 435 agc ggc gtg cac acc ttc ccg gct gtc cta cag tcc tca gga ctc tac      1572
Ser Gly Val His Thr Phe Pro Ala Val Leu Gln Ser Ser Gly Leu Tyr
            440                 445                 450 tcc ctc agc agc gtg gtg acc gtg ccc tcc agc agc ttg ggc acc cag      1620
Ser Leu Ser Ser Val Val Thr Val Pro Ser Ser Ser Leu Gly Thr Gln
455                 460                 465                 470 acc tac atc tgc aac gtg aat cac aag ccc agc aac acc aag gtg gac      1668
Thr Tyr Ile Cys Asn Val Asn His Lys Pro Ser Asn Thr Lys Val Asp
                475                 480                 485 aag aaa gtt gaa ccg ggt agt ggt ggg gac tac aaa gac gat gac gat      1716
Lys Lys Val Glu Pro Gly Ser Gly Gly Asp Tyr Lys Asp Asp Asp Asp
            490                 495                 500 aaa tca tct gat tat aag gat gac gat gac aag cat cac cat cat cac      1764
Lys Ser Ser Asp Tyr Lys Asp Asp Asp Asp Lys His His His His His
        505                 510                 515 cat tagtctagag tcgacctgc                                             1786
His
```

<210> SEQ ID NO 11
<211> LENGTH: 248
<212> TYPE: PRT
<213> ORGANISM: Artificial sequence
<220> FEATURE:
<223> OTHER INFORMATION: Synthetic Construct

<400> SEQUENCE: 11

```
Met Lys Tyr Leu Leu Pro Thr Val Ala Ala Gly Leu Leu Leu Leu Ala
1               5                   10                  15

Ala Gln Pro Ala Met Ala Met Asp Ile Gln Met Thr Gln Ser Pro Ser
            20                  25                  30
```

Ser Leu Ser Ala Ser Val Gly Asp Arg Val Thr Ile Thr Cys Arg Ala
            35                  40                  45

Ser Gln Asp Ile Lys Asn Tyr Leu Ser Trp Tyr Gln Gln Pro Gly
 50                  55                  60

Asn Ala Pro Lys Pro Leu Ile Tyr Ala Gly Ser Asn Arg Gln Ser Gly
 65                  70                  75                  80

Val Pro Ser Arg Phe Ser Gly Ser Gly Ser Glu Thr Asp Phe Thr Leu
                85                  90                  95

Thr Ile Ser Ser Leu Gln Pro Glu Asp Phe Ala Thr Tyr Tyr Cys Gln
            100                 105                 110

Gln Thr Tyr Ile Tyr Pro Ile Thr Phe Gly Gln Gly Thr Lys Val Glu
            115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Gly Gly Glu Gln
225                 230                 235                 240

Lys Leu Ile Ser Glu Glu Asp Leu
                245

<210> SEQ ID NO 12
<211> LENGTH: 271
<212> TYPE: PRT
<213> ORGANISM: Artificial sequence
<220> FEATURE:
<223> OTHER INFORMATION: Synthetic Construct

<400> SEQUENCE: 12

Met Lys Tyr Leu Leu Pro Thr Val Ala Ala Gly Leu Leu Leu Leu Ala
  1               5                  10                  15

Ala Gln Pro Ala Met Ala Met Glu Val Gln Leu Val Glu Ser Gly Gly
             20                  25                  30

Gly Leu Val Gln Pro Gly Gly Ser Leu Arg Leu Ser Cys Ala Ala Ser
            35                  40                  45

Gly Phe Asn Ile Lys Asp Thr Tyr Ile His Trp Val Arg Gln Ala Pro
 50                  55                  60

Gly Lys Gly Leu Glu Trp Val Ala Arg Ile Tyr Pro Thr Asn Gly Tyr
 65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
            115                 120                 125

Ala Met Asp Tyr Trp Gly Gln Gly Thr Leu Val Thr Val Ser Ser Ala
130                 135                 140

```
Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
        180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Gly Ser Gly Gly Asp Tyr Lys Asp Asp Asp Asp Lys Ser
            245                 250                 255

Ser Asp Tyr Lys Asp Asp Asp Asp Lys His His His His His His
                260                 265                 270

<210> SEQ ID NO 13
<211> LENGTH: 2477
<212> TYPE: DNA
<213> ORGANISM: Artificial sequence
<220> FEATURE:
<223> OTHER INFORMATION: pGAv2 Fab-HHxhoI
<220> FEATURE:
<221> NAME/KEY: CDS
<222> LOCATION: (94)..(1158)
<220> FEATURE:
<221> NAME/KEY: CDS
<222> LOCATION: (1264)..(2364)

<400> SEQUENCE: 13
aatttcggta atacgactca ctatagggag accacaacgg tttcccattt aggtgacact     60
atagaagtgt aactttaaga aggagatata cca atg gat att cag atg acc cag    114
                                    Met Asp Ile Gln Met Thr Gln
                                      1               5 agc ccg agc agc ctg agc gca agc gtt ggt gat cgt gtc acc atc acc    162
Ser Pro Ser Ser Leu Ser Ala Ser Val Gly Asp Arg Val Thr Ile Thr
         10                  15                  20 tgc cgt gcc agt cag gat gtg aac acc gcc gtt gca tgg tat caa caa    210
Cys Arg Ala Ser Gln Asp Val Asn Thr Ala Val Ala Trp Tyr Gln Gln
 25                  30                  35 aaa cca gga aaa gcc ccg aag ctg ctg att tat agc gcc tct ttt ctg    258
Lys Pro Gly Lys Ala Pro Lys Leu Leu Ile Tyr Ser Ala Ser Phe Leu
 40                  45                  50                  55 tat tct gga gtt cct tct cgc ttc tcc gga tcc cgt tct ggc act gat    306
Tyr Ser Gly Val Pro Ser Arg Phe Ser Gly Ser Arg Ser Gly Thr Asp
                 60                  65                  70 ttt act cta act att agt agt cta cag ccg gag gac ttc gcc acc tat    354
Phe Thr Leu Thr Ile Ser Ser Leu Gln Pro Glu Asp Phe Ala Thr Tyr
             75                  80                  85 tat tgc caa caa cat tac acc acc cct ccg act ttc ggc cag ggt acc    402
Tyr Cys Gln Gln His Tyr Thr Thr Pro Pro Thr Phe Gly Gln Gly Thr
         90                  95                 100 aag gtg gaa att aaa cgt acc gtt gca gca ccg agc gtt ttt att ttt    450
Lys Val Glu Ile Lys Arg Thr Val Ala Ala Pro Ser Val Phe Ile Phe
    105                 110                 115 ccg cct agt gat gaa cag ctg aaa agc ggc acc gca agc gtt gtt tgt    498
Pro Pro Ser Asp Glu Gln Leu Lys Ser Gly Thr Ala Ser Val Val Cys
120                 125                 130                 135
```

-continued

| | | |
|---|---|---|
| ctg ctg aat aat ttt tat ccg cgt gaa gca aaa gtg cag tgg aaa gtt<br>Leu Leu Asn Asn Phe Tyr Pro Arg Glu Ala Lys Val Gln Trp Lys Val<br>140                            145                        150 | | 546 |
| gat aat gca ctg cag agc ggt aat agc caa gaa agc gtt acc gaa cag<br>Asp Asn Ala Leu Gln Ser Gly Asn Ser Gln Glu Ser Val Thr Glu Gln<br>          155                          160                        165 | | 594 |
| gat agc aaa gat agc acc tat agc ctg agc agc acc ctg acc ctg agc<br>Asp Ser Lys Asp Ser Thr Tyr Ser Leu Ser Ser Thr Leu Thr Leu Ser<br>       170                        175                        180 | | 642 |
| aaa gca gat tat gaa aaa cac aaa gtg tat gcc tgc gaa gtt acc cat<br>Lys Ala Asp Tyr Glu Lys His Lys Val Tyr Ala Cys Glu Val Thr His<br>185                            190                        195 | | 690 |
| cag ggt ctg agc agt ccg gtt acc aaa agc ttt aat cgt ggt gaa tgc<br>Gln Gly Leu Ser Ser Pro Val Thr Lys Ser Phe Asn Arg Gly Glu Cys<br>200                          205                        210                        215 | | 738 |
| ggt ggc gat tat aaa gat gat gat gat aaa agc ggt agc agc ggt agt<br>Gly Gly Asp Tyr Lys Asp Asp Asp Asp Lys Ser Gly Ser Ser Gly Ser<br>                    220                          225                        230 | | 786 |
| ggt agc ggt agc agt agt agc ggt tca agc ggt ggt ggc agc agc agc<br>Gly Ser Gly Ser Ser Ser Ser Gly Ser Ser Gly Gly Gly Ser Ser Ser<br>       235                        240                        245 | | 834 |
| tca ggt agt ggt ggt ggt ggt tca agc agc ggt ggt ggc agc agc ggt<br>Ser Gly Ser Gly Gly Gly Gly Ser Ser Ser Gly Gly Gly Ser Ser Gly<br>250                          255                        260 | | 882 |
| agc tca agc ggt agc tct agc agc ggt tct ggt agc agt ggt tca ggt<br>Ser Ser Ser Gly Ser Ser Ser Ser Gly Ser Gly Ser Ser Gly Ser Gly<br>       265                        270                        275 | | 930 |
| agt agc agc agc ggt ggc ggt ggt ggc tca agt agt ggt agc agc tca<br>Ser Ser Ser Ser Gly Gly Gly Gly Ser Ser Ser Gly Ser Ser Ser<br>280                          285                        290                        295 | | 978 |
| tca ggt ggc ggt ggc ggt agt agc tct ggt agc tca agt ggt tct ggt<br>Ser Gly Gly Gly Gly Ser Ser Ser Gly Ser Ser Ser Gly Ser Gly<br>                    300                          305                        310 | | 1026 |
| ggt ggt agt tct agc ggt agt agt ggt ggt tct agc tca agc agc agc<br>Gly Gly Ser Ser Ser Gly Ser Ser Gly Gly Ser Ser Ser Ser Ser<br>                315                        320                        325 | | 1074 |
| agc tcc tcg agc ggt ggt agc ggt gca aaa ttt agc aca ccg gtt tgg<br>Ser Ser Ser Ser Gly Gly Ser Gly Ala Lys Phe Ser Thr Pro Val Trp<br>            330                        335                        340 | | 1122 |
| att agc cag gca cag ggt att cgt gca ggt ccg cct taatgaggcg<br>Ile Ser Gln Ala Gln Gly Ile Arg Ala Gly Pro Pro<br>345                            350                        355 | | 1168 |
| gattgaatga gcataaatta ttcgagatcg atctcgatcc cgcgaaatgc cctctagaa | | 1228 |
| ataattttgt ttaactttaa gaaggagata tacat atg gaa gtt cag ctg gtt<br>                                                           Met Glu Val Gln Leu Val<br>                                                                                                           360 | | 1281 |
| gaa tca ggt ggt ggt ctg gtt cag cct gga ggc tca ctc cgt ttg tcc<br>Glu Ser Gly Gly Gly Leu Val Gln Pro Gly Gly Ser Leu Arg Leu Ser<br>                    365                          370                        375 | | 1329 |
| tgc gca gca tcc gga ttt aac att aaa gat acc tat atc cac tgg gtg<br>Cys Ala Ala Ser Gly Phe Asn Ile Lys Asp Thr Tyr Ile His Trp Val<br>                380                        385                        390 | | 1377 |
| cgt cag gct cct ggt aag ggc ctg gaa tgg gtt gcc cgt att tat cct<br>Arg Gln Ala Pro Gly Lys Gly Leu Glu Trp Val Ala Arg Ile Tyr Pro<br>395                            400                        405 | | 1425 |
| acc aac ggc tat act cgt tat gcc gat agc gtc aag ggt cgt ttt act<br>Thr Asn Gly Tyr Thr Arg Tyr Ala Asp Ser Val Lys Gly Arg Phe Thr<br>410                            415                        420                        425 | | 1473 |
| ata agt gcg gat acc tct aaa aac acc gcg tac ctg cag atg aac agt | | 1521 |

```
                Ile Ser Ala Asp Thr Ser Lys Asn Thr Ala Tyr Leu Gln Met Asn Ser
                                430                 435                 440 cta aga gcg gaa gat act gcc gtc tac tac tgc agc cgc tgg ggc ggc            1569
Leu Arg Ala Glu Asp Thr Ala Val Tyr Tyr Cys Ser Arg Trp Gly Gly
            445                 450                 455 gat ggc ttt tac gcg atg gat tac tgg ggc cag gga act ttg gtt act            1617
Asp Gly Phe Tyr Ala Met Asp Tyr Trp Gly Gln Gly Thr Leu Val Thr
                460                 465                 470 gtt tcc agc gca agc acc aaa ggt ccg agc gtg ttt ccg ctg gca ccg            1665
Val Ser Ser Ala Ser Thr Lys Gly Pro Ser Val Phe Pro Leu Ala Pro
        475                 480                 485 agc agc aaa agc acc agc ggt ggc acc gca gca ctg ggt tgt ctg gtt            1713
Ser Ser Lys Ser Thr Ser Gly Gly Thr Ala Ala Leu Gly Cys Leu Val
490                 495                 500                 505 aaa gat tat ttt ccg gaa ccg gtt acc gtt agc tgg aat agc ggt gca            1761
Lys Asp Tyr Phe Pro Glu Pro Val Thr Val Ser Trp Asn Ser Gly Ala
                510                 515                 520 ctg acc agc ggt gtt cat acc ttt ccg gca gtt ctg cag agc agc ggt            1809
Leu Thr Ser Gly Val His Thr Phe Pro Ala Val Leu Gln Ser Ser Gly
            525                 530                 535 ctg tat agc ctg agt agc gtt gtt acc gtt ccg agc agc agc ctg ggc            1857
Leu Tyr Ser Leu Ser Ser Val Val Thr Val Pro Ser Ser Ser Leu Gly
        540                 545                 550 acc cag acc tat att tgt aat gtt aat cat aaa ccg agc aat acc aaa            1905
Thr Gln Thr Tyr Ile Cys Asn Val Asn His Lys Pro Ser Asn Thr Lys
555                 560                 565 gtg gat aaa aaa gtt gag ccg aaa agc tgt ggt ggt cat cat cat cac            1953
Val Asp Lys Lys Val Glu Pro Lys Ser Cys Gly Gly His His His His
570                 575                 580                 585 cat cat ggt ggt ggg ggt ggt ggt agc tca tct agc ggt agc ggt                2001
His His Gly Gly Gly Gly Gly Gly Ser Ser Ser Ser Gly Ser Gly
                590                 595                 600 tct agc agc tct agc agt agc agc tct ggt tca agc tca agt agc tca            2049
Ser Ser Ser Ser Ser Ser Ser Ser Gly Ser Ser Ser Ser Ser
            605                 610                 615 agc tca agc tct agt agc agc ggc tcc ggt ggt ggc ggt tca ggt agc            2097
Ser Ser Ser Ser Ser Ser Gly Ser Gly Gly Gly Gly Ser Gly Ser
                620                 625                 630 tca tca ggc agc tca ggc ggt ggt agt ggc ggt ggt tca ggt tca ggt            2145
Ser Ser Gly Ser Ser Gly Gly Gly Ser Gly Gly Gly Ser Gly Ser Gly
        635                 640                 645 ggt agc tct ggt ggt ggc agc agt tca agc tca tct ggt tct agt tca            2193
Gly Ser Ser Gly Gly Gly Ser Ser Ser Ser Ser Ser Gly Ser Ser Ser
650                 655                 660                 665 ggt agc ggc agc gga ggt ggt ggc gga agc agc agt agt tca ggc ggt            2241
Gly Ser Gly Ser Gly Gly Gly Gly Gly Ser Ser Ser Ser Gly Gly
                670                 675                 680 ggc agc tct agc ggt ggt tca tca agc ggt ggc agt tcc ggt ggt ggt            2289
Gly Ser Ser Ser Gly Gly Ser Ser Ser Gly Gly Ser Ser Gly Gly Gly
            685                 690                 695 ggc tct agt ggt tca gca aaa ttt tca acc cct gtt tgg att tca cag            2337
Gly Ser Ser Gly Ser Ala Lys Phe Ser Thr Pro Val Trp Ile Ser Gln
                700                 705                 710 gcc cag ggc att cgc gca ggc cct ccg taatgaagcg gtagtgccgg                  2384
Ala Gln Gly Ile Arg Ala Gly Pro Pro
            715                 720 tgccggtgcg ggtggtagca aagatattcg tccattcgtt tgtgaatatc aaggccaatc         2444
gtctgacctg ccgcacacct tactggtgtg cgg                                       2477
```

```
<210> SEQ ID NO 14
<211> LENGTH: 355
<212> TYPE: PRT
<213> ORGANISM: Artificial sequence
<220> FEATURE:
<223> OTHER INFORMATION: Synthetic Construct

<400> SEQUENCE: 14

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Asp Tyr Lys Asp Asp Asp Asp
    210                 215                 220

Lys Ser Gly Ser Ser Gly Ser Gly Ser Ser Ser Ser Gly Ser
225                 230                 235                 240

Ser Gly Gly Gly Ser Ser Ser Gly Ser Gly Gly Ser Ser
                245                 250                 255

Ser Gly Gly Gly Ser Ser Gly Ser Ser Gly Ser Ser Ser Gly
            260                 265                 270

Ser Gly Ser Ser Gly Ser Gly Ser Ser Ser Gly Gly Gly Gly
        275                 280                 285

Ser Ser Ser Gly Ser Ser Ser Gly Gly Gly Gly Ser Ser
    290                 295                 300

Gly Ser Ser Ser Gly Ser Gly Gly Gly Ser Ser Gly Ser Ser Gly
305                 310                 315                 320

Gly Ser Ser Ser Ser Ser Ser Ser Ser Ser Gly Gly Ser Gly Ala
                325                 330                 335

Lys Phe Ser Thr Pro Val Trp Ile Ser Gln Ala Gln Gly Ile Arg Ala
            340                 345                 350

Gly Pro Pro
        355
```

```
<210> SEQ ID NO 15
<211> LENGTH: 367
<212> TYPE: PRT
<213> ORGANISM: Artificial sequence
<220> FEATURE:
<223> OTHER INFORMATION: Synthetic Construct

<400> SEQUENCE: 15

Met Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys Asp
                20                  25                  30

Thr Tyr Ile His Trp Val Arg Gln Ala Pro Gly Lys Gly Leu Glu Trp
            35                  40                  45

Val Ala Arg Ile Tyr Pro Thr Asn Gly Tyr Thr Arg Tyr Ala Asp Ser
        50                  55                  60

Val Lys Gly Arg Phe Thr Ile Ser Ala Asp Thr Ser Lys Asn Thr Ala
 65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Gly Gly His His His His His His Gly Gly Gly Gly Gly Gly Gly Ser
225                 230                 235                 240

Ser Ser Ser Gly Ser Gly Ser Ser Ser Ser Ser Ser Ser Ser Ser Gly
                245                 250                 255

Ser Ser Ser Ser Ser Ser Ser Ser Ser Ser Ser Ser Gly Ser Ser Gly
            260                 265                 270

Gly Gly Gly Ser Gly Ser Ser Gly Ser Ser Gly Gly Gly Ser Gly Ser
        275                 280                 285

Gly Gly Ser Gly Ser Gly Gly Ser Ser Gly Gly Gly Ser Ser Ser Ser
290                 295                 300

Ser Ser Gly Ser Ser Ser Gly Ser Gly Ser Gly Gly Gly Gly Gly Ser
305                 310                 315                 320

Ser Ser Ser Ser Gly Gly Gly Ser Ser Ser Gly Gly Ser Ser Ser Gly
                325                 330                 335

Gly Ser Ser Gly Gly Gly Gly Ser Ser Gly Ser Ala Lys Phe Ser Thr
            340                 345                 350

Pro Val Trp Ile Ser Gln Ala Gln Gly Ile Arg Ala Gly Pro Pro
        355                 360                 365
```

-continued

```
<210> SEQ ID NO 16
<211> LENGTH: 2483
<212> TYPE: DNA
<213> ORGANISM: Artificial sequence
<220> FEATURE:
<223> OTHER INFORMATION: pGAv2 Fab-TT
<220> FEATURE:
<221> NAME/KEY: CDS
<222> LOCATION: (94)..(1158)
<220> FEATURE:
<221> NAME/KEY: CDS
<222> LOCATION: (1264)..(2370)

<400> SEQUENCE: 16
```

| | | | | | | | | | | | | | | | | |
|---|---|---|---|---|---|---|---|---|---|---|---|---|---|---|---|---|
| aatttcggta | atacgactca | ctatagggag | accacaacgg | tttcccattt | aggtgacact | | | | | | | | | | | 60 |
| atagaagtgt | aactttaaga | aggagatata | cca atg gat att cag atg acc cag | | | | | | | | | | | | | 114 |
| | | | | Met Asp Ile Gln Met Thr Gln | | | | | | | | | | | | |
| | | | | 1               5 | | | | | | | | | | | | |

```
agc ccg agc agc ctg agc gca agc gtt ggt gat cgt gtt acc att acc       162
Ser Pro Ser Ser Leu Ser Ala Ser Val Gly Asp Arg Val Thr Ile Thr
         10                  15                  20 tgt cgt gca agc cag gat att aaa aat tat ttg tct tgg tat caa caa       210
Cys Arg Ala Ser Gln Asp Ile Lys Asn Tyr Leu Ser Trp Tyr Gln Gln
 25                  30                  35 caa cca gga aat gcc ccg aag cca ctg att tat gct ggt tct aac cgc       258
Gln Pro Gly Asn Ala Pro Lys Pro Leu Ile Tyr Ala Gly Ser Asn Arg
 40                  45                  50                  55 caa tct gga gtt cct tct cgc ttc tcc gga tct gga tct gaa act gat       306
Gln Ser Gly Val Pro Ser Arg Phe Ser Gly Ser Gly Ser Glu Thr Asp
                 60                  65                  70 ttt act cta act att agt agt cta cag ccg gag gac ttc gcc acc tat       354
Phe Thr Leu Thr Ile Ser Ser Leu Gln Pro Glu Asp Phe Ala Thr Tyr
         75                  80                  85 tat tgc caa caa act tac atc tac cct atc acc ttt ggc cag ggc acc       402
Tyr Cys Gln Gln Thr Tyr Ile Tyr Pro Ile Thr Phe Gly Gln Gly Thr
 90                  95                 100 aaa gtt gaa att aaa cgt acc gtt gca gca ccg agc gtt ttt att ttt       450
Lys Val Glu Ile Lys Arg Thr Val Ala Ala Pro Ser Val Phe Ile Phe
105                 110                 115 ccg cct agt gat gaa cag ctg aaa agc ggc acc gca agc gtt gtt tgt       498
Pro Pro Ser Asp Glu Gln Leu Lys Ser Gly Thr Ala Ser Val Val Cys
120                 125                 130                 135 ctg ctg aat aat ttt tat ccg cgt gaa gca aaa gtg cag tgg aaa gtt       546
Leu Leu Asn Asn Phe Tyr Pro Arg Glu Ala Lys Val Gln Trp Lys Val
                140                 145                 150 gat aat gca ctg cag agc ggt aat agc caa gaa agc gtt acc gaa cag       594
Asp Asn Ala Leu Gln Ser Gly Asn Ser Gln Glu Ser Val Thr Glu Gln
        155                 160                 165 gat agc aaa gat agc acc tat agc ctg agc agc acc ctg acc ctg agc       642
Asp Ser Lys Asp Ser Thr Tyr Ser Leu Ser Ser Thr Leu Thr Leu Ser
170                 175                 180 aaa gca gat tat gaa aaa cac aaa gtg tat gcc tgc gaa gtt acc cat       690
Lys Ala Asp Tyr Glu Lys His Lys Val Tyr Ala Cys Glu Val Thr His
185                 190                 195 cag ggt ctg agc agt ccg gtt acc aaa agc ttt aat cgt ggt gaa tgc       738
Gln Gly Leu Ser Ser Pro Val Thr Lys Ser Phe Asn Arg Gly Glu Cys
200                 205                 210                 215 ggt ggc gat tat aaa gat gat gat gat aaa agc ggt agc agc ggt agt       786
Gly Gly Asp Tyr Lys Asp Asp Asp Asp Lys Ser Gly Ser Ser Gly Ser
                220                 225                 230 ggt agc ggt agc agt agt agc ggt tca agc ggt ggt ggt agc agc agc       834
```

```
Gly Ser Gly Ser Ser Ser Ser Gly Ser Ser Gly Gly Ser Ser Ser
            235                 240                 245 tca ggt agt ggt ggt ggt ggt tca agc agc ggt ggt ggc agt agc ggt            882
Ser Gly Ser Gly Gly Gly Gly Ser Ser Ser Gly Gly Gly Ser Ser Gly
            250                 255                 260 agc tca agc ggt agc tct agc agc ggt tct ggt agc agt ggt tca ggt            930
Ser Ser Ser Gly Ser Ser Ser Ser Gly Ser Gly Ser Ser Gly Ser Gly
        265                 270                 275 agt agc agc agc ggt ggc ggt ggt ggc tca agt agt ggt agc agc tca            978
Ser Ser Ser Ser Gly Gly Gly Gly Gly Ser Ser Ser Gly Ser Ser Ser
    280                 285                 290                 295 tca ggt ggc ggt ggc ggt agt agc tct ggt agc tca agt ggt tct ggt           1026
Ser Gly Gly Gly Gly Gly Ser Ser Ser Gly Ser Ser Ser Gly Ser Gly
            300                 305                 310 ggt ggt agt tct agc ggt agt agt ggt ggt tct agc tca agc agc agc           1074
Gly Gly Ser Ser Ser Gly Ser Ser Gly Gly Ser Ser Ser Ser Ser
            315                 320                 325 agc agt agc agt ggt ggt agc ggt gca aaa ttt agc aca ccg gtt tgg           1122
Ser Ser Ser Ser Gly Gly Ser Gly Ala Lys Phe Ser Thr Pro Val Trp
        330                 335                 340 att agc cag gca cag ggt att cgt gca ggt ccg cct taatgaggcg               1168
Ile Ser Gln Ala Gln Gly Ile Arg Ala Gly Pro Pro
        345                 350             355 gattgaatga gcataaatta ttcgagatcg atctcgatcc cgcgaaatgc ccctctagaa         1228
ataattttgt ttaactttaa gaaggagata tacat atg gaa gtt cag ctg gtt           1281
                                      Met Glu Val Gln Leu Val
                                                          360 gaa tca ggt ggt ggt ctg gtt cag cct ggt ggt agc ctg cgt ctg agc           1329
Glu Ser Gly Gly Gly Leu Val Gln Pro Gly Gly Ser Leu Arg Leu Ser
            365                 370                 375 tgt gca gca agc ggt ttt act att gaa cgt tat gcg atg ggt tgg gtg           1377
Cys Ala Ala Ser Gly Phe Thr Ile Glu Arg Tyr Ala Met Gly Trp Val
        380                 385                 390 cgt cag gct cct ggt aag ggc ctg gaa tgg gtt ggt acg att tat cct           1425
Arg Gln Ala Pro Gly Lys Gly Leu Glu Trp Val Gly Thr Ile Tyr Pro
    395                 400                 405 tgg ggc gat tat act gat tat gcc gat agc gtc aag ggt cgt ttt act           1473
Trp Gly Asp Tyr Thr Asp Tyr Ala Asp Ser Val Lys Gly Arg Phe Thr
410                 415                 420                 425 ata agt aga gat aat tct aaa aac acc ctc tac ctg cag atg aac agt           1521
Ile Ser Arg Asp Asn Ser Lys Asn Thr Leu Tyr Leu Gln Met Asn Ser
            430                 435                 440 cta aga gat gaa gat act gcc gtc tac tac tgc gct cgc tct aac tac           1569
Leu Arg Asp Glu Asp Thr Ala Val Tyr Tyr Cys Ala Arg Ser Asn Tyr
        445                 450                 455 ccg aac ggt atg tac tac gtt atg gaa tat tgg ggt cag ggc acc ctg           1617
Pro Asn Gly Met Tyr Tyr Val Met Glu Tyr Trp Gly Gln Gly Thr Leu
    460                 465                 470 gtt acc gtg agc agc gca agc acc aaa ggt ccg agc gtg ttt ccg ctg           1665
Val Thr Val Ser Ser Ala Ser Thr Lys Gly Pro Ser Val Phe Pro Leu
475                 480                 485 gca ccg agc agc aaa agc acc agc ggt ggc acc gca gca ctg ggt tgt           1713
Ala Pro Ser Ser Lys Ser Thr Ser Gly Gly Thr Ala Ala Leu Gly Cys
490                 495                 500                 505 ctg gtt aaa gat tat ttt ccg gaa ccg gtt acc gtt agc tgg aat agc           1761
Leu Val Lys Asp Tyr Phe Pro Glu Pro Val Thr Val Ser Trp Asn Ser
            510                 515                 520 ggt gca ctg acc agc ggt gtt cat acc ttt ccg gca gtt ctg cag agc           1809
Gly Ala Leu Thr Ser Gly Val His Thr Phe Pro Ala Val Leu Gln Ser
```

```
                          525                 530                 535
agc ggt ctg tat agc ctg agt agc gtt gtt acc gtt ccg agc agc agc    1857
Ser Gly Leu Tyr Ser Leu Ser Ser Val Val Thr Val Pro Ser Ser Ser
            540                 545                 550 ctg ggc acc cag acc tat att tgt aat gtt aat cat aaa ccg agc aat    1905
Leu Gly Thr Gln Thr Tyr Ile Cys Asn Val Asn His Lys Pro Ser Asn
555                 560                 565 acc aaa gtg gat aaa aaa gtt gag ccg aaa agc tgt ggt ggt cat cat    1953
Thr Lys Val Asp Lys Lys Val Glu Pro Lys Ser Cys Gly Gly His His
570                 575                 580                 585 cat cac cat cat ggt ggt ggg ggt ggt ggt ggt agc tca tct agc ggt    2001
His His His His Gly Gly Gly Gly Gly Gly Gly Ser Ser Ser Ser Gly
                590                 595                 600 agc ggt tct agc agc tct agc agt agc agc tct ggt tca agc tca agt    2049
Ser Gly Ser Ser Ser Ser Ser Ser Ser Ser Ser Gly Ser Ser Ser Ser
            605                 610                 615 agc tca agc tca agc tct agt agc agc ggc tcc ggt ggt ggc ggt tca    2097
Ser Ser Ser Ser Ser Ser Ser Ser Ser Gly Ser Gly Gly Gly Gly Ser
            620                 625                 630 ggt agc tca tca ggc agc tca ggc ggt ggt agt ggc ggt ggt tca ggt    2145
Gly Ser Ser Ser Gly Ser Ser Gly Gly Gly Ser Gly Gly Gly Ser Gly
635                 640                 645 tca ggt ggt agc tct ggt ggt ggc agc agt tca agc tca tct ggt tct    2193
Ser Gly Gly Ser Ser Gly Gly Gly Ser Ser Ser Ser Ser Ser Gly Ser
650                 655                 660                 665 agt tca ggt agc ggc agc gga ggt ggt ggc gga agc agc agt agt tca    2241
Ser Ser Gly Ser Gly Ser Gly Gly Gly Gly Gly Ser Ser Ser Ser Ser
                670                 675                 680 ggc ggt ggc agc tct agc ggt ggt tca tca agc ggt ggc agt tcc ggt    2289
Gly Gly Gly Ser Ser Ser Gly Gly Ser Ser Ser Gly Gly Ser Ser Gly
            685                 690                 695 ggt ggt ggc tct agt ggt tca gca aaa ttt tca acc cct gtt tgg att    2337
Gly Gly Gly Ser Ser Gly Ser Ala Lys Phe Ser Thr Pro Val Trp Ile
            700                 705                 710 tca cag gcc cag ggc att cgc gca ggc cct ccg taatgaagcg gtagtgccgg    2390
Ser Gln Ala Gln Gly Ile Arg Ala Gly Pro Pro
    715                 720 tgccggtgcg ggtggtagca agatattcg tccattcgtt tgtgaatatc aaggccaatc      2450
gtctgacctg ccgcacacct tactggtgtg cgg                                  2483

<210> SEQ ID NO 17
<211> LENGTH: 355
<212> TYPE: PRT
<213> ORGANISM: Artificial sequence
<220> FEATURE:
<223> OTHER INFORMATION: Synthetic Construct

<400> SEQUENCE: 17

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Lys Asn
            20                  25                  30

Tyr Leu Ser Trp Tyr Gln Gln Pro Gly Asn Ala Pro Lys Pro Leu
        35                  40                  45

Ile Tyr Ala Gly Ser Asn Arg Gln Ser Gly Val Pro Ser Arg Phe Ser
    50                  55                  60

Gly Ser Gly Ser Glu Thr Asp Phe Thr Leu Thr Ile Ser Ser Leu Gln
65                  70                  75                  80
```

```
Pro Glu Asp Phe Ala Thr Tyr Tyr Cys Gln Gln Thr Tyr Ile Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Asp Tyr Lys Asp Asp Asp Asp
            210                 215                 220

Lys Ser Gly Ser Ser Gly Ser Gly Ser Ser Ser Ser Gly Ser
225                 230                 235                 240

Ser Gly Gly Gly Ser Ser Ser Gly Ser Gly Gly Gly Ser Ser
            245                 250                 255

Ser Gly Gly Gly Ser Ser Gly Ser Ser Ser Gly Ser Ser Ser Gly
            260                 265                 270

Ser Gly Ser Ser Gly Ser Gly Ser Ser Ser Gly Gly Gly Gly
            275                 280                 285

Ser Ser Ser Gly Ser Ser Ser Gly Gly Gly Gly Ser Ser
290                 295                 300

Gly Ser Ser Ser Gly Ser Gly Gly Gly Ser Ser Gly Ser Ser Gly
305                 310                 315                 320

Gly Ser Ser Ser Ser Ser Ser Ser Ser Gly Gly Ser Gly Ala
            325                 330                 335

Lys Phe Ser Thr Pro Val Trp Ile Ser Gln Ala Gln Gly Ile Arg Ala
            340                 345                 350

Gly Pro Pro
        355

<210> SEQ ID NO 18
<211> LENGTH: 369
<212> TYPE: PRT
<213> ORGANISM: Artificial sequence
<220> FEATURE:
<223> OTHER INFORMATION: Synthetic Construct

<400> SEQUENCE: 18

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Ile Glu Arg
            20                  25                  30

Tyr Ala Met Gly Trp Val Arg Gln Ala Pro Lys Gly Leu Glu Trp
            35                  40                  45

Val Gly Thr Ile Tyr Pro Trp Gly Asp Tyr Thr Asp Tyr Ala Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Asp Glu Asp Thr Ala Val Tyr Tyr
                85                  90                  95

Cys Ala Arg Ser Asn Tyr Pro Asn Gly Met Tyr Val Met Glu Tyr
        100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Gly Gly His His His His His Gly Gly Gly Gly Gly Gly Gly
225                 230                 235                 240

Gly Ser Ser Ser Gly Ser Gly Ser Ser Ser Ser Ser Ser Ser
                245                 250                 255

Ser Gly Ser Ser Ser Ser Ser Ser Ser Ser Ser Ser Ser Gly
            260                 265                 270

Ser Gly Gly Gly Ser Gly Ser Ser Gly Ser Gly Gly Gly
        275                 280                 285

Ser Gly Gly Gly Ser Gly Ser Gly Gly Ser Ser Gly Gly Gly Ser Ser
290                 295                 300

Ser Ser Ser Ser Gly Ser Ser Ser Gly Ser Gly Ser Gly Gly Gly Gly
305                 310                 315                 320

Gly Ser Ser Ser Ser Gly Gly Gly Ser Ser Ser Gly Gly Ser Ser
                325                 330                 335

Ser Gly Gly Ser Ser Gly Gly Gly Gly Ser Ser Gly Ser Ala Lys Phe
            340                 345                 350

Ser Thr Pro Val Trp Ile Ser Gln Ala Gln Gly Ile Arg Ala Gly Pro
        355                 360                 365

Pro
```

```
<210> SEQ ID NO 19
<211> LENGTH: 2333
<212> TYPE: DNA
<213> ORGANISM: Artificial sequence
<220> FEATURE:
<223> OTHER INFORMATION: pGAv6 Fab-HHxhoI
<220> FEATURE:
<221> NAME/KEY: CDS
<222> LOCATION: (94)..(2220)

<400> SEQUENCE: 19
aatttcggta atacgactca ctatagggag accacaacgg tttcccattt aggtgacact    60
atagaagtgt aactttaaga aggagatata cca atg gat att cag atg acc cag   114
                                    Met Asp Ile Gln Met Thr Gln
                                      1               5 agc ccg agc agc ctg agc gca agc gtt ggt gat cgt gtc acc atc acc   162
Ser Pro Ser Ser Leu Ser Ala Ser Val Gly Asp Arg Val Thr Ile Thr
         10                  15                  20
```

-continued

| | | |
|---|---|---|
| tgc cgt gcc agt cag gat gtg aac acc gcc gtt gca tgg tat caa caa<br>Cys Arg Ala Ser Gln Asp Val Asn Thr Ala Val Ala Trp Tyr Gln Gln<br>25                  30                  35 | 210 |
| aaa cca gga aaa gcc ccg aag ctg ctg att tat agc gcc tct ttt ctg<br>Lys Pro Gly Lys Ala Pro Lys Leu Leu Ile Tyr Ser Ala Ser Phe Leu<br>40                  45                  50                  55 | 258 |
| tat tct gga gtt cct tct cgc ttc tcc gga tcc cgt tct ggc act gat<br>Tyr Ser Gly Val Pro Ser Arg Phe Ser Gly Ser Arg Ser Gly Thr Asp<br>                  60                  65                  70 | 306 |
| ttt act cta act att agt agt cta cag ccg gag gac ttc gcc acc tat<br>Phe Thr Leu Thr Ile Ser Ser Leu Gln Pro Glu Asp Phe Ala Thr Tyr<br>                  75                  80                  85 | 354 |
| tat tgc caa caa cat tac acc acc cct ccg act ttc ggc cag ggt acc<br>Tyr Cys Gln Gln His Tyr Thr Thr Pro Pro Thr Phe Gly Gln Gly Thr<br>          90                  95                  100 | 402 |
| aag gtg gaa att aaa cgt acc gtt gca gca ccg agc gtt ttt att ttt<br>Lys Val Glu Ile Lys Arg Thr Val Ala Ala Pro Ser Val Phe Ile Phe<br>105                  110                  115 | 450 |
| ccg cct agt gat gaa cag ctg aaa agc ggc acc gca agc gtt gtt tgt<br>Pro Pro Ser Asp Glu Gln Leu Lys Ser Gly Thr Ala Ser Val Val Cys<br>120                  125                  130                  135 | 498 |
| ctg ctg aat aat ttt tat ccg cgt gaa gca aaa gtg cag tgg aaa gtt<br>Leu Leu Asn Asn Phe Tyr Pro Arg Glu Ala Lys Val Gln Trp Lys Val<br>                  140                  145                  150 | 546 |
| gat aat gca ctg cag agc ggt aat agc caa gaa agc gtt acc gaa cag<br>Asp Asn Ala Leu Gln Ser Gly Asn Ser Gln Glu Ser Val Thr Glu Gln<br>          155                  160                  165 | 594 |
| gat agc aaa gat agc acc tat agc ctg agc agc acc ctg acc ctg agc<br>Asp Ser Lys Asp Ser Thr Tyr Ser Leu Ser Ser Thr Leu Thr Leu Ser<br>170                  175                  180 | 642 |
| aaa gca gat tat gaa aaa cac aaa gtg tat gcc tgc gaa gtt acc cat<br>Lys Ala Asp Tyr Glu Lys His Lys Val Tyr Ala Cys Glu Val Thr His<br>185                  190                  195 | 690 |
| cag ggt ctg agc agt ccg gtt acc aaa agc ttt aat cgt ggt gaa tgc<br>Gln Gly Leu Ser Ser Pro Val Thr Lys Ser Phe Asn Arg Gly Glu Cys<br>200                  205                  210                  215 | 738 |
| ggt ggc gat tat aaa gat gat gat gat aaa agc ggt agc agc ggt agt<br>Gly Gly Asp Tyr Lys Asp Asp Asp Asp Lys Ser Gly Ser Ser Gly Ser<br>                  220                  225                  230 | 786 |
| ggt agc ggt agc agt agt agc ggt tca agc ggt ggt ggt agc agc agc<br>Gly Ser Gly Ser Ser Ser Ser Gly Ser Ser Gly Gly Gly Ser Ser Ser<br>          235                  240                  245 | 834 |
| tca ggt agt ggt ggt ggt ggt tca agc agc ggt ggt ggc agc agc ggt<br>Ser Gly Ser Gly Gly Gly Gly Ser Ser Ser Gly Gly Gly Ser Ser Gly<br>250                  255                  260 | 882 |
| agc tca agc ggt agc tct agc agc ggt tct ggt agc agt ggt tca ggt<br>Ser Ser Ser Gly Ser Ser Ser Ser Gly Ser Gly Ser Ser Gly Ser Gly<br>265                  270                  275 | 930 |
| agt agc agc agc ggt ggc ggt ggt tca agt agt ggt agc agc tca<br>Ser Ser Ser Ser Gly Gly Gly Gly Ser Ser Ser Gly Ser Ser Ser<br>280                  285                  290                  295 | 978 |
| tca ggt ggc ggt ggc ggt agt agc tct ggt agc tca agt ggt tct ggt<br>Ser Gly Gly Gly Gly Gly Ser Ser Ser Gly Ser Ser Ser Gly Ser Gly<br>                  300                  305                  310 | 1026 |
| ggt ggt agt tct agc ggt agt agt ggt ggt tct agc tca agc agc agc<br>Gly Gly Ser Ser Ser Gly Ser Ser Gly Gly Ser Ser Ser Ser Ser Ser<br>                  315                  320                  325 | 1074 |
| agc tcc tcg agc ggt ggc agc ggt gat tat aag gac gac gat gat aag<br>Ser Ser Ser Ser Gly Gly Ser Gly Asp Tyr Lys Asp Asp Asp Asp Lys<br>330                  335                  340 | 1122 |

-continued

```
gaa gtt cag ctg gtt gaa tca ggt ggt ggt ctg gtt cag cct gga ggc       1170
Glu Val Gln Leu Val Glu Ser Gly Gly Gly Leu Val Gln Pro Gly Gly
345                 350                 355 tca ctc cgt ttg tcc tgc gca gca tcc gga ttt aac att aaa gat acc       1218
Ser Leu Arg Leu Ser Cys Ala Ala Ser Gly Phe Asn Ile Lys Asp Thr
360                 365                 370                 375 tat atc cac tgg gtg cgt cag gct cct ggt aag ggc ctg gaa tgg gtt       1266
Tyr Ile His Trp Val Arg Gln Ala Pro Gly Lys Gly Leu Glu Trp Val
                380                 385                 390 gcc cgt att tat cct acc aac ggc tat act cgt tat gcc gat agc gtc       1314
Ala Arg Ile Tyr Pro Thr Asn Gly Tyr Thr Arg Tyr Ala Asp Ser Val
395                 400                 405 aag ggt cgt ttt act ata agt gcg gat acc tct aaa aac acc gcg tac       1362
Lys Gly Arg Phe Thr Ile Ser Ala Asp Thr Ser Lys Asn Thr Ala Tyr
410                 415                 420 ctg cag atg aac agt cta aga gcg gaa gat act gcc gtc tac tac tgc       1410
Leu Gln Met Asn Ser Leu Arg Ala Glu Asp Thr Ala Val Tyr Tyr Cys
425                 430                 435 agc cgc tgg ggc ggc gat ggc ttt tac gcg atg gat tac tgg ggc cag       1458
Ser Arg Trp Gly Gly Asp Gly Phe Tyr Ala Met Asp Tyr Trp Gly Gln
440                 445                 450                 455 gga act ttg gtt act gtt tcc agc gca agc acc aaa ggt ccg agc gtg       1506
Gly Thr Leu Val Thr Val Ser Ser Ala Ser Thr Lys Gly Pro Ser Val
                460                 465                 470 ttt ccg ctg gca ccg agc agc aaa agc acc agc ggt ggc acc gca gca       1554
Phe Pro Leu Ala Pro Ser Ser Lys Ser Thr Ser Gly Gly Thr Ala Ala
                475                 480                 485 ctg ggt tgt ctg gtt aaa gat tat ttt ccg gaa ccg gtt acc gtt agc       1602
Leu Gly Cys Leu Val Lys Asp Tyr Phe Pro Glu Pro Val Thr Val Ser
            490                 495                 500 tgg aat agc ggt gca ctg acc agc ggt gtt cat acc ttt ccg gca gtt       1650
Trp Asn Ser Gly Ala Leu Thr Ser Gly Val His Thr Phe Pro Ala Val
            505                 510                 515 ctg cag agc agc ggt ctg tat agc ctg agt agc gtt gtt acc gtt ccg       1698
Leu Gln Ser Ser Gly Leu Tyr Ser Leu Ser Ser Val Val Thr Val Pro
520                 525                 530                 535 agc agc agc ctg ggc acc cag acc tat att tgt aat gtt aat cat aaa       1746
Ser Ser Ser Leu Gly Thr Gln Thr Tyr Ile Cys Asn Val Asn His Lys
                540                 545                 550 ccg agc aat acc aaa gtg gat aaa aaa gtt gag ccg aaa agc tgt ggt       1794
Pro Ser Asn Thr Lys Val Asp Lys Lys Val Glu Pro Lys Ser Cys Gly
                555                 560                 565 ggt cat cat cat cac cat cat ggt ggt ggg ggt ggt ggt ggc agc tca       1842
Gly His His His His His His Gly Gly Gly Gly Gly Gly Gly Ser Ser
            570                 575                 580 tct agc ggt agc ggt tct agc agc tct agc agt agc agc tct ggt tca       1890
Ser Ser Gly Ser Gly Ser Ser Ser Ser Ser Ser Ser Ser Ser Gly Ser
585                 590                 595 agc tca agt agc tca agc tca agc tct agt agc agc ggc tcc ggt ggt       1938
Ser Ser Ser Ser Ser Ser Ser Ser Ser Ser Ser Ser Gly Ser Gly Gly
600                 605                 610                 615 ggc ggt tca ggt agc tca tca ggc agc tca ggc ggt agt ggc ggt           1986
Gly Gly Ser Gly Ser Ser Gly Ser Ser Gly Gly Ser Gly Gly
                620                 625                 630 ggt tca ggt tca ggt ggt agc tct ggt ggt ggc agc agt tca agc tca       2034
Gly Ser Gly Ser Gly Gly Ser Ser Gly Gly Gly Ser Ser Ser Ser Ser
                635                 640                 645 tct ggt tct agt tca ggt agc ggc agc gga ggt ggt ggc gga agc agc       2082
Ser Gly Ser Ser Ser Gly Ser Gly Ser Gly Gly Gly Gly Gly Ser Ser
```

|     |     |     |     | 650 |     |     |     | 655 |     |     |     | 660 |     |     |     |      |
| --- | --- | --- | --- | --- | --- | --- | --- | --- | --- | --- | --- | --- | --- | --- | --- | ---- |
| agt | agt | tca | ggc | ggt | ggc | agc | tct | agc | ggt | ggt | tca | tca | agc | ggt | ggc | 2130 |
| Ser | Ser | Ser | Gly | Gly | Gly | Ser | Ser | Ser | Gly | Gly | Ser | Ser | Ser | Gly | Gly |      |
|     |     | 665 |     |     |     |     | 670 |     |     |     |     | 675 |     |     |     |      |
| agt | tcc | ggt | ggt | ggt | ggc | tct | agt | ggt | tca | gca | aaa | ttt | tca | acc | cct | 2178 |
| Ser | Ser | Gly | Gly | Gly | Gly | Ser | Ser | Gly | Ser | Ala | Lys | Phe | Ser | Thr | Pro |      |
| 680 |     |     |     |     | 685 |     |     |     |     | 690 |     |     |     |     | 695 |      |
| gtt | tgg | att | tca | cag | gcc | cag | ggc | att | cgc | gca | ggc | cct | ccg |     |     | 2220 |
| Val | Trp | Ile | Ser | Gln | Ala | Gln | Gly | Ile | Arg | Ala | Gly | Pro | Pro |     |     |      |
|     |     |     |     | 700 |     |     |     |     | 705 |     |     |     |     |     |     |      | taatgaagcg gtagtgccgg tgccggtgcg ggtggtagca agatattcg tccattcgtt 2280 tgtgaatatc aaggccaatc gtctgacctg ccgcacacct tactggtgtg cgg 2333

<210> SEQ ID NO 20
<211> LENGTH: 709
<212> TYPE: PRT
<213> ORGANISM: Artificial sequence
<220> FEATURE:
<223> OTHER INFORMATION: Synthetic Construct

<400> SEQUENCE: 20

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Asp Tyr Lys Asp Asp Asp Asp
    210                 215                 220

Lys Ser Gly Ser Gly Ser Gly Ser Gly Ser Ser Ser Ser Gly Ser
225                 230                 235                 240

Ser Gly Gly Gly Ser Ser Ser Gly Ser Gly Gly Gly Ser Ser
            245                 250                 255

Ser Gly Gly Gly Ser Ser Gly Ser Ser Ser Gly Ser Ser Ser Gly
        260                 265                 270

-continued

```
Ser Gly Ser Ser Gly Ser Gly Ser Ser Ser Gly Gly Gly Gly
            275                 280             285

Ser Ser Ser Gly Ser Ser Ser Gly Gly Gly Gly Ser Ser Ser
            290                 295             300

Gly Ser Ser Ser Gly Ser Gly Gly Gly Ser Ser Gly Ser Ser Gly
305             310                 315                 320

Gly Ser Ser Ser Ser Ser Ser Ser Ser Ser Gly Gly Ser Gly Asp
                325                 330                 335

Tyr Lys Asp Asp Asp Lys Glu Val Gln Leu Val Glu Ser Gly Gly
            340                 345                 350

Gly Leu Val Gln Pro Gly Gly Ser Leu Arg Leu Ser Cys Ala Ala Ser
    355                 360                 365

Gly Phe Asn Ile Lys Asp Thr Tyr Ile His Trp Val Arg Gln Ala Pro
    370                 375                 380

Gly Lys Gly Leu Glu Trp Val Ala Arg Ile Tyr Pro Thr Asn Gly Tyr
385                 390                 395                 400

Thr Arg Tyr Ala Asp Ser Val Lys Gly Arg Phe Thr Ile Ser Ala Asp
                405                 410                 415

Thr Ser Lys Asn Thr Ala Tyr Leu Gln Met Asn Ser Leu Arg Ala Glu
            420                 425                 430

Asp Thr Ala Val Tyr Tyr Cys Ser Arg Trp Gly Gly Asp Gly Phe Tyr
            435                 440                 445

Ala Met Asp Tyr Trp Gly Gln Gly Thr Leu Val Thr Val Ser Ser Ala
    450                 455                 460

Ser Thr Lys Gly Pro Ser Val Phe Pro Leu Ala Pro Ser Ser Lys Ser
465                 470                 475                 480

Thr Ser Gly Gly Thr Ala Ala Leu Gly Cys Leu Val Lys Asp Tyr Phe
                485                 490                 495

Pro Glu Pro Val Thr Val Ser Trp Asn Ser Gly Ala Leu Thr Ser Gly
            500                 505                 510

Val His Thr Phe Pro Ala Val Leu Gln Ser Ser Gly Leu Tyr Ser Leu
            515                 520                 525

Ser Ser Val Val Thr Val Pro Ser Ser Ser Leu Gly Thr Gln Thr Tyr
            530                 535                 540

Ile Cys Asn Val Asn His Lys Pro Ser Asn Thr Lys Val Asp Lys Lys
545                 550                 555                 560

Val Glu Pro Lys Ser Cys Gly Gly His His His His His His Gly Gly
                565                 570                 575

Gly Gly Gly Gly Gly Ser Ser Ser Gly Ser Gly Ser Ser Ser
            580                 585                 590

Ser Ser Ser Ser Ser Gly Ser Ser Ser Ser Ser Ser Ser Ser
            595                 600                 605

Ser Ser Ser Gly Ser Gly Gly Gly Ser Gly Ser Ser Gly Ser
    610                 615                 620

Ser Gly Gly Gly Ser Gly Gly Ser Gly Gly Ser Ser Gly
625                 630                 635                 640

Gly Gly Ser Ser Ser Ser Ser Gly Ser Ser Gly Ser Gly Ser
                645                 650                 655

Gly Gly Gly Gly Ser Ser Ser Ser Gly Gly Ser Ser Ser
                660                 665                 670

Gly Gly Ser Ser Ser Gly Gly Ser Ser Gly Gly Gly Ser Ser Gly
            675                 680                 685

Ser Ala Lys Phe Ser Thr Pro Val Trp Ile Ser Gln Ala Gln Gly Ile
```

```
                   690                695                700
Arg Ala Gly Pro Pro
705

<210> SEQ ID NO 21
<211> LENGTH: 2339
<212> TYPE: DNA
<213> ORGANISM: Artificial sequence
<220> FEATURE:
<223> OTHER INFORMATION: pGAv6 Fab-TT
<220> FEATURE:
<221> NAME/KEY: CDS
<222> LOCATION: (94)..(2226)

<400> SEQUENCE: 21
aatttcggta atacgactca ctataggag accacaacgg tttcccattt aggtgacact        60
atagaagtgt aactttaaga aggagatata cca atg gat att cag atg acc cag      114
                                    Met Asp Ile Gln Met Thr Gln
                                      1               5 agc ccg agc agc ctg agc gca agc gtt ggt gat cgt gtt acc att acc      162
Ser Pro Ser Ser Leu Ser Ala Ser Val Gly Asp Arg Val Thr Ile Thr
         10                  15                  20 tgt cgt gca agc cag gat att aaa aat tat ttg tct tgg tat caa caa      210
Cys Arg Ala Ser Gln Asp Ile Lys Asn Tyr Leu Ser Trp Tyr Gln Gln
 25                  30                  35 caa cca gga aat gcc ccg aag cca ctg att tat gct ggt tct aac cgc      258
Gln Pro Gly Asn Ala Pro Lys Pro Leu Ile Tyr Ala Gly Ser Asn Arg
 40                  45                  50                  55 caa tct gga gtt cct tct cgc ttc tcc gga tct gga tct gaa act gat      306
Gln Ser Gly Val Pro Ser Arg Phe Ser Gly Ser Gly Ser Glu Thr Asp
                 60                  65                  70 ttt act cta act att agt agt cta cag ccg gag gac ttc gcc acc tat      354
Phe Thr Leu Thr Ile Ser Ser Leu Gln Pro Glu Asp Phe Ala Thr Tyr
             75                  80                  85 tat tgc caa caa act tac atc tac cct atc acc ttt ggc cag ggc acc      402
Tyr Cys Gln Gln Thr Tyr Ile Tyr Pro Ile Thr Phe Gly Gln Gly Thr
         90                  95                 100 aaa gtt gaa att aaa cgt acc gtt gca gca ccg agc gtt ttt att ttt      450
Lys Val Glu Ile Lys Arg Thr Val Ala Ala Pro Ser Val Phe Ile Phe
105                 110                 115 ccg cct agt gat gaa cag ctg aaa agc ggc acc gca agc gtt gtt tgt      498
Pro Pro Ser Asp Glu Gln Leu Lys Ser Gly Thr Ala Ser Val Val Cys
120                 125                 130                 135 ctg ctg aat aat ttt tat ccg cgt gaa gca aaa gtg cag tgg aaa gtt      546
Leu Leu Asn Asn Phe Tyr Pro Arg Glu Ala Lys Val Gln Trp Lys Val
                140                 145                 150 gat aat gca ctg cag agc ggt aat agc caa gaa agc gtt acc gaa cag      594
Asp Asn Ala Leu Gln Ser Gly Asn Ser Gln Glu Ser Val Thr Glu Gln
            155                 160                 165 gat agc aaa gat agc acc tat agc ctg agc agc acc ctg acc ctg agc      642
Asp Ser Lys Asp Ser Thr Tyr Ser Leu Ser Ser Thr Leu Thr Leu Ser
        170                 175                 180 aaa gca gat tat gaa aaa cac aaa gtg tat gcc tgc gaa gtt acc cat      690
Lys Ala Asp Tyr Glu Lys His Lys Val Tyr Ala Cys Glu Val Thr His
185                 190                 195 cag ggt ctg agc agt ccg gtt acc aaa agc ttt aat cgt ggt gaa tgc      738
Gln Gly Leu Ser Ser Pro Val Thr Lys Ser Phe Asn Arg Gly Glu Cys
200                 205                 210                 215 ggt ggc gat tat aaa gat gat gat gat aaa agc ggt agc agc ggt agt      786
Gly Gly Asp Tyr Lys Asp Asp Asp Asp Lys Ser Gly Ser Ser Gly Ser
                220                 225                 230
```

| | | |
|---|---|---|
| ggt agc ggt agc agt agt agc ggt tca agc ggt ggt ggt agc agc agc<br>Gly Ser Gly Ser Ser Ser Ser Gly Ser Ser Gly Gly Gly Ser Ser Ser<br>235 240 245 | | 834 |
| tca ggt agt ggt ggt ggt ggt tca agc agc ggt ggt ggc agt agc ggt<br>Ser Gly Ser Gly Gly Gly Gly Ser Ser Ser Gly Gly Gly Ser Ser Gly<br>250 255 260 | | 882 |
| agc tca agc ggt agc tct agc agc ggt tct ggt agc agt ggt tca ggt<br>Ser Ser Ser Gly Ser Ser Ser Ser Gly Ser Gly Ser Ser Gly Ser Gly<br>265 270 275 | | 930 |
| agt agc agc agc ggt ggc ggt ggt ggc tca agt agt ggt agc agc tca<br>Ser Ser Ser Ser Gly Gly Gly Gly Gly Ser Ser Ser Gly Ser Ser Ser<br>280 285 290 295 | | 978 |
| tca ggt ggt ggt ggc ggt agt agc tct ggt agc tca agt ggt tct ggt<br>Ser Gly Gly Gly Gly Gly Ser Ser Ser Gly Ser Ser Ser Gly Ser Gly<br>300 305 310 | | 1026 |
| ggt ggt agt tct agc ggt agt agt ggt ggt tct agc tca agc agc agc<br>Gly Gly Ser Ser Ser Gly Ser Ser Gly Gly Ser Ser Ser Ser Ser Ser<br>315 320 325 | | 1074 |
| agc agt agc agt ggt ggt agc ggt gat tat aag gac gac gat gat aag<br>Ser Ser Ser Ser Gly Gly Ser Gly Asp Tyr Lys Asp Asp Asp Asp Lys<br>330 335 340 | | 1122 |
| gaa gtt cag ctg gtt gaa tca ggt ggt ggt ctg gtt cag cct ggt ggt<br>Glu Val Gln Leu Val Glu Ser Gly Gly Gly Leu Val Gln Pro Gly Gly<br>345 350 355 | | 1170 |
| agc ctg cgt ctg agc tgt gca gca agc ggt ttt act att gaa cgt tat<br>Ser Leu Arg Leu Ser Cys Ala Ala Ser Gly Phe Thr Ile Glu Arg Tyr<br>360 365 370 375 | | 1218 |
| gcg atg ggt tgg gtg cgt cag gct cct ggt aag ggc ctg gaa tgg gtt<br>Ala Met Gly Trp Val Arg Gln Ala Pro Gly Lys Gly Leu Glu Trp Val<br>380 385 390 | | 1266 |
| ggt acg att tat cct tgg ggc gat tat act gat tat gcc gat agc gtc<br>Gly Thr Ile Tyr Pro Trp Gly Asp Tyr Thr Asp Tyr Ala Asp Ser Val<br>395 400 405 | | 1314 |
| aag ggt cgt ttt act ata agt aga gat aat tct aaa aac acc ctc tac<br>Lys Gly Arg Phe Thr Ile Ser Arg Asp Asn Ser Lys Asn Thr Leu Tyr<br>410 415 420 | | 1362 |
| ctg cag atg aac agt cta aga gat gaa gat act gcc gtc tac tac tgc<br>Leu Gln Met Asn Ser Leu Arg Asp Glu Asp Thr Ala Val Tyr Tyr Cys<br>425 430 435 | | 1410 |
| gct cgc tct aac tac ccg aac ggt atg tac tac gtt atg gaa tat tgg<br>Ala Arg Ser Asn Tyr Pro Asn Gly Met Tyr Tyr Val Met Glu Tyr Trp<br>440 445 450 455 | | 1458 |
| ggt cag ggc acc ctg gtt acc gtg agc agc gca agc acc aaa ggt ccg<br>Gly Gln Gly Thr Leu Val Thr Val Ser Ser Ala Ser Thr Lys Gly Pro<br>460 465 470 | | 1506 |
| agc gtg ttt ccg ctg gca ccg agc agc aaa agc acc agc ggt ggc acc<br>Ser Val Phe Pro Leu Ala Pro Ser Ser Lys Ser Thr Ser Gly Gly Thr<br>475 480 485 | | 1554 |
| gca gca ctg ggt tgt ctg gtt aaa gat tat ttt ccg gaa ccg gtt acc<br>Ala Ala Leu Gly Cys Leu Val Lys Asp Tyr Phe Pro Glu Pro Val Thr<br>490 495 500 | | 1602 |
| gtt agc tgg aat agc ggt gca ctg acc agc ggt gtt cat acc ttt ccg<br>Val Ser Trp Asn Ser Gly Ala Leu Thr Ser Gly Val His Thr Phe Pro<br>505 510 515 | | 1650 |
| gca gtt ctg cag agc agc ggt ctg tat agc ctg agc agc gtt gtt acc<br>Ala Val Leu Gln Ser Ser Gly Leu Tyr Ser Leu Ser Ser Val Val Thr<br>520 525 530 535 | | 1698 |
| gtt ccg agc agc agc ctg ggc acc cag acc tat att tgt aat gtt aat<br>Val Pro Ser Ser Ser Leu Gly Thr Gln Thr Tyr Ile Cys Asn Val Asn | | 1746 |

|  |  |  |  |  |  |  |  |  |  |  |  | | | |
|---|---|---|---|---|---|---|---|---|---|---|---|---|---|---|

```
                 540                 545                 550
cat aaa ccg agc aat acc aaa gtg gat aaa aaa gtt gag ccg aaa agc        1794
His Lys Pro Ser Asn Thr Lys Val Asp Lys Lys Val Glu Pro Lys Ser
        555                 560                 565 tgt ggt ggt cat cat cat cac cat cat ggt ggt ggg ggt ggt ggt            1842
Cys Gly Gly His His His His His His Gly Gly Gly Gly Gly Gly
    570                 575                 580 agc tca tct agc ggt agc ggt tct agc agc tct agc agt agc agc tct        1890
Ser Ser Ser Ser Gly Ser Gly Ser Ser Ser Ser Ser Ser Ser Ser Ser
585                 590                 595 ggt tca agc tca agt agc tca agc tca agc tct agt agc agc ggc tcc        1938
Gly Ser Ser Ser Ser Ser Ser Ser Ser Ser Ser Ser Ser Ser Gly Ser
600                 605                 610                 615 ggt ggt ggc ggt tca ggt agc tca tca ggc agc tca ggc ggt ggt agt        1986
Gly Gly Gly Gly Ser Gly Ser Ser Ser Gly Ser Ser Gly Gly Gly Ser
            620                 625                 630 ggc ggt ggt tca ggt tca ggt ggt agc tct ggt ggt ggc agc agt tca        2034
Gly Gly Gly Ser Gly Ser Gly Gly Ser Ser Gly Gly Gly Ser Ser Ser
            635                 640                 645 agc tca tct ggt tct agt tca ggt agc ggc agc gga ggt ggt ggc gga        2082
Ser Ser Ser Gly Ser Ser Ser Gly Ser Gly Ser Gly Gly Gly Gly Gly
            650                 655                 660 agc agc agt agt tca ggc ggt ggc agc tct agc ggt ggt tca tca agc        2130
Ser Ser Ser Ser Ser Gly Gly Gly Ser Ser Ser Gly Gly Ser Ser Ser
        665                 670                 675 ggt ggc agt tcc ggt ggt ggt ggc tct agt ggt tca gca aaa ttt tca        2178
Gly Gly Ser Ser Gly Gly Gly Gly Ser Ser Gly Ser Ala Lys Phe Ser
680                 685                 690                 695 acc cct gtt tgg att tca cag gcc cag ggc att cgc gca ggc cct ccg        2226
Thr Pro Val Trp Ile Ser Gln Ala Gln Gly Ile Arg Ala Gly Pro Pro
                700                 705                 710 taatgaagcg gtagtgccgg tgccggtgcg ggtggtagca agatattcg tccattcgtt        2286 tgtgaatatc aaggccaatc gtctgacctg ccgcacacct tactggtgtg cgg             2339

<210> SEQ ID NO 22
<211> LENGTH: 711
<212> TYPE: PRT
<213> ORGANISM: Artificial sequence
<220> FEATURE:
<223> OTHER INFORMATION: Synthetic Construct

<400> SEQUENCE: 22

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Lys Asn
            20                  25                  30

Tyr Leu Ser Trp Tyr Gln Gln Pro Gly Asn Ala Pro Lys Pro Leu
        35                  40                  45

Ile Tyr Ala Gly Ser Asn Arg Gln Ser Gly Val Pro Ser Arg Phe Ser
    50                  55                  60

Gly Ser Gly Ser Glu Thr Asp Phe Thr Leu Thr Ile Ser Ser Leu Gln
65                  70                  75                  80

Pro Glu Asp Phe Ala Thr Tyr Tyr Cys Gln Gln Thr Tyr Ile Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Asp Tyr Lys Asp Asp Asp Asp
    210                 215                 220

Lys Ser Gly Ser Ser Gly Ser Gly Ser Ser Ser Ser Gly Ser
225                 230                 235                 240

Ser Gly Gly Gly Ser Ser Ser Gly Ser Gly Gly Gly Ser Ser
                245                 250                 255

Ser Gly Gly Gly Ser Gly Ser Ser Gly Ser Ser Ser Ser Gly
                260                 265                 270

Ser Gly Ser Ser Gly Ser Gly Ser Ser Ser Gly Gly Gly Gly
            275                 280                 285

Ser Ser Ser Gly Ser Ser Ser Gly Gly Gly Gly Ser Ser Ser
290                 295                 300

Gly Ser Ser Ser Gly Ser Gly Gly Ser Ser Ser Gly Ser Ser Gly
305                 310                 315                 320

Gly Ser Ser Ser Ser Ser Ser Ser Ser Gly Gly Ser Gly Asp
                325                 330                 335

Tyr Lys Asp Asp Asp Asp Lys Glu Val Gln Leu Val Glu Ser Gly Gly
                340                 345                 350

Gly Leu Val Gln Pro Gly Gly Ser Leu Arg Leu Ser Cys Ala Ala Ser
            355                 360                 365

Gly Phe Thr Ile Glu Arg Tyr Ala Met Gly Trp Val Arg Gln Ala Pro
        370                 375                 380

Gly Lys Gly Leu Glu Trp Val Gly Thr Ile Tyr Pro Trp Gly Asp Tyr
385                 390                 395                 400

Thr Asp Tyr Ala Asp Ser Val Lys Gly Arg Phe Thr Ile Ser Arg Asp
                405                 410                 415

Asn Ser Lys Asn Thr Leu Tyr Leu Gln Met Asn Ser Leu Arg Asp Glu
            420                 425                 430

Asp Thr Ala Val Tyr Tyr Cys Ala Arg Ser Asn Tyr Pro Asn Gly Met
        435                 440                 445

Tyr Tyr Val Met Glu Tyr Trp Gly Gln Gly Thr Leu Val Thr Val Ser
    450                 455                 460

Ser Ala Ser Thr Lys Gly Pro Ser Val Phe Pro Leu Ala Pro Ser Ser
465                 470                 475                 480

Lys Ser Thr Ser Gly Gly Thr Ala Ala Leu Gly Cys Leu Val Lys Asp
                485                 490                 495

Tyr Phe Pro Glu Pro Val Thr Val Ser Trp Asn Ser Gly Ala Leu Thr
            500                 505                 510

Ser Gly Val His Thr Phe Pro Ala Val Leu Gln Ser Ser Gly Leu Tyr
        515                 520                 525

Ser Leu Ser Ser Val Val Thr Val Pro Ser Ser Ser Leu Gly Thr Gln
    530                 535                 540
```

```
Thr Tyr Ile Cys Asn Val Asn His Lys Pro Ser Asn Thr Lys Val Asp
545                 550                 555                 560

Lys Lys Val Glu Pro Lys Ser Cys Gly Gly His His His His His His
            565                 570                 575

Gly Gly Gly Gly Gly Gly Ser Ser Ser Gly Ser Gly Ser Ser
        580                 585                 590

Ser Ser Ser Ser Ser Ser Ser Gly Ser Ser Ser Ser Ser Ser Ser
    595                 600                 605

Ser Ser Ser Ser Gly Ser Gly Gly Gly Ser Gly Ser Ser Ser
    610                 615                 620

Gly Ser Ser Gly Gly Gly Ser Gly Gly Gly Ser Gly Ser Gly Gly Ser
625                 630                 635                 640

Ser Gly Gly Gly Ser Ser Ser Ser Ser Gly Ser Ser Ser Gly Ser
                645                 650                 655

Gly Ser Gly Gly Gly Gly Ser Ser Ser Ser Gly Gly Gly Ser
            660                 665                 670

Ser Ser Gly Gly Ser Ser Gly Gly Ser Ser Gly Gly Gly Ser
            675                 680                 685

Ser Gly Ser Ala Lys Phe Ser Thr Pro Val Trp Ile Ser Gln Ala Gln
    690                 695                 700

Gly Ile Arg Ala Gly Pro Pro
705                 710

<210> SEQ ID NO 23
<211> LENGTH: 55
<212> TYPE: DNA
<213> ORGANISM: Artificial sequence
<220> FEATURE:
<223> OTHER INFORMATION: Synthetic PURE-rt-1F primer

<400> SEQUENCE: 23
caatttcggt aatacgactc actatagggg gaatttaggt gacactatag aagtg          55

<210> SEQ ID NO 24
<211> LENGTH: 21
<212> TYPE: DNA
<213> ORGANISM: Artificial sequence
<220> FEATURE:
<223> OTHER INFORMATION: Synthetic PURE-3R primer

<400> SEQUENCE: 24
caggtcagac gattggcctt g                                               21

<210> SEQ ID NO 25
<211> LENGTH: 70
<212> TYPE: DNA
<213> ORGANISM: Artificial sequence
<220> FEATURE:
<223> OTHER INFORMATION: Synthetic SL-1F primer

<400> SEQUENCE: 25
caatttcggt aatacgactc actatagggg gaccacaacg gtttccatt taggtgacac      60 tatagaagtg                                                            70

<210> SEQ ID NO 26
<211> LENGTH: 57
<212> TYPE: DNA
<213> ORGANISM: Artificial sequence
<220> FEATURE:
<223> OTHER INFORMATION: Synthetic SL-2R primer
```

```
<400> SEQUENCE: 26
ccgcacacca gtaaggtgtg cggcaggtca gacgattggc cttgatattc acaaacg        57

<210> SEQ ID NO 27
<211> LENGTH: 27
<212> TYPE: DNA
<213> ORGANISM: Artificial sequence
<220> FEATURE:
<223> OTHER INFORMATION: Synthetic PURE-2R primer

<400> SEQUENCE: 27
gacgattggc cttgatattc acaaacg                                         27

<210> SEQ ID NO 28
<211> LENGTH: 27
<212> TYPE: DNA
<213> ORGANISM: Artificial sequence
<220> FEATURE:
<223> OTHER INFORMATION: Synthetic L-CDRex-1F primer

<400> SEQUENCE: 28
attaaacgta ccgttgcagc accgagc                                         27

<210> SEQ ID NO 29
<211> LENGTH: 26
<212> TYPE: DNA
<213> ORGANISM: Artificial sequence
<220> FEATURE:
<223> OTHER INFORMATION: Synthetic H-CDRex-2R primer

<400> SEQUENCE: 29
tgagcctcca ggctgaacca gaccac                                          26

<210> SEQ ID NO 30
<211> LENGTH: 17
<212> TYPE: PRT
<213> ORGANISM: Artificial sequence
<220> FEATURE:
<223> OTHER INFORMATION: Synthetic secM
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid

<400> SEQUENCE: 30

Phe Xaa Xaa Xaa Xaa Trp Ile Xaa Xaa Xaa Xaa Gly Ile Arg Ala Gly
 1               5                  10                  15
Pro

<210> SEQ ID NO 31
<211> LENGTH: 5
<212> TYPE: PRT
<213> ORGANISM: Artificial sequence
<220> FEATURE:
<223> OTHER INFORMATION: Synthetic enterokinase recognition sequence

<400> SEQUENCE: 31

Asp Asp Asp Asp Lys
 1               5

<210> SEQ ID NO 32
<211> LENGTH: 4
```

```
<212> TYPE: PRT
<213> ORGANISM: Artificial sequence
<220> FEATURE:
<223> OTHER INFORMATION: Synthetic factor Xa recognition sequence

<400> SEQUENCE: 32

Ile Glu Gly Arg
1

<210> SEQ ID NO 33
<211> LENGTH: 27
<212> TYPE: DNA
<213> ORGANISM: Artificial sequence
<220> FEATURE:
<223> OTHER INFORMATION: Synthetic RT-1F primer

<400> SEQUENCE: 33
gatattcaga tgacccagag cccgagc                                       27

<210> SEQ ID NO 34
<211> LENGTH: 21
<212> TYPE: DNA
<213> ORGANISM: Artificial sequence
<220> FEATURE:
<223> OTHER INFORMATION: Synthetic RT-1R primer

<400> SEQUENCE: 34
cagcttcggg gctttcctg g                                              21

<210> SEQ ID NO 35
<211> LENGTH: 24
<212> TYPE: DNA
<213> ORGANISM: Artificial sequence
<220> FEATURE:
<223> OTHER INFORMATION: Synthetic HH-4F primer

<400> SEQUENCE: 35
ccagggaact tggttactg tttc                                           24

<210> SEQ ID NO 36
<211> LENGTH: 22
<212> TYPE: DNA
<213> ORGANISM: Artificial sequence
<220> FEATURE:
<223> OTHER INFORMATION: Synthetic Model-4R primer

<400> SEQUENCE: 36
ctttaaccag acaacccagt gc                                            22

<210> SEQ ID NO 37
<211> LENGTH: 153
<212> TYPE: DNA
<213> ORGANISM: Artificial sequence
<220> FEATURE:
<223> OTHER INFORMATION: Synthetic partial sequence of pGAv6.5
<220> FEATURE:
<221> NAME/KEY: CDS
<222> LOCATION: (1)..(60)
<223> OTHER INFORMATION: secM
<220> FEATURE:
<221> NAME/KEY: CDS
<222> LOCATION: (67)..(126)
<223> OTHER INFORMATION: secM

<400> SEQUENCE: 37 gca aaa ttt tca acc cct gtt tgg att tca cag gcc cag ggc att cgc    48
Ala Lys Phe Ser Thr Pro Val Trp Ile Ser Gln Ala Gln Gly Ile Arg
1               5                   10                  15
```

```
gca ggc cct ccg taatga gcc aag ttt agt aca ccc gtc tgg ata agt      96
Ala Gly Pro Pro        Ala Lys Phe Ser Thr Pro Val Trp Ile Ser
         20                     25                  30 caa gcc caa gga ata cga gcc gga cct ccc tagtgacaag gccaatcgtc     146
Gln Ala Gln Gly Ile Arg Ala Gly Pro Pro
             35                  40 tgacctg                                                            153

<210> SEQ ID NO 38
<211> LENGTH: 20
<212> TYPE: PRT
<213> ORGANISM: Artificial sequence
<220> FEATURE:
<223> OTHER INFORMATION: Synthetic Construct

<400> SEQUENCE: 38

Ala Lys Phe Ser Thr Pro Val Trp Ile Ser Gln Ala Gln Gly Ile Arg
1               5                   10                  15

Ala Gly Pro Pro
         20

<210> SEQ ID NO 39
<211> LENGTH: 20
<212> TYPE: PRT
<213> ORGANISM: Artificial sequence
<220> FEATURE:
<223> OTHER INFORMATION: Synthetic Construct

<400> SEQUENCE: 39

Ala Lys Phe Ser Thr Pro Val Trp Ile Ser Gln Ala Gln Gly Ile Arg
1               5                   10                  15

Ala Gly Pro Pro
         20

<210> SEQ ID NO 40
<211> LENGTH: 219
<212> TYPE: DNA
<213> ORGANISM: Artificial sequence
<220> FEATURE:
<223> OTHER INFORMATION: Synthetic partial sequence of pGAv6.5-S3
<220> FEATURE:
<221> NAME/KEY: CDS
<222> LOCATION: (1)..(60)
<223> OTHER INFORMATION: secM
<220> FEATURE:
<221> NAME/KEY: CDS
<222> LOCATION: (67)..(126)
<223> OTHER INFORMATION: secM
<220> FEATURE:
<221> NAME/KEY: CDS
<222> LOCATION: (133)..(192)
<223> OTHER INFORMATION: secM

<400> SEQUENCE: 40 gca aaa ttt tca acc cct gtt tgg att tca cag gcc cag ggc att cgc      48
Ala Lys Phe Ser Thr Pro Val Trp Ile Ser Gln Ala Gln Gly Ile Arg
1               5                   10                  15 gca ggc cct ccg taatga gcc aag ttt agt aca ccc gtc tgg ata agt       96
Ala Gly Pro Pro        Ala Lys Phe Ser Thr Pro Val Trp Ile Ser
         20                     25                  30 caa gcc caa gga ata cga gcc gga cct ccc tagtga gct aaa ttc agc     144
Gln Ala Gln Gly Ile Arg Ala Gly Pro Pro        Ala Lys Phe Ser
             35                  40 acg cca gta tgg atc tct cag gca caa ggt atc aga gct ggg cca ccg    192
Thr Pro Val Trp Ile Ser Gln Ala Gln Gly Ile Arg Ala Gly Pro Pro
```
taatagcaag gccaatcgtc tgacctg                                                        219

<210> SEQ ID NO 41
<211> LENGTH: 20
<212> TYPE: PRT
<213> ORGANISM: Artificial sequence
<220> FEATURE:
<223> OTHER INFORMATION: Synthetic Construct

<400> SEQUENCE: 41

Ala Lys Phe Ser Thr Pro Val Trp Ile Ser Gln Ala Gln Gly Ile Arg
1               5                   10                  15

Ala Gly Pro Pro
            20

<210> SEQ ID NO 42
<211> LENGTH: 20
<212> TYPE: PRT
<213> ORGANISM: Artificial sequence
<220> FEATURE:
<223> OTHER INFORMATION: Synthetic Construct

<400> SEQUENCE: 42

Ala Lys Phe Ser Thr Pro Val Trp Ile Ser Gln Ala Gln Gly Ile Arg
1               5                   10                  15

Ala Gly Pro Pro
            20

<210> SEQ ID NO 43
<211> LENGTH: 20
<212> TYPE: PRT
<213> ORGANISM: Artificial sequence
<220> FEATURE:
<223> OTHER INFORMATION: Synthetic Construct

<400> SEQUENCE: 43

Ala Lys Phe Ser Thr Pro Val Trp Ile Ser Gln Ala Gln Gly Ile Arg
1               5                   10                  15

Ala Gly Pro Pro
            20

<210> SEQ ID NO 44
<211> LENGTH: 285
<212> TYPE: DNA
<213> ORGANISM: Artificial sequence
<220> FEATURE:
<223> OTHER INFORMATION: Synthetic partial sequence of pGAv6.5-S4
<220> FEATURE:
<221> NAME/KEY: CDS
<222> LOCATION: (1)..(60)
<223> OTHER INFORMATION: secM
<220> FEATURE:
<221> NAME/KEY: CDS
<222> LOCATION: (67)..(126)
<223> OTHER INFORMATION: secM
<220> FEATURE:
<221> NAME/KEY: CDS
<222> LOCATION: (133)..(192)
<223> OTHER INFORMATION: secM
<220> FEATURE:
<221> NAME/KEY: CDS
<222> LOCATION: (199)..(258)
<223> OTHER INFORMATION: secM

<400> SEQUENCE: 44 gca aaa ttt tca acc cct gtt tgg att tca cag gcc cag ggc att cgc        48

```
Ala Lys Phe Ser Thr Pro Val Trp Ile Ser Gln Ala Gln Gly Ile Arg
1               5                   10                  15 gca ggc cct ccg taatga gcc aag ttt agt aca ccc gtc tgg ata agt         96
Ala Gly Pro Pro        Ala Lys Phe Ser Thr Pro Val Trp Ile Ser
            20                     25                  30 caa gcc caa gga ata cga gcc gga cct ccc tagtga gct aaa ttc agc        144
Gln Ala Gln Gly Ile Arg Ala Gly Pro Pro        Ala Lys Phe Ser
                35                  40 acg cca gta tgg atc tct cag gca caa ggt atc aga gct ggg cca ccg       192
Thr Pro Val Trp Ile Ser Gln Ala Gln Gly Ile Arg Ala Gly Pro Pro
45                  50                  55                  60 taatag gcg aag ttt tcg act ccg gtg tgg ata agc caa gcg cag ggg        240
       Ala Lys Phe Ser Thr Pro Val Trp Ile Ser Gln Ala Gln Gly
                65                      70 att cgt gcc ggt cca ccc tagtgacaag gccaatcgtc tgacctg                 285
Ile Arg Ala Gly Pro Pro
75                  80

<210> SEQ ID NO 45
<211> LENGTH: 20
<212> TYPE: PRT
<213> ORGANISM: Artificial sequence
<220> FEATURE:
<223> OTHER INFORMATION: Synthetic Construct

<400> SEQUENCE: 45

Ala Lys Phe Ser Thr Pro Val Trp Ile Ser Gln Ala Gln Gly Ile Arg
1               5                   10                  15

Ala Gly Pro Pro
            20

<210> SEQ ID NO 46
<211> LENGTH: 20
<212> TYPE: PRT
<213> ORGANISM: Artificial sequence
<220> FEATURE:
<223> OTHER INFORMATION: Synthetic Construct

<400> SEQUENCE: 46

Ala Lys Phe Ser Thr Pro Val Trp Ile Ser Gln Ala Gln Gly Ile Arg
1               5                   10                  15

Ala Gly Pro Pro
            20

<210> SEQ ID NO 47
<211> LENGTH: 20
<212> TYPE: PRT
<213> ORGANISM: Artificial sequence
<220> FEATURE:
<223> OTHER INFORMATION: Synthetic Construct

<400> SEQUENCE: 47

Ala Lys Phe Ser Thr Pro Val Trp Ile Ser Gln Ala Gln Gly Ile Arg
1               5                   10                  15

Ala Gly Pro Pro
            20

<210> SEQ ID NO 48
<211> LENGTH: 20
<212> TYPE: PRT
<213> ORGANISM: Artificial sequence
<220> FEATURE:
<223> OTHER INFORMATION: Synthetic Construct
```

-continued

```
<400> SEQUENCE: 48

Ala Lys Phe Ser Thr Pro Val Trp Ile Ser Gln Ala Gln Gly Ile Arg
1               5                   10                  15

Ala Gly Pro Pro
            20

<210> SEQ ID NO 49
<211> LENGTH: 19
<212> TYPE: DNA
<213> ORGANISM: Artificial sequence
<220> FEATURE:
<223> OTHER INFORMATION: Synthetic TT-5F primer

<400> SEQUENCE: 49
gcaccctggt taccgtgag                                                   19

<210> SEQ ID NO 50
<211> LENGTH: 120
<212> TYPE: DNA
<213> ORGANISM: Artificial sequence
<220> FEATURE:
<223> OTHER INFORMATION: Synthetic partial sequence of pGAv7
<220> FEATURE:
<221> NAME/KEY: CDS
<222> LOCATION: (1)..(120)
<220> FEATURE:
<221> NAME/KEY: misc_feature
<222> LOCATION: (43)..(100)
<223> OTHER INFORMATION: linker-coding sequence

<400> SEQUENCE: 50 agc aat acc aaa gtg gat aaa aaa gtt gag ccg aaa agc tgt ggt ggt        48
Ser Asn Thr Lys Val Asp Lys Lys Val Glu Pro Lys Ser Cys Gly Gly
1               5                   10                  15 cat cat cat cac cat cat ggt ggt ggg ggt ggt ggt ggt agc tca tct        96
His His His His His His Gly Gly Gly Gly Gly Gly Gly Ser Ser Ser
                20                  25                  30 agc ggt gca aaa ttt tca acc cct                                       120
Ser Gly Ala Lys Phe Ser Thr Pro
            35                  40

<210> SEQ ID NO 51
<211> LENGTH: 40
<212> TYPE: PRT
<213> ORGANISM: Artificial sequence
<220> FEATURE:
<223> OTHER INFORMATION: Synthetic Construct

<400> SEQUENCE: 51

Ser Asn Thr Lys Val Asp Lys Lys Val Glu Pro Lys Ser Cys Gly Gly
1               5                   10                  15

His His His His His His Gly Gly Gly Gly Gly Gly Ser Ser Ser
                20                  25                  30

Ser Gly Ala Lys Phe Ser Thr Pro
            35                  40

<210> SEQ ID NO 52
<211> LENGTH: 120
<212> TYPE: DNA
<213> ORGANISM: Artificial sequence
<220> FEATURE:
<223> OTHER INFORMATION: Synthetic partial sequence of pGAv8
<220> FEATURE:
<221> NAME/KEY: CDS
<222> LOCATION: (1)..(120)
<220> FEATURE:
```

```
<221> NAME/KEY: misc_feature
<222> LOCATION: (19)..(106)
<223> OTHER INFORMATION: linker coding sequence

<400> SEQUENCE: 52 ttt aat cgt ggt gaa tgc ggt ggc ggt ggc agc ggt ggt ggc ggt tct    48
Phe Asn Arg Gly Glu Cys Gly Gly Gly Gly Ser Gly Gly Gly Gly Ser
1               5                   10                  15 ggt ggc ggc ggt agc ggc ggt ggt ggc tct ggt ggt ggc ggc agc ggc    96
Gly Gly Gly Gly Ser Gly Gly Gly Gly Ser Gly Gly Gly Gly Ser Gly
            20                  25                  30 ggc ggt ggt tct gaa gtt cag ctg                                    120
Gly Gly Gly Ser Glu Val Gln Leu
        35                  40

<210> SEQ ID NO 53
<211> LENGTH: 40
<212> TYPE: PRT
<213> ORGANISM: Artificial sequence
<220> FEATURE:
<223> OTHER INFORMATION: Synthetic Construct

<400> SEQUENCE: 53

Phe Asn Arg Gly Glu Cys Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Glu Val Gln Leu
        35                  40

<210> SEQ ID NO 54
<211> LENGTH: 29
<212> TYPE: DNA
<213> ORGANISM: Artificial sequence
<220> FEATURE:
<223> OTHER INFORMATION: Synthetic T1P-F primer

<400> SEQUENCE: 54
gttttactat tgaacgttat gcgatgggt                                    29

<210> SEQ ID NO 55
<211> LENGTH: 27
<212> TYPE: DNA
<213> ORGANISM: Artificial sequence
<220> FEATURE:
<223> OTHER INFORMATION: Synthetic T1P-R primer

<400> SEQUENCE: 55
cgtagtacat accgttcggg tagttag                                      27

<210> SEQ ID NO 56
<211> LENGTH: 18
<212> TYPE: DNA
<213> ORGANISM: Artificial sequence
<220> FEATURE:
<223> OTHER INFORMATION: Synthetic Core-1F primer

<400> SEQUENCE: 56
gcgcaagcgt tggtgatc                                                18

<210> SEQ ID NO 57
<211> LENGTH: 20
<212> TYPE: DNA
<213> ORGANISM: Artificial sequence
<220> FEATURE:
```

<223> OTHER INFORMATION: Synthetic Core-1R primer

<400> SEQUENCE: 57
gctcggacct ttggtgcttg                                       20

<210> SEQ ID NO 58
<211> LENGTH: 30
<212> TYPE: DNA
<213> ORGANISM: Artificial sequence
<220> FEATURE:
<223> OTHER INFORMATION: Synthetic FabTT Ymacs-1 L1-1 primer
<220> FEATURE:
<221> NAME/KEY: misc_feature
<222> LOCATION: (16)..(17)
<223> OTHER INFORMATION: n is a, c, g, or t

<400> SEQUENCE: 58
tgtcgtgcaa gccagnnkat taaaaattat                            30

<210> SEQ ID NO 59
<211> LENGTH: 30
<212> TYPE: DNA
<213> ORGANISM: Artificial sequence
<220> FEATURE:
<223> OTHER INFORMATION: Synthetic FabTT Ymacs-1 H3-12 primer
<220> FEATURE:
<221> NAME/KEY: misc_feature
<222> LOCATION: (16)..(17)
<223> OTHER INFORMATION: n is a, c, g, or t

<400> SEQUENCE: 59
atgtactacg ttatgnnkta ttggggtcag                            30

<210> SEQ ID NO 60
<211> LENGTH: 55
<212> TYPE: DNA
<213> ORGANISM: Artificial sequence
<220> FEATURE:
<223> OTHER INFORMATION: Synthetic PURE-rt-1F primer

<400> SEQUENCE: 60
caatttcggt aatacgactc actataggga gaatttaggt gacactatag aagtg    55

<210> SEQ ID NO 61
<211> LENGTH: 40
<212> TYPE: DNA
<213> ORGANISM: Artificial sequence
<220> FEATURE:
<223> OTHER INFORMATION: Synthetic H3checkR Not TA6 primer

<400> SEQUENCE: 61
tatatatata tagcggccgc agaactgccg gaaaggtatg                  40

<210> SEQ ID NO 62
<211> LENGTH: 51
<212> TYPE: DNA
<213> ORGANISM: Artificial sequence
<220> FEATURE:
<223> OTHER INFORMATION: Synthetic FabTT Ymacs-2 L1-Fwd primer

<400> SEQUENCE: 62
tgtcgtgcaa gccaggatat taaaaattat tgwcttggt atcaacaaca a       51

<210> SEQ ID NO 63
<211> LENGTH: 51
<212> TYPE: DNA
<213> ORGANISM: Artificial sequence

```
<220> FEATURE:
<223> OTHER INFORMATION: Synthetic FabTT Ymacs-2 L2-Fwd primer

<400> SEQUENCE: 63
gccccgaagc cactgattta tgstggttct aaccgccaat ctggagttcc t            51

<210> SEQ ID NO 64
<211> LENGTH: 48
<212> TYPE: DNA
<213> ORGANISM: Artificial sequence
<220> FEATURE:
<223> OTHER INFORMATION: Synthetic FabTT Ymacs-2 L3-Fwd primer
<220> FEATURE:
<221> NAME/KEY: misc_feature
<222> LOCATION: (26)..(26)
<223> OTHER INFORMATION: n is a, c, g, or t

<400> SEQUENCE: 64
acctattatt gccaacaaac tkmtrnmtac cctatcacct ttggccag                48

<210> SEQ ID NO 65
<211> LENGTH: 60
<212> TYPE: DNA
<213> ORGANISM: Artificial sequence
<220> FEATURE:
<223> OTHER INFORMATION: Synthetic FabTT Ymacs-2 H1-Fwd primer

<400> SEQUENCE: 65
agctgtgcag caagcggttt tasaattgrg cgttatgcga tgrsttgggt gcgtcaggct   60

<210> SEQ ID NO 66
<211> LENGTH: 60
<212> TYPE: DNA
<213> ORGANISM: Artificial sequence
<220> FEATURE:
<223> OTHER INFORMATION: Synthetic FabTT Ymacs-2 H2-Fwd primer

<400> SEQUENCE: 66
ggcctggaat gggttggtac gatttatcct kdsrscgatt atrbygatta tgccgatagc   60

<210> SEQ ID NO 67
<211> LENGTH: 54
<212> TYPE: DNA
<213> ORGANISM: Artificial sequence
<220> FEATURE:
<223> OTHER INFORMATION: Synthetic FabTT Ymacs-2 H3-Fwd primer

<400> SEQUENCE: 67
tactactgcg ctcgctctaa ctacccgaac ggtmtgkrct acgttatgga atat         54

<210> SEQ ID NO 68
<211> LENGTH: 30
<212> TYPE: DNA
<213> ORGANISM: Artificial sequence
<220> FEATURE:
<223> OTHER INFORMATION: Synthetic Cis-1F primer

<400> SEQUENCE: 68
cagttgatcg gcgcgagatt taatcgccgc                                    30

<210> SEQ ID NO 69
<211> LENGTH: 40
<212> TYPE: DNA
<213> ORGANISM: Artificial sequence
<220> FEATURE:
<223> OTHER INFORMATION: Synthetic Cis-1R primer
```

<400> SEQUENCE: 69
cgtaagccgg tactgattga tagatttcac cttacccatc        40

<210> SEQ ID NO 70
<211> LENGTH: 4100
<212> TYPE: DNA
<213> ORGANISM: Artificial sequence
<220> FEATURE:
<223> OTHER INFORMATION: Synthetic v10.1-HH xhoI construct
<220> FEATURE:
<221> NAME/KEY: CDS
<222> LOCATION: (689)..(3322)

<400> SEQUENCE: 70

```
cagttgatcg gcgcgagatt taatcgccgc gacaatttgc gacggcgcgt gcagggccag      60
actggaggtg gcaacgccaa tcagcaacga ctgtttgccc gccagttgtt gtgccacgcg     120
gttgggaatg taattcagct ccgccatcgc cgcttccact tttcccgcg ttttcgcaga     180 aacgtggctg gcctggttca ccacgcggga aacggtctga taagagacac cggcatactc     240
tgcgacatcg tataacgtta ctggtttcac attcaccacc ctgaattgac tctcttccgg     300
gcgctatcat gccataccgc gaaaggtttt gcaccattcg gctagcgatg accctgctga     360
ttggttcgct gaccatttcc ggggtgcgga acggcgttac cagaaactca gaaggttcgt     420
ccaaccaaac cgactctgac ggcagtttac gagagagatg ataggggtctg cttcagtaag     480 ccagatgcta cacaattagg cttgtacata ttgtcgttag aacgcggcta caattaatac     540
ataaccttat gtatcataca catacgattt aggtgacact atagaataca agcttactcc     600
ccatccccct gttgacaatt aatcatggct cgtataatgt gtggaattgt gagcggataa     660
caatttcaca caggaaacag gatctacc atg gat att cag atg acc cag agc        712
                                 Met Asp Ile Gln Met Thr Gln Ser
                                   1               5
```

| | | | | | | | | | | | | | | | | |
|---|---|---|---|---|---|---|---|---|---|---|---|---|---|---|---|---|
| ccg | agc | agc | ctg | agc | gca | agc | gtt | ggt | gat | cgt | gtc | acc | atc | acc | tgc | 760 |
| Pro | Ser | Ser | Leu | Ser | Ala | Ser | Val | Gly | Asp | Arg | Val | Thr | Ile | Thr | Cys | |
| | 10 | | | | 15 | | | | | 20 | | | | | | |

| | | | | | | | | | | | | | | | |
|---|---|---|---|---|---|---|---|---|---|---|---|---|---|---|---|
| cgt | gcc | agt | cag | gat | gtg | aac | acc | gcc | gtt | gca | tgg | tat | caa | caa | aaa |  808
| Arg | Ala | Ser | Gln | Asp | Val | Asn | Thr | Ala | Val | Ala | Trp | Tyr | Gln | Gln | Lys |
| 25 | | | | | 30 | | | | | 35 | | | | | 40 |

| | | | | | | | | | | | | | | | |
|---|---|---|---|---|---|---|---|---|---|---|---|---|---|---|---|
| cca | gga | aaa | gcc | ccg | aag | ctg | ctg | att | tat | agc | gcc | tct | ttt | ctg | tat | 856
| Pro | Gly | Lys | Ala | Pro | Lys | Leu | Leu | Ile | Tyr | Ser | Ala | Ser | Phe | Leu | Tyr |
| | | | | 45 | | | | | 50 | | | | | 55 | |

| | | | | | | | | | | | | | | | |
|---|---|---|---|---|---|---|---|---|---|---|---|---|---|---|---|
| tct | gga | gtt | cct | tct | cgc | ttc | tcc | gga | tcc | cgt | tct | ggc | act | gat | ttt | 904
| Ser | Gly | Val | Pro | Ser | Arg | Phe | Ser | Gly | Ser | Arg | Ser | Gly | Thr | Asp | Phe |
| | | | | 60 | | | | | 65 | | | | | 70 | |

| | | | | | | | | | | | | | | | |
|---|---|---|---|---|---|---|---|---|---|---|---|---|---|---|---|
| act | cta | act | att | agt | agt | cta | cag | ccg | gag | gac | ttc | gcc | acc | tat | tat | 952
| Thr | Leu | Thr | Ile | Ser | Ser | Leu | Gln | Pro | Glu | Asp | Phe | Ala | Thr | Tyr | Tyr |
| | | | 75 | | | | | 80 | | | | | 85 | | |

| | | | | | | | | | | | | | | | |
|---|---|---|---|---|---|---|---|---|---|---|---|---|---|---|---|
| tgc | caa | caa | cat | tac | acc | acc | cct | ccg | act | ttc | ggc | cag | ggt | acc | aag | 1000
| Cys | Gln | Gln | His | Tyr | Thr | Thr | Pro | Pro | Thr | Phe | Gly | Gln | Gly | Thr | Lys |
| | 90 | | | | 95 | | | | | 100 | | | | | |

| | | | | | | | | | | | | | | | |
|---|---|---|---|---|---|---|---|---|---|---|---|---|---|---|---|
| gtg | gaa | att | aaa | cgt | acc | gtt | gca | gca | ccg | agc | gtt | ttt | att | ttc | ccg | 1048
| Val | Glu | Ile | Lys | Arg | Thr | Val | Ala | Ala | Pro | Ser | Val | Phe | Ile | Phe | Pro |
| 105 | | | | | 110 | | | | | 115 | | | | | 120 |

| | | | | | | | | | | | | | | | |
|---|---|---|---|---|---|---|---|---|---|---|---|---|---|---|---|
| cct | agt | gat | gaa | cag | ctg | aaa | agc | ggc | acc | gca | agc | gtt | gtt | tgt | ctg | 1096
| Pro | Ser | Asp | Glu | Gln | Leu | Lys | Ser | Gly | Thr | Ala | Ser | Val | Val | Cys | Leu |
| | | | | 125 | | | | | 130 | | | | | 135 | |

| | | | | | | | | | | | | | | | |
|---|---|---|---|---|---|---|---|---|---|---|---|---|---|---|---|
| ctg | aat | aat | ttt | tat | ccg | cgt | gaa | gca | aaa | gtg | cag | tgg | aaa | gtt | gat | 1144
| Leu | Asn | Asn | Phe | Tyr | Pro | Arg | Glu | Ala | Lys | Val | Gln | Trp | Lys | Val | Asp |
| | | | 140 | | | | | 145 | | | | | 150 | | |

-continued

| | | |
|---|---|---|
| aat gca ctg cag agc ggt aat agc caa gaa agc gtt acc gaa cag gat<br>Asn Ala Leu Gln Ser Gly Asn Ser Gln Glu Ser Val Thr Glu Gln Asp<br>             155                      160                         165 | 1192 | |
| agc aaa gat agc acc tat agc ctg agc agc acc ctg acc ctg agc aaa<br>Ser Lys Asp Ser Thr Tyr Ser Leu Ser Ser Thr Leu Thr Leu Ser Lys<br>170                       175                         180 | 1240 | |
| gca gat tat gaa aaa cac aaa gtg tat gcc tgc gaa gtt acc cat cag<br>Ala Asp Tyr Glu Lys His Lys Val Tyr Ala Cys Glu Val Thr His Gln<br>185                       190                       195                   200 | 1288 | |
| ggt ctg agc agt ccg gtt acc aaa agc ttt aat cgt ggt gaa tgc ggt<br>Gly Leu Ser Ser Pro Val Thr Lys Ser Phe Asn Arg Gly Glu Cys Gly<br>                  205                       210                     215 | 1336 | |
| ggc gat tat aaa gat gat gat gat aaa agc ggt agc agc ggt agt ggt<br>Gly Asp Tyr Lys Asp Asp Asp Asp Lys Ser Gly Ser Ser Gly Ser Gly<br>             220                       225                     230 | 1384 | |
| agc ggt agc agt agt agc ggt tca agc ggt ggt agc agc agc tca<br>Ser Gly Ser Ser Ser Ser Gly Ser Gly Gly Ser Ser Ser<br>235                      240                     245 | 1432 | |
| ggt agt ggt ggt ggt ggt tca agc agc ggt ggc agt agc ggt agc<br>Gly Ser Gly Gly Gly Gly Ser Ser Gly Gly Ser Ser Gly Ser<br>250                      255                       260 | 1480 | |
| tca agc ggt agc tct agc agc ggt tct ggt agc agt ggt tca ggt agt<br>Ser Ser Gly Ser Ser Ser Ser Gly Ser Gly Ser Ser Gly Ser Gly Ser<br>265                       270                       275                   280 | 1528 | |
| agc agc agc ggt ggc ggt ggc tca agt agt ggt agc agc tca tca<br>Ser Ser Ser Gly Gly Gly Gly Ser Ser Ser Gly Ser Ser Ser<br>                  285                       290                     295 | 1576 | |
| ggt ggc ggt ggc ggt agt agc tct ggt agc tca agt ggt tct ggt ggt<br>Gly Gly Gly Gly Gly Ser Ser Ser Gly Ser Ser Ser Gly Ser Gly Gly<br>             300                       305                     310 | 1624 | |
| ggt agt tct agc ggt agt agt ggt ggt tct agc tca agc agc agc agc<br>Gly Ser Ser Ser Gly Ser Ser Gly Gly Ser Ser Ser Ser Ser Ser<br>315                      320                       325 | 1672 | |
| tcc tcg agc ggt ggt agc ggt gat tat aag gac gac gat gat aag gaa<br>Ser Ser Ser Gly Gly Ser Gly Asp Tyr Lys Asp Asp Asp Asp Lys Glu<br>             330                       335                     340 | 1720 | |
| gtt cag ctg gtt gaa tca ggt ggt ggt ctg gtt cag cct gga ggc tca<br>Val Gln Leu Val Glu Ser Gly Gly Gly Leu Val Gln Pro Gly Gly Ser<br>345                       350                       355                   360 | 1768 | |
| ctc cgt ttg tcc tgc gca gca tcc gga ttt aac att aaa gat acc tat<br>Leu Arg Leu Ser Cys Ala Ala Ser Gly Phe Asn Ile Lys Asp Thr Tyr<br>                  365                       370                     375 | 1816 | |
| atc cac tgg gtg cgt cag gct cct ggt aag ggc ctg gaa tgg gtt gcc<br>Ile His Trp Val Arg Gln Ala Pro Gly Lys Gly Leu Glu Trp Val Ala<br>             380                       385                     390 | 1864 | |
| cgt att tat cct acc aac ggc tat act cgt tat gcc gat agc gtc aag<br>Arg Ile Tyr Pro Thr Asn Gly Tyr Thr Arg Tyr Ala Asp Ser Val Lys<br>395                       400                       405 | 1912 | |
| ggt cgt ttt act ata agt gcg gat acc tct aaa aac acc gcg tac ctg<br>Gly Arg Phe Thr Ile Ser Ala Asp Thr Ser Lys Asn Thr Ala Tyr Leu<br>             410                       415                     420 | 1960 | |
| cag atg aac agt cta aga gcg gaa gat act gcc gtc tac tac tgc agc<br>Gln Met Asn Ser Leu Arg Ala Glu Asp Thr Ala Val Tyr Tyr Cys Ser<br>425                       430                       435                   440 | 2008 | |
| cgc tgg ggc ggc gat ggc ttt tac gcg atg gat tac tgg ggc cag gga<br>Arg Trp Gly Gly Asp Gly Phe Tyr Ala Met Asp Tyr Trp Gly Gln Gly<br>                  445                       450                     455 | 2056 | |
| act ttg gtt act gtt tcc agc gca agc acc aaa ggt ccg agc gtg ttt<br>Thr Leu Val Thr Val Ser Ser Ala Ser Thr Lys Gly Pro Ser Val Phe<br>             460                       465                     470 | 2104 | |

| | | | | | | | | | | | | | | | |
|---|---|---|---|---|---|---|---|---|---|---|---|---|---|---|---|
| ccg | ctg | gca | ccg | agc | agc | aaa | agc | acc | agc | ggt | ggc | acc | gca | gca | ctg | 2152
| Pro | Leu | Ala | Pro | Ser | Ser | Lys | Ser | Thr | Ser | Gly | Gly | Thr | Ala | Ala | Leu |
| | | 475 | | | | 480 | | | | 485 | | | | | |

| | | | | | | | | | | | | | | | |
|---|---|---|---|---|---|---|---|---|---|---|---|---|---|---|---|
| ggt | tgt | ctg | gtt | aaa | gat | tat | ttt | ccg | gaa | ccg | gtt | acc | gtt | agc | tgg | 2200
| Gly | Cys | Leu | Val | Lys | Asp | Tyr | Phe | Pro | Glu | Pro | Val | Thr | Val | Ser | Trp |
| | | 490 | | | | 495 | | | | 500 | | | | | |

| | | | | | | | | | | | | | | | |
|---|---|---|---|---|---|---|---|---|---|---|---|---|---|---|---|
| aat | agc | ggt | gca | ctg | acc | agc | ggt | gtt | cat | acc | ttt | ccg | gca | gtt | ctg | 2248
| Asn | Ser | Gly | Ala | Leu | Thr | Ser | Gly | Val | His | Thr | Phe | Pro | Ala | Val | Leu |
| 505 | | | | | 510 | | | | | 515 | | | | | 520 |

| | | | | | | | | | | | | | | | |
|---|---|---|---|---|---|---|---|---|---|---|---|---|---|---|---|
| cag | agc | agc | ggt | ctg | tat | agc | ctg | agt | agc | gtt | gtt | acc | gtt | ccg | agc | 2296
| Gln | Ser | Ser | Gly | Leu | Tyr | Ser | Leu | Ser | Ser | Val | Val | Thr | Val | Pro | Ser |
| | | | 525 | | | | 530 | | | | | 535 | | | |

| | | | | | | | | | | | | | | | |
|---|---|---|---|---|---|---|---|---|---|---|---|---|---|---|---|
| agc | agc | ctg | ggc | acc | cag | acc | tat | att | tgt | aat | gtt | aat | cat | aaa | ccg | 2344
| Ser | Ser | Leu | Gly | Thr | Gln | Thr | Tyr | Ile | Cys | Asn | Val | Asn | His | Lys | Pro |
| | | | 540 | | | | 545 | | | | | 550 | | | |

| | | | | | | | | | | | | | | | |
|---|---|---|---|---|---|---|---|---|---|---|---|---|---|---|---|
| agc | aat | acc | aaa | gtg | gat | aaa | aaa | gtt | gag | ccg | aaa | agc | tgt | ggt | ggt | 2392
| Ser | Asn | Thr | Lys | Val | Asp | Lys | Lys | Val | Glu | Pro | Lys | Ser | Cys | Gly | Gly |
| 555 | | | | | 560 | | | | | 565 | | | | | |

| | | | | | | | | | | | | | | | |
|---|---|---|---|---|---|---|---|---|---|---|---|---|---|---|---|
| cat | cat | cat | cac | cat | cat | ggt | ggt | ggg | ggt | ggt | ggt | ggt | agc | tca | tct | 2440
| His | His | His | His | His | His | Gly | Gly | Gly | Gly | Gly | Gly | Gly | Ser | Ser | Ser |
| | | 570 | | | | 575 | | | | 580 | | | | | |

| | | | | | | | | | | | | | | | |
|---|---|---|---|---|---|---|---|---|---|---|---|---|---|---|---|
| agc | ggt | ggg | gga | gga | gga | tca | gcg | gcc | cca | act | gat | ctt | cac | caa | acg | 2488
| Ser | Gly | Gly | Gly | Gly | Gly | Ser | Ala | Ala | Pro | Thr | Asp | Leu | His | Gln | Thr |
| 585 | | | | | 590 | | | | | 595 | | | | | 600 |

| | | | | | | | | | | | | | | | |
|---|---|---|---|---|---|---|---|---|---|---|---|---|---|---|---|
| tat | tac | cgc | cag | gta | aag | aac | ccg | aat | ccg | gtg | ttc | act | ccc | cgt | gaa | 2536
| Tyr | Tyr | Arg | Gln | Val | Lys | Asn | Pro | Asn | Pro | Val | Phe | Thr | Pro | Arg | Glu |
| | | | 605 | | | | 610 | | | | | 615 | | | |

| | | | | | | | | | | | | | | | |
|---|---|---|---|---|---|---|---|---|---|---|---|---|---|---|---|
| ggt | gcc | gga | acg | ctg | aag | ttc | tgc | gaa | aaa | ctg | atg | gaa | aag | gcg | gtg | 2584
| Gly | Ala | Gly | Thr | Leu | Lys | Phe | Cys | Glu | Lys | Leu | Met | Glu | Lys | Ala | Val |
| | | | 620 | | | | 625 | | | | | 630 | | | |

| | | | | | | | | | | | | | | | |
|---|---|---|---|---|---|---|---|---|---|---|---|---|---|---|---|
| ggc | ttc | acc | tcc | cgt | ttt | gat | ttc | gcc | att | cat | gtg | gcg | cat | gcc | cgt | 2632
| Gly | Phe | Thr | Ser | Arg | Phe | Asp | Phe | Ala | Ile | His | Val | Ala | His | Ala | Arg |
| | | 635 | | | | 640 | | | | 645 | | | | | |

| | | | | | | | | | | | | | | | |
|---|---|---|---|---|---|---|---|---|---|---|---|---|---|---|---|
| tcc | cgt | ggt | ctg | cgt | cgg | cgc | atg | cca | ccg | gtg | ctg | cgt | cga | cgg | gct | 2680
| Ser | Arg | Gly | Leu | Arg | Arg | Arg | Met | Pro | Pro | Val | Leu | Arg | Arg | Arg | Ala |
| | 650 | | | | 655 | | | | | 660 | | | | | |

| | | | | | | | | | | | | | | | |
|---|---|---|---|---|---|---|---|---|---|---|---|---|---|---|---|
| att | gat | gcg | ctg | ctg | cag | ggg | ctg | tgt | ttc | cac | tat | gac | ccg | ctg | gcc | 2728
| Ile | Asp | Ala | Leu | Leu | Gln | Gly | Leu | Cys | Phe | His | Tyr | Asp | Pro | Leu | Ala |
| 665 | | | | | 670 | | | | | 675 | | | | | 680 |

| | | | | | | | | | | | | | | | |
|---|---|---|---|---|---|---|---|---|---|---|---|---|---|---|---|
| aac | cgc | gtc | cag | tgt | tcc | atc | acc | aca | ctg | gcc | att | gag | tgc | gga | ctg | 2776
| Asn | Arg | Val | Gln | Cys | Ser | Ile | Thr | Thr | Leu | Ala | Ile | Glu | Cys | Gly | Leu |
| | | | 685 | | | | 690 | | | | | 695 | | | |

| | | | | | | | | | | | | | | | |
|---|---|---|---|---|---|---|---|---|---|---|---|---|---|---|---|
| gcg | aca | gag | tcc | ggt | gca | gga | aaa | ctc | tcc | atc | acc | cgt | gcc | acc | cgg | 2824
| Ala | Thr | Glu | Ser | Gly | Ala | Gly | Lys | Leu | Ser | Ile | Thr | Arg | Ala | Thr | Arg |
| | | | 700 | | | | 705 | | | | | 710 | | | |

| | | | | | | | | | | | | | | | |
|---|---|---|---|---|---|---|---|---|---|---|---|---|---|---|---|
| gcc | ctg | acg | ttc | ctg | tca | gag | ctg | gga | ctg | att | acc | tac | cag | acg | gaa | 2872
| Ala | Leu | Thr | Phe | Leu | Ser | Glu | Leu | Gly | Leu | Ile | Thr | Tyr | Gln | Thr | Glu |
| | | 715 | | | | 720 | | | | 725 | | | | | |

| | | | | | | | | | | | | | | | |
|---|---|---|---|---|---|---|---|---|---|---|---|---|---|---|---|
| tat | gac | ccg | ctt | atc | ggg | tgc | tac | att | ccg | acc | gac | atc | acg | ttc | aca | 2920
| Tyr | Asp | Pro | Leu | Ile | Gly | Cys | Tyr | Ile | Pro | Thr | Asp | Ile | Thr | Phe | Thr |
| | | 730 | | | | 735 | | | | 740 | | | | | |

| | | | | | | | | | | | | | | | |
|---|---|---|---|---|---|---|---|---|---|---|---|---|---|---|---|
| ctg | gct | ctg | ttt | gct | gcc | ctt | gat | gtg | tct | gag | gat | gca | gtg | gca | gct | 2968
| Leu | Ala | Leu | Phe | Ala | Ala | Leu | Asp | Val | Ser | Glu | Asp | Ala | Val | Ala | Ala |
| 745 | | | | | 750 | | | | | 755 | | | | | 760 |

| | | | | | | | | | | | | | | | |
|---|---|---|---|---|---|---|---|---|---|---|---|---|---|---|---|
| gcg | cgc | cgc | agt | cgt | gtt | gaa | tgg | gaa | aac | aaa | cag | cgc | aaa | aag | cag | 3016
| Ala | Arg | Arg | Ser | Arg | Val | Glu | Trp | Glu | Asn | Lys | Gln | Arg | Lys | Lys | Gln |
| | | | 765 | | | | 770 | | | | | 775 | | | |

| | | | | | | | | | | | | | | | |
|---|---|---|---|---|---|---|---|---|---|---|---|---|---|---|---|
| ggg | ctg | gat | acc | ctg | ggt | atg | gat | gag | ctg | ata | gcg | aaa | gcc | tgg | cgt | 3064
| Gly | Leu | Asp | Thr | Leu | Gly | Met | Asp | Glu | Leu | Ile | Ala | Lys | Ala | Trp | Arg |

|  |  |  |  |  |  |  |  |  |  |  |  |  |  |  |  |
|---|---|---|---|---|---|---|---|---|---|---|---|---|---|---|---|
| | | | | 780 | | | | | 785 | | | | | 790 | |

```
ttt gtg cgt gag cgt ttc cgc agt tac cag aca gag ctt cag tcc cgt       3112
Phe Val Arg Glu Arg Phe Arg Ser Tyr Gln Thr Glu Leu Gln Ser Arg
            795                 800                 805 gga ata aaa cgt gcc cgt gcg cgt cgt gat gcg aac aga gaa cgt cag       3160
Gly Ile Lys Arg Ala Arg Ala Arg Arg Asp Ala Asn Arg Glu Arg Gln
        810                 815                 820 gat atc gtc acc cta gtg aaa cgg cag ctg acg cgt gaa atc tcg gaa       3208
Asp Ile Val Thr Leu Val Lys Arg Gln Leu Thr Arg Glu Ile Ser Glu
825                 830                 835                 840 gga cgc ttc act gct aat ggt gag gcg gta aaa cgc gaa gtg gag cgt       3256
Gly Arg Phe Thr Ala Asn Gly Glu Ala Val Lys Arg Glu Val Glu Arg
                845                 850                 855 cgt gtg aag gag cgc atg att ctg tca cgt aac cgc aat tac agc cgg       3304
Arg Val Lys Glu Arg Met Ile Leu Ser Arg Asn Arg Asn Tyr Ser Arg
            860                 865                 870 ctg gcc aca gct tct ccc tgaaagtgat ctcctcagaa taatccggcc              3352
Leu Ala Thr Ala Ser Pro
        875 tgcgccggag gcatccgcac gcctgaagcc cgccggtgca caaaaaaaca gcgtcgcatg     3412 caaaaaacaa tctcatcatc caccttctgg agcatccgat tcccctgtt tttaatacaa      3472 aatacgcctc agcgacgggg aattttgctt atccacattt aactgcaagg gacttcccca     3532 taaggttaca accgttcatg tcataaagcg ccagccgcca gtcttacagg gtgcaatgta     3592 tcttttaaac acctgtttat atctccttta aactacttaa ttacattcat ttaaaaagaa     3652 aacctattca ctgcctgtcc tgtggacaga cagatatgca cctcccaccg caagcggcgg     3712 gccccgaccg gagccacttt agttacaaca cacaaaaaca acctccagaa aaacccggt      3772 ccagcgcaga accgaaacca caaagcccct ccctcataac tgaaaagcgg ccccgccccg     3832 gcccaagggg ccggaacaga gtcgctttta attatgaatg ttgtaactac atcttcatcg     3892 ctgtcagtct tctcgctgga agttctcagt acacgctcgt aagcggccct cacggcccgc     3952 taacgcggag acacgccccg acttcgggta accctcgtc gggaccactc cgaccgcgca      4012 cagaagctct ctcatggctg aaagcgggta tggtctggca gggctgggga tgggtaaggt     4072 gaaatctatc aatcagtacc ggcttacg                                        4100
```

<210> SEQ ID NO 71
<211> LENGTH: 878
<212> TYPE: PRT
<213> ORGANISM: Artificial sequence
<220> FEATURE:
<223> OTHER INFORMATION: Synthetic Construct

<400> SEQUENCE: 71

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95
```

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Asp Tyr Lys Asp Asp Asp Asp
            210                 215                 220

Lys Ser Gly Ser Ser Gly Ser Gly Ser Gly Ser Ser Ser Ser Gly Ser
225                 230                 235                 240

Ser Gly Gly Gly Ser Ser Ser Gly Ser Gly Gly Gly Gly Ser Ser
            245                 250                 255

Ser Gly Gly Gly Ser Ser Gly Ser Ser Gly Ser Ser Ser Ser Gly
            260                 265                 270

Ser Gly Ser Ser Gly Ser Gly Ser Ser Ser Gly Gly Gly Gly
            275                 280                 285

Ser Ser Ser Gly Ser Ser Ser Gly Gly Gly Gly Ser Ser Ser
            290                 295                 300

Gly Ser Ser Ser Gly Ser Gly Gly Ser Ser Gly Ser Ser Gly
305                 310                 315                 320

Gly Ser Ser Ser Ser Ser Ser Ser Ser Gly Gly Ser Gly Asp
            325                 330                 335

Tyr Lys Asp Asp Asp Asp Lys Glu Val Gln Leu Val Glu Ser Gly Gly
            340                 345                 350

Gly Leu Val Gln Pro Gly Gly Ser Leu Arg Leu Ser Cys Ala Ala Ser
            355                 360                 365

Gly Phe Asn Ile Lys Asp Thr Tyr Ile His Trp Val Arg Gln Ala Pro
370                 375                 380

Gly Lys Gly Leu Glu Trp Val Ala Arg Ile Tyr Pro Thr Asn Gly Tyr
385                 390                 395                 400

Thr Arg Tyr Ala Asp Ser Val Lys Gly Arg Phe Thr Ile Ser Ala Asp
            405                 410                 415

Thr Ser Lys Asn Thr Ala Tyr Leu Gln Met Asn Ser Leu Arg Ala Glu
            420                 425                 430

Asp Thr Ala Val Tyr Tyr Cys Ser Arg Trp Gly Gly Asp Gly Phe Tyr
            435                 440                 445

Ala Met Asp Tyr Trp Gly Gln Gly Thr Leu Val Thr Val Ser Ser Ala
            450                 455                 460

Ser Thr Lys Gly Pro Ser Val Phe Pro Leu Ala Pro Ser Ser Lys Ser
465                 470                 475                 480

Thr Ser Gly Gly Thr Ala Ala Leu Gly Cys Leu Val Lys Asp Tyr Phe
            485                 490                 495

Pro Glu Pro Val Thr Val Ser Trp Asn Ser Gly Ala Leu Thr Ser Gly
            500                 505                 510

Val His Thr Phe Pro Ala Val Leu Gln Ser Ser Gly Leu Tyr Ser Leu
515                 520                 525

Ser Ser Val Val Thr Val Pro Ser Ser Leu Gly Thr Gln Thr Tyr
530                 535                 540

Ile Cys Asn Val Asn His Lys Pro Ser Asn Thr Lys Val Asp Lys Lys
545                 550                 555                 560

Val Glu Pro Lys Ser Cys Gly His His His His His His Gly Gly
                565                 570                 575

Gly Gly Gly Gly Gly Ser Ser Ser Gly Gly Gly Gly Ser Ala
            580                 585                 590

Ala Pro Thr Asp Leu His Gln Thr Tyr Tyr Arg Gln Val Lys Asn Pro
            595                 600                 605

Asn Pro Val Phe Thr Pro Arg Glu Gly Ala Gly Thr Leu Lys Phe Cys
610                 615                 620

Glu Lys Leu Met Glu Lys Ala Val Gly Phe Thr Ser Arg Phe Asp Phe
625                 630                 635                 640

Ala Ile His Val Ala His Ala Arg Ser Arg Gly Leu Arg Arg Met
                645                 650                 655

Pro Pro Val Leu Arg Arg Arg Ala Ile Asp Ala Leu Leu Gln Gly Leu
            660                 665                 670

Cys Phe His Tyr Asp Pro Leu Ala Asn Arg Val Gln Cys Ser Ile Thr
            675                 680                 685

Thr Leu Ala Ile Glu Cys Gly Leu Ala Thr Glu Ser Gly Ala Gly Lys
690                 695                 700

Leu Ser Ile Thr Arg Ala Thr Arg Ala Leu Thr Phe Leu Ser Glu Leu
705                 710                 715                 720

Gly Leu Ile Thr Tyr Gln Thr Glu Tyr Asp Pro Leu Ile Gly Cys Tyr
                725                 730                 735

Ile Pro Thr Asp Ile Thr Phe Thr Leu Ala Leu Phe Ala Ala Leu Asp
            740                 745                 750

Val Ser Glu Asp Ala Val Ala Ala Arg Arg Ser Arg Val Glu Trp
            755                 760                 765

Glu Asn Lys Gln Arg Lys Lys Gln Gly Leu Asp Thr Leu Gly Met Asp
770                 775                 780

Glu Leu Ile Ala Lys Ala Trp Arg Phe Val Arg Glu Arg Phe Arg Ser
785                 790                 795                 800

Tyr Gln Thr Glu Leu Gln Ser Arg Gly Ile Lys Arg Ala Arg Ala Arg
                805                 810                 815

Arg Asp Ala Asn Arg Glu Arg Gln Asp Ile Val Thr Leu Val Lys Arg
            820                 825                 830

Gln Leu Thr Arg Glu Ile Ser Glu Gly Arg Phe Thr Ala Asn Gly Glu
            835                 840                 845

Ala Val Lys Arg Glu Val Glu Arg Val Lys Glu Arg Met Ile Leu
850                 855                 860

Ser Arg Asn Arg Asn Tyr Ser Arg Leu Ala Thr Ala Ser Pro
865                 870                 875

<210> SEQ ID NO 72
<211> LENGTH: 4106
<212> TYPE: DNA
<213> ORGANISM: Artificial sequence
<220> FEATURE:
<223> OTHER INFORMATION: Synthetic v10.1-TT construct
<220> FEATURE:
<221> NAME/KEY: CDS
<222> LOCATION: (689)..(3328)

-continued

```
<400> SEQUENCE: 72
cagttgatcg gcgcgagatt taatcgccgc gacaatttgc gacggcgcgt gcagggccag      60
actggaggtg gcaacgccaa tcagcaacga ctgtttgccc gccagttgtt gtgccacgcg     120
gttgggaatg taattcagct ccgccatcgc cgcttccact ttttcccgcg ttttcgcaga     180
aacgtggctg gcctggttca ccacgcggga acggtctga taagagacac cggcatactc      240
tgcgacatcg tataacgtta ctggtttcac attcaccacc tgaattgac tctcttccgg      300 gcgctatcat gccataccgc gaaaggtttt gcaccattcg gctagcgatg accctgctga     360
ttggttcgct gaccatttcc ggggtgcgga acggcgttac cagaaactca gaaggttcgt     420
ccaaccaaac cgactctgac ggcagtttac gagagagatg atagggtctg cttcagtaag     480
ccagatgcta cacaattagg cttgtacata ttgtcgttag aacgcggcta caattaatac     540
ataaccttat gtatcataca catacgattt aggtgacact atagaataca agcttactcc     600
ccatccccct gttgacaatt aatcatggct cgtataatgt gtggaattgt gagcggataa     660
caatttcaca caggaaacag gatctacc atg gat att cag atg acc cag agc         712
                                Met Asp Ile Gln Met Thr Gln Ser
                                  1               5 ccg agc agc ctg agc gca agc gtt ggt gat cgt gtt acc att acc tgt       760
Pro Ser Ser Leu Ser Ala Ser Val Gly Asp Arg Val Thr Ile Thr Cys
 10              15                  20 cgt gca agc cag gat att aaa aat tat ttg tct tgg tat caa caa caa       808
Arg Ala Ser Gln Asp Ile Lys Asn Tyr Leu Ser Trp Tyr Gln Gln Gln
 25              30                  35                  40 cca gga aat gcc ccg aag cca ctg att tat gct ggt tct aac cgc caa       856
Pro Gly Asn Ala Pro Lys Pro Leu Ile Tyr Ala Gly Ser Asn Arg Gln
             45                  50                  55 tct gga gtt cct tct cgc ttc tcc gga tct gga tct gaa act gat ttt       904
Ser Gly Val Pro Ser Arg Phe Ser Gly Ser Gly Ser Glu Thr Asp Phe
 60                  65                  70 act cta act att agt agt cta cag ccg gag gac ttc gcc acc tat tat       952
Thr Leu Thr Ile Ser Ser Leu Gln Pro Glu Asp Phe Ala Thr Tyr Tyr
         75                  80                  85 tgc caa caa act tac atc tac cct atc acc ttt ggc cag ggc acc aaa      1000
Cys Gln Gln Thr Tyr Ile Tyr Pro Ile Thr Phe Gly Gln Gly Thr Lys
 90                  95                 100 gtt gaa att aaa cgt acc gtt gca gca ccg agc gtt ttt att ttt ccg      1048
Val Glu Ile Lys Arg Thr Val Ala Ala Pro Ser Val Phe Ile Phe Pro
105                 110                 115                 120 cct agt gat gaa cag ctg aaa agc ggc acc gca agc gtt gtt tgt ctg      1096
Pro Ser Asp Glu Gln Leu Lys Ser Gly Thr Ala Ser Val Val Cys Leu
             125                 130                 135 ctg aat aat ttt tat ccg cgt gaa gca aaa gtg cag tgg aaa gtt gat      1144
Leu Asn Asn Phe Tyr Pro Arg Glu Ala Lys Val Gln Trp Lys Val Asp
                 140                 145                 150 aat gca ctg cag agc ggt aat agc caa gaa agc gtt acc gaa cag gat      1192
Asn Ala Leu Gln Ser Gly Asn Ser Gln Glu Ser Val Thr Glu Gln Asp
     155                 160                 165 agc aaa gat agc acc tat agc ctg agc agc acc ctg acc ctg agc aaa      1240
Ser Lys Asp Ser Thr Tyr Ser Leu Ser Ser Thr Leu Thr Leu Ser Lys
170                 175                 180 gca gat tat gaa aaa cac aaa gtg tat gcc tgc gaa gtt acc cat cag      1288
Ala Asp Tyr Glu Lys His Lys Val Tyr Ala Cys Glu Val Thr His Gln
185                 190                 195                 200 ggt ctg agc agt ccg gtt acc aaa agc ttt aat cgt ggt gaa tgc ggt      1336
Gly Leu Ser Ser Pro Val Thr Lys Ser Phe Asn Arg Gly Glu Cys Gly
```

-continued

|     | 205 |     |     |     |     | 210 |     |     |     |     | 215 |     |     |     |     |      |
|-----|-----|-----|-----|-----|-----|-----|-----|-----|-----|-----|-----|-----|-----|-----|-----|------|
| ggc | gat | tat | aaa | gat | gat | gat | gat | aaa | agc | ggt | agc | agc | ggt | agt | ggt | 1384 |
| Gly | Asp | Tyr | Lys | Asp | Asp | Asp | Asp | Lys | Ser | Gly | Ser | Ser | Gly | Ser | Gly |      |
|     |     |     | 220 |     |     |     |     | 225 |     |     |     |     | 230 |     |     |      | agc ggt agc agt agt agc ggt tca agc ggt ggt ggt agc agc agc tca   1432
Ser Gly Ser Ser Ser Ser Gly Ser Ser Gly Gly Gly Ser Ser Ser Ser
        235                 240                 245 ggt agt ggt ggt ggt ggt tca agc agc ggt ggt ggc agt agc ggt agc   1480
Gly Ser Gly Gly Gly Gly Ser Ser Ser Gly Gly Gly Ser Ser Gly Ser
250                 255                 260 tca agc ggt agc tct agc agc ggt tct ggt agc agt ggt tca ggt agt   1528
Ser Ser Gly Ser Ser Ser Ser Gly Ser Gly Ser Ser Gly Ser Gly Ser
265                 270                 275                 280 agc agc agc ggt ggc ggt ggt ggc tca agt agt ggt agc agc tca tca   1576
Ser Ser Ser Gly Gly Gly Gly Ser Ser Ser Gly Ser Ser Ser Ser
                285                 290                 295 ggt ggc ggt ggc ggt agt agc tct ggt agc tca agt ggt tct ggt ggt   1624
Gly Gly Gly Gly Gly Ser Ser Ser Gly Ser Ser Ser Gly Ser Gly Gly
                300                 305                 310 ggt agt tct agc ggt agt agt ggt ggt tct agc tca agc agc agc agc   1672
Gly Ser Ser Ser Gly Ser Ser Gly Gly Ser Ser Ser Ser Ser Ser Ser
            315                 320                 325 agt agc agt ggt ggt agc ggt gat tat aag gac gac gat gat aag gaa   1720
Ser Ser Ser Gly Gly Ser Gly Asp Tyr Lys Asp Asp Asp Asp Lys Glu
330                 335                 340 gtt cag ctg gtt gaa tca ggt ggt ggt ctg gtt cag cct ggt ggt agc   1768
Val Gln Leu Val Glu Ser Gly Gly Gly Leu Val Gln Pro Gly Gly Ser
345                 350                 355                 360 ctg cgt ctg agc tgt gca gca agc ggt ttt act att gaa cgt tat gcg   1816
Leu Arg Leu Ser Cys Ala Ala Ser Gly Phe Thr Ile Glu Arg Tyr Ala
                365                 370                 375 atg ggt tgg gtg cgt cag gct cct ggt aag ggc ctg gaa tgg gtt ggt   1864
Met Gly Trp Val Arg Gln Ala Pro Gly Lys Gly Leu Glu Trp Val Gly
            380                 385                 390 acg att tat cct tgg ggc gat tat act gat tat gcc gat agc gtc aag   1912
Thr Ile Tyr Pro Trp Gly Asp Tyr Thr Asp Tyr Ala Asp Ser Val Lys
        395                 400                 405 ggt cgt ttt act ata agt aga gat aat tct aaa aac acc ctc tac ctg   1960
Gly Arg Phe Thr Ile Ser Arg Asp Asn Ser Lys Asn Thr Leu Tyr Leu
    410                 415                 420 cag atg aac agt cta aga gat gaa gat act gcc gtc tac tac tgc gct   2008
Gln Met Asn Ser Leu Arg Asp Glu Asp Thr Ala Val Tyr Tyr Cys Ala
425                 430                 435                 440 cgc tct aac tac ccg aac ggt atg tac tac gtt atg gaa tat tgg ggt   2056
Arg Ser Asn Tyr Pro Asn Gly Met Tyr Tyr Val Met Glu Tyr Trp Gly
                445                 450                 455 cag ggc acc ctg gtt acc gtg agc agc gca agc acc aaa ggt ccg agc   2104
Gln Gly Thr Leu Val Thr Val Ser Ser Ala Ser Thr Lys Gly Pro Ser
            460                 465                 470 gtg ttt ccg ctg gca ccg agc agc aaa agc acc agc ggt ggc acc gca   2152
Val Phe Pro Leu Ala Pro Ser Ser Lys Ser Thr Ser Gly Gly Thr Ala
        475                 480                 485 gca ctg ggt tgt ctg gtt aaa gat tat ttt ccg gaa ccg gtt acc gtt   2200
Ala Leu Gly Cys Leu Val Lys Asp Tyr Phe Pro Glu Pro Val Thr Val
    490                 495                 500 agc tgg aat agc ggt gca ctg acc agc ggt gtt cat acc ttt ccg gca   2248
Ser Trp Asn Ser Gly Ala Leu Thr Ser Gly Val His Thr Phe Pro Ala
505                 510                 515                 520 gtt ctg cag agc agc ggt ctg tat agc ctg agt agc gtt gtt acc gtt   2296

|  |  |  |  |  |  |  |  |  |  |  |  |  |
|---|---|---|---|---|---|---|---|---|---|---|---|---|
| Val | Leu | Gln | Ser | Ser 525 | Gly | Leu | Tyr | Ser 530 | Leu | Ser | Ser | Val | Val | Thr 535 | Val |

```
ccg agc agc agc ctg ggc acc cag acc tat att tgt aat gtt aat cat    2344
Pro Ser Ser Ser Leu Gly Thr Gln Thr Tyr Ile Cys Asn Val Asn His
            540                 545                 550 aaa ccg agc aat acc aaa gtg gat aaa aaa gtt gag ccg aaa agc tgt    2392
Lys Pro Ser Asn Thr Lys Val Asp Lys Lys Val Glu Pro Lys Ser Cys
            555                 560                 565 ggt ggt cat cat cat cac cat cat ggt ggt ggg ggt ggt ggt ggt agc    2440
Gly Gly His His His His His His Gly Gly Gly Gly Gly Gly Gly Ser
            570                 575                 580 tca tct agc ggt ggg gga gga gga tca gcg gcc cca act gat ctt cac    2488
Ser Ser Ser Gly Gly Gly Gly Gly Ser Ala Ala Pro Thr Asp Leu His
585                 590                 595                 600 caa acg tat tac cgc cag gta aag aac ccg aat ccg gtg ttc act ccc    2536
Gln Thr Tyr Tyr Arg Gln Val Lys Asn Pro Asn Pro Val Phe Thr Pro
                605                 610                 615 cgt gaa ggt gcc gga acg ctg aag ttc tgc gaa aaa ctg atg gaa aag    2584
Arg Glu Gly Ala Gly Thr Leu Lys Phe Cys Glu Lys Leu Met Glu Lys
            620                 625                 630 gcg gtg ggc ttc acc tcc cgt ttt gat ttc gcc att cat gtg gcg cat    2632
Ala Val Gly Phe Thr Ser Arg Phe Asp Phe Ala Ile His Val Ala His
            635                 640                 645 gcc cgt tcc cgt ggt ctg cgt cgg cgc atg cca ccg gtg ctg cgt cga    2680
Ala Arg Ser Arg Gly Leu Arg Arg Arg Met Pro Pro Val Leu Arg Arg
650                 655                 660 cgg gct att gat gcg ctg ctg cag ggg ctg tgt ttc cac tat gac ccg    2728
Arg Ala Ile Asp Ala Leu Leu Gln Gly Leu Cys Phe His Tyr Asp Pro
665                 670                 675                 680 ctg gcc aac cgc gtc cag tgt tcc atc acc aca ctg gcc att gag tgc    2776
Leu Ala Asn Arg Val Gln Cys Ser Ile Thr Thr Leu Ala Ile Glu Cys
                685                 690                 695 gga ctg gcg aca gag tcc ggt gca gga aaa ctc tcc atc acc cgt gcc    2824
Gly Leu Ala Thr Glu Ser Gly Ala Gly Lys Leu Ser Ile Thr Arg Ala
            700                 705                 710 acc cgg gcc ctg acg ttc ctg tca gag ctg gga ctg att acc tac cag    2872
Thr Arg Ala Leu Thr Phe Leu Ser Glu Leu Gly Leu Ile Thr Tyr Gln
            715                 720                 725 acg gaa tat gac ccg ctt atc ggg tgc tac att ccg acc gac atc acg    2920
Thr Glu Tyr Asp Pro Leu Ile Gly Cys Tyr Ile Pro Thr Asp Ile Thr
            730                 735                 740 ttc aca ctg gct ctg ttt gct gcc ctt gat gtg tct gag gat gca gtg    2968
Phe Thr Leu Ala Leu Phe Ala Ala Leu Asp Val Ser Glu Asp Ala Val
745                 750                 755                 760 gca gct gcg cgc cgc agt cgt gtt gaa tgg gaa aac aaa cag cgc aaa    3016
Ala Ala Ala Arg Arg Ser Arg Val Glu Trp Glu Asn Lys Gln Arg Lys
                765                 770                 775 aag cag ggg ctg gat acc ctg ggt atg gat gag ctg ata gcg aaa gcc    3064
Lys Gln Gly Leu Asp Thr Leu Gly Met Asp Glu Leu Ile Ala Lys Ala
            780                 785                 790 tgg cgt ttt gtg cgt gag cgt ttc cgc agt tac cag aca gag ctt cag    3112
Trp Arg Phe Val Arg Glu Arg Phe Arg Ser Tyr Gln Thr Glu Leu Gln
            795                 800                 805 tcc cgt gga ata aaa cgt gcc cgt gcg cgt cgt gat gcg aac aga gaa    3160
Ser Arg Gly Ile Lys Arg Ala Arg Ala Arg Arg Asp Ala Asn Arg Glu
            810                 815                 820 cgt cag gat atc gtc acc cta gtg aaa cgg cag ctg acg cgt gaa atc    3208
Arg Gln Asp Ile Val Thr Leu Val Lys Arg Gln Leu Thr Arg Glu Ile
825                 830                 835                 840
```

```
tcg gaa gga cgc ttc act gct aat ggt gag gcg gta aaa cgc gaa gtg      3256
Ser Glu Gly Arg Phe Thr Ala Asn Gly Glu Ala Val Lys Arg Glu Val
                845                 850                 855 gag cgt cgt gtg aag gag cgc atg att ctg tca cgt aac cgc aat tac      3304
Glu Arg Arg Val Lys Glu Arg Met Ile Leu Ser Arg Asn Arg Asn Tyr
            860                 865                 870 agc cgg ctg gcc aca gct tct ccc tgaaagtgat ctcctcagaa taatccggcc     3358
Ser Arg Leu Ala Thr Ala Ser Pro
        875                 880 tgcgccggag gcatccgcac gcctgaagcc cgccggtgca caaaaaaaca gcgtcgcatg    3418
caaaaaacaa tctcatcatc caccttctgg agcatccgat tccccctgtt tttaatacaa    3478
aatacgcctc agcgacgggg aattttgctt atccacattt aactgcaagg gacttcccca    3538
taaggttaca accgttcatg tcataaagcg ccagccgcca gtcttacagg gtgcaatgta    3598 tctttttaaac acctgtttat atctccttta aactacttaa ttacattcat ttaaaaagaa   3658
aacctattca ctgcctgtcc tgtggacaga cagatatgca cctcccaccg caagcggcgg    3718
gccccgaccg gagccacttt agttacaaca cacaaaaaca acctcagaa aaaccccggt     3778 ccagcgcaga accgaaacca caaagcccct ccctcataac tgaaaagcgg ccccgccccg    3838
gcccaaaggg ccggaacaga gtcgctttta attatgaatg ttgtaactac atcttcatcg    3898
ctgtcagtct tctcgctgga agttctcagt acacgctcgt aagcggccct cacggcccgc    3958
taacgcggag cacgccccg acttcgggta aaccctcgtc gggaccactc cgaccgcgca     4018
cagaagctct ctcatggctg aaagcgggta tggtctggca gggctgggga tgggtaaggt    4078
gaaatctatc aatcagtacc ggcttacg                                        4106
```

<210> SEQ ID NO 73
<211> LENGTH: 880
<212> TYPE: PRT
<213> ORGANISM: Artificial sequence
<220> FEATURE:
<223> OTHER INFORMATION: Synthetic Construct

<400> SEQUENCE: 73

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Lys Asn
            20                  25                  30

Tyr Leu Ser Trp Tyr Gln Gln Pro Gly Asn Ala Pro Lys Pro Leu
        35                  40                  45

Ile Tyr Ala Gly Ser Asn Arg Gln Ser Gly Val Pro Ser Arg Phe Ser
    50                  55                  60

Gly Ser Gly Ser Glu Thr Asp Phe Thr Leu Thr Ile Ser Ser Leu Gln
65                  70                  75                  80

Pro Glu Asp Phe Ala Thr Tyr Tyr Cys Gln Gln Thr Tyr Ile Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
```

```
                165                 170                 175
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Asp Tyr Lys Asp Asp Asp Asp
    210                 215                 220

Lys Ser Gly Ser Gly Ser Gly Ser Gly Ser Ser Ser Ser Gly Ser
225                 230                 235                 240

Ser Gly Gly Gly Ser Ser Ser Gly Ser Gly Gly Gly Ser Ser
            245                 250                 255

Ser Gly Gly Gly Ser Ser Gly Ser Ser Ser Gly Ser Ser Ser Ser Gly
            260                 265                 270

Ser Gly Ser Ser Gly Ser Gly Ser Ser Ser Gly Gly Gly Gly
        275                 280                 285

Ser Ser Ser Gly Ser Ser Ser Gly Gly Gly Gly Ser Ser Ser
        290                 295                 300

Gly Ser Ser Ser Gly Ser Gly Gly Ser Ser Ser Gly Ser Ser Gly
305                 310                 315                 320

Gly Ser Ser Ser Ser Ser Ser Ser Ser Gly Gly Ser Gly Asp
                325                 330                 335

Tyr Lys Asp Asp Asp Asp Lys Glu Val Gln Leu Val Glu Ser Gly Gly
            340                 345                 350

Gly Leu Val Gln Pro Gly Gly Ser Leu Arg Leu Ser Cys Ala Ala Ser
        355                 360                 365

Gly Phe Thr Ile Glu Arg Tyr Ala Met Gly Trp Val Arg Gln Ala Pro
    370                 375                 380

Gly Lys Gly Leu Glu Trp Val Gly Thr Ile Tyr Pro Trp Gly Asp Tyr
385                 390                 395                 400

Thr Asp Tyr Ala Asp Ser Val Lys Gly Arg Phe Thr Ile Ser Arg Asp
                405                 410                 415

Asn Ser Lys Asn Thr Leu Tyr Leu Gln Met Asn Ser Leu Arg Asp Glu
            420                 425                 430

Asp Thr Ala Val Tyr Tyr Cys Ala Arg Ser Asn Tyr Pro Asn Gly Met
        435                 440                 445

Tyr Tyr Val Met Glu Tyr Trp Gly Gln Gly Thr Leu Val Thr Val Ser
    450                 455                 460

Ser Ala Ser Thr Lys Gly Pro Ser Val Phe Pro Leu Ala Pro Ser Ser
465                 470                 475                 480

Lys Ser Thr Ser Gly Gly Thr Ala Ala Leu Gly Cys Leu Val Lys Asp
                485                 490                 495

Tyr Phe Pro Glu Pro Val Thr Val Ser Trp Asn Ser Gly Ala Leu Thr
            500                 505                 510

Ser Gly Val His Thr Phe Pro Ala Val Leu Gln Ser Ser Gly Leu Tyr
        515                 520                 525

Ser Leu Ser Ser Val Val Thr Val Pro Ser Ser Ser Leu Gly Thr Gln
    530                 535                 540

Thr Tyr Ile Cys Asn Val Asn His Lys Pro Ser Asn Thr Lys Val Asp
545                 550                 555                 560

Lys Lys Val Glu Pro Lys Ser Cys Gly His His His His His His
                565                 570                 575

Gly Gly Gly Gly Gly Gly Gly Ser Ser Ser Gly Gly Gly Gly
            580                 585                 590
```

-continued

```
Ser Ala Ala Pro Thr Asp Leu His Gln Thr Tyr Tyr Arg Gln Val Lys
        595                 600             605
Asn Pro Asn Pro Val Phe Thr Pro Arg Glu Gly Ala Gly Thr Leu Lys
        610             615             620
Phe Cys Glu Lys Leu Met Glu Lys Ala Val Gly Phe Thr Ser Arg Phe
625             630             635             640
Asp Phe Ala Ile His Val Ala His Ala Arg Ser Arg Gly Leu Arg Arg
                645             650             655
Arg Met Pro Pro Val Leu Arg Arg Ala Ile Asp Ala Leu Leu Gln
            660             665             670
Gly Leu Cys Phe His Tyr Asp Pro Leu Ala Asn Arg Val Gln Cys Ser
        675             680             685
Ile Thr Thr Leu Ala Ile Glu Cys Gly Leu Ala Thr Glu Ser Gly Ala
        690             695             700
Gly Lys Leu Ser Ile Thr Arg Ala Thr Arg Ala Leu Thr Phe Leu Ser
705             710             715             720
Glu Leu Gly Leu Ile Thr Tyr Gln Thr Glu Tyr Asp Pro Leu Ile Gly
                725             730             735
Cys Tyr Ile Pro Thr Asp Ile Thr Phe Thr Leu Ala Leu Phe Ala Ala
            740             745             750
Leu Asp Val Ser Glu Asp Ala Val Ala Ala Arg Arg Ser Arg Val
        755             760             765
Glu Trp Glu Asn Lys Gln Arg Lys Lys Gln Gly Leu Asp Thr Leu Gly
    770             775             780
Met Asp Glu Leu Ile Ala Lys Ala Trp Arg Phe Val Arg Glu Arg Phe
785             790             795             800
Arg Ser Tyr Gln Thr Glu Leu Gln Ser Arg Gly Ile Lys Arg Ala Arg
            805             810             815
Ala Arg Arg Asp Ala Asn Arg Glu Arg Gln Asp Ile Val Thr Leu Val
            820             825             830
Lys Arg Gln Leu Thr Arg Glu Ile Ser Glu Gly Arg Phe Thr Ala Asn
        835             840             845
Gly Glu Ala Val Lys Arg Glu Val Glu Arg Arg Val Lys Glu Arg Met
    850             855             860
Ile Leu Ser Arg Asn Arg Asn Tyr Ser Arg Leu Ala Thr Ala Ser Pro
865             870             875             880
```

POLYNUCLEOTIDE CONSTRUCT CAPABLE OF DISPLAYING FAB IN A CELL-FREE TRANSLATION SYSTEM, AND METHOD FOR MANUFACTURING AND SCREENING FAB USING SAME

CROSS-REFERENCE TO RELATED APPLICATIONS

This patent application is a U.S. national phase of International Patent Application No. PCT/JP2011/077725, filed Nov. 30, 2011, which claims the benefit of Japanese Patent Application No. 2010-268763, filed on Dec. 1, 2010, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 177,305 bytes ASCII (Text) file named "713522Sequence-Listing.txt," created May 29, 2013.

TECHNICAL FIELD

The present invention relates to a polynucleotide construct that can display Fab in a cell-free translation system, a kit comprising the same, and a production method and a screening method for Fab using the same.

BACKGROUND ART

Antibodies are glycoproteins produced by B cells, and have the function to recognize molecules (antigens) such as proteins and bind thereto. Antibodies are produced in response to various internal and external stimuli (antigens), and cooperate with immunocompetent cells to eliminate bacteria and viruses that invaded the body, thereby playing an important role in the biological defense mechanism of vertebrates. A single type of B cell can produce only a single type of antibody, and a single type of antibody can recognize only a single type of antigen. In the human body, several millions to several hundred millions of types of B cells produce different antibodies to cope with numerous kinds of antigens. These are collectively called immunoglobulin, which is one of the most abundant proteins in the blood and constitutes 20% by weight of the total plasma proteins. Antibodies are utilized, based on their antigen specificities, as molecular-targeted agents and diagnostic agents.

A naturally-occurring antibody molecule forms a Y-shaped basic structure by association of two each of two types of polypeptide chains, the L chain (light chain) and the H chain (heavy chain). The lower half of the Y shape is composed of the Fc region, and the upper half of the Y shape, that is, the V-shaped portion, is composed of two identical Fab regions. The distal half of Fab is called the variable region (V region), and shows diversity in its amino acid sequence so that the antibodies can bind to various antigens. The variable regions in the L chain and the H chain are called VL and VH, respectively. On the other hand, the Fc-side half of Fab is called the constant region (C region), and shows less variability in its amino acid sequence. The constant regions in the L chain and the H chain are called CL and CH1, respectively. Each region in VL and VH that directly contacts with an antigen has especially high diversity in its amino acid sequence, and called the complementarity-determining region (CDR). The other part is called the framework region (FR). Each of VL and VH has 3 CDRs (CDR1 to CDR3), and 4 FRs (FR1 to FR4) surrounding these. The sequence diversity of CDR1 and CDR2 in naive B cells that have not been stimulated with an antigen is derived from the genomic DNA sequence (germline sequence). On the other hand, sequences of CDR3 are newly formed by recombination reaction of the genomic DNA that occurs in the process of differentiation of B cells, and hence its diversity is larger than those of the other CDRs. Moreover, in contrast to L-chain CDR3 formed by single recombination reaction (V-J recombination), H-chain CDR3 is formed through two times of recombination reaction (V-D recombination and D-J recombination), so that the H chain has a larger diversity in the same CDR3. The 6 CDRs form a single continuous surface involved in antigen binding in the distal part of Fab. In naturally-occurring antibodies, the functional and structural unit involved in antigen binding is Fab. While each of VL, VH, CL and CH1 constituting Fab forms an independent domain in terms of the spatial structure, they achieve high stability due to interactions among the 4 domains. Although the Fc region is not directly involved in binding of the antibody to an antigen, it is involved in various effector functions (e.g., the antibody-dependent cell-mediated cytotoxicity function).

Attempts are being made to prepare a gene library that expresses antibodies, in order to screen a gene encoding an antibody that specifically binds to a target antigen. In such a method, in order to obtain an antibody that specifically binds to a target antigen, an antibody library is expressed from DNA encoding the antibody library, and the expressed antibody library is brought into contact with the target antigen to select antibodies that specifically bind to the target antigen, followed by amplification of the DNAs encoding the selected antibodies. This cycle is repeated for screening antibodies. Since each antibody selected by such a screening method using a display technology is accompanied by information on the gene encoding its amino acid sequence, the selected antibody can be immediately prepared in a large amount by genetic engineering based on the genetic information encoding the antibody. Further, the amino acid sequence can also be easily determined by analysis of the genetic information.

An example of the antibody screening method using a display technology is phage display reported in 1985 by G. Smith et al. (Non-patent Document 1). Phage display is a technique in which a foreign protein is expressed as a fusion protein with mainly a coat protein of a filamentous phage, and the polynucleotide encoding the foreign protein of interest is selected. This method is widely used for, for example, selection of an antibody that specifically binds to an antigen molecule (Non-patent Documents 2 and 3). However, construction of a phage library requires the step of transformation of E. coli, and this step limits the size of the library. That is, due to the limit of efficiency of transformation of E. coli, construction of a library having a diversity of, for example, more than $10^{10}$ requires several ten times to several thousand times of transformation of E. coli by electroporation. Therefore, construction of a library larger than this is considered unrealistic. Further, since translation into a protein is dependent on E. coli, the efficiency of expression of a protein harmful to E. coli as a host is remarkably low.

On the other hand, cell-free display systems represented by ribosome display are techniques wherein proteins synthesized by a cell-free translation system are associated with polynucleotides encoding the proteins. Screening of an antibody using this system has been reported (Patent Document 1). However, what was actually prepared in this report is a single-chain antibody (scFv) wherein the heavy-chain variable region (VH) is linked to the light-chain variable region (VL) through a linker peptide, and no specific method for preparing Fab is disclosed. That is, it has been thought that Fab, which is constituted by two peptide chains and has a larger molecular weight than scFv, is difficult to be handled in ribosome display because, for example, ribosome display is generally a technique wherein a single molecule of RNA is coordinated with a single molecule of protein utilizing the 3'-end of the RNA, and synthesis of a full-length peptide chain becomes more difficult as the molecular weight of the protein to be synthesized increases (Non-patent Document 4). Further, since Fab is double-chained, the screening efficiency might decrease due to occurrence of not only cis-association of the H chain and the L chain displayed on the same RNA, but also trans-association of the H chain and the L chain on different RNAs.

As an attempt to use Fab in a cell-free display system, Yanagawa et al. reported a method wherein the H chain and the L chain constituting Fab are bicistronically expressed in a water-in-oil emulsion, and the Fab is associated with the DNA encoding it utilizing the interaction between streptavidin and biotin (Non-patent Document 4). However, since this method employs a water-in-oil emulsion, there are still problems in, for example, that the size of the library which can be handled is limited; that, since Fab synthesized in a compartment is once dissociated from DNA and mRNA and only one molecule of Fab is linked to the DNA, the remaining numerous Fab molecules cause competition; that the enrichment ratio is about 100, which is not very high; and that operations in the experiment require high skill.

Further, there is a known method called look-through mutagenesis for increasing the affinity of a target-substance-binding protein to its target substance, in which a library is prepared by introduction of a single amino acid substitution into a target-substance-binding site in a target-substance-binding protein, and the library is used to perform first screening, followed by combining the obtained single amino acid substitutions and performing second screening to screen mutant proteins having improved affinity to the target substance (Patent Document 2). However, in this method, the sequences obtained by the first screening are cloned, and mutant proteins are expressed from the obtained clones to confirm their affinity to the target substance, followed by performing the second screening. This is very laborious.

PRIOR ART DOCUMENTS

Patent Documents

[Patent Document 1] JP 2008-271903 A
[Patent Document 2] JP 2011-182794 A

Non-Patent Documents

[Non-patent Document 1] G. P. Smith et al. (1985) Science, vol. 228, p. 1315-1317
[Non-patent Document 2] J. McCafferty et al., Nature (1990) vol. 348, p. 552-554
[Non-patent Document 3] M. Hust et al., BMC Biotechnology, 2007, 7:14
[Non-patent Document 4] T. Sumida et al., Nucleic Acid Research, 2009, 37: 22, 147

SUMMARY OF THE INVENTION

Although screening of antibodies using the display technology has already been carried out as described above, it has been considered that efficient screening of Fab having a large molecular weight and composed of two peptide chains is difficult with a cell-free display system such as ribosome display. In view of this, the present invention aims to provide a method wherein Fab is efficiently expressed in a cell-free translation system such as ribosome display and coordinated with the polynucleotide encoding it in order to perform screening, and to provide a polynucleotide construct therefor.

The present inventors intensively studied to solve the above problems. As a result, the present inventors discovered that Fab can be efficiently screened in a cell-free translation system by preparing a polynucleotide construct for bicistronic expression of the Fab H chain and the Fab L chain associated with their respective nucleotide sequence information or a polynucleotide construct for monocistronic expression of the Fab H chain and the Fab L chain associated with their nucleotide sequence information, and performing ribosome display and/or CIS display using it; and further discovered the Ymacs method, wherein the affinity of an antibody is remarkably improved by using this cell-free Fab display system, thereby completed the present invention.

That is, the present invention provides the followings:
(Polynucleotide Construct to be used for Cell-Free Display Method of Fab)
[1] A polynucleotide construct comprising a Fab first chain-coding sequence and a Fab second chain-coding sequence, wherein said polynucleotide construct expresses a Fab encoded by itself without dissociation, and maintains a complex with the Fab, when it is introduced into a cell-free translation system containing ribosomes.
(Polynucleotide Construct (Monocistronic))
[2] The polynucleotide construct according to [1], wherein said polynucleotide construct monocistronically comprises a ribosome-binding sequence, Fab first chain-coding sequence, linker peptide-coding sequence, Fab second chain-coding sequence and scaffold-coding sequence in this order, and further comprises at its 3'-end a structure necessary for maintaining a complex with the Fab encoded by itself.
(Polynucleotide Construct (Bicistronic))
[3] The polynucleotide construct according to [1], wherein said polynucleotide construct comprises a Fab first chain-expressing cistron and a Fab second chain-expressing cistron each containing a ribosome-binding sequence, a Fab first chain-coding sequence or Fab second chain-coding sequence, and a scaffold-coding sequence in this order, said first Fab-expressing cistron further comprising at its 3'-end a ribosome stall sequence, said Fab second chain-expressing cistron further comprising at its 3'-end a structure necessary for maintaining a complex with the Fab encoded by itself.
(Polynucleotide Construct to be used for Ribosome/mRNA/CIS Display Method)
[4] The polynucleotide construct according to [2] or [3], wherein said structure necessary for maintaining a complex with the Fab encoded by itself is a ribosome stall sequence, puromycin or a derivative thereof, or a DNA-binding protein-coding sequence and a binding sequence for said DNA-binding protein.
(Polynucleotide Construct to be used for Ribosome Display Method)
[5] The polynucleotide construct according to [4], wherein said structure necessary for maintaining a complex with the Fab encoded by itself is a ribosome stall sequence.
[6] The polynucleotide construct according to [5], wherein said ribosome stall sequence is a SecM sequence, diproline sequence, or both of them.

[7] The polynucleotide construct according to [5] or [6], wherein said ribosome stall sequence is composed of 2 to 4 repeats of the SecM sequence.

[8] The polynucleotide construct according to any one of [4] to [7], wherein a stop codon is present in the 3'-side of said ribosome stall sequence.

(Polynucleotide Construct to be used for mRNA Display Method)

[9] The polynucleotide construct according to [4], wherein said structure necessary for maintaining a complex with the Fab encoded by itself is puromycin or a derivative thereof (Polynucleotide Construct to be used for CIS Display Method)

[10] The polynucleotide construct according to [4], wherein said structure necessary for maintaining a complex with the Fab encoded by itself is a DNA-binding protein-coding sequence and a binding sequence for said DNA-binding protein.

[11] The polynucleotide construct according to [10], wherein said DNA-binding protein is a cis-binding protein which is never dissociated during transcription/translation reaction from the DNA molecule used as a template for said transcription/translation and which binds to said binding sequence for the DNA-binding protein located in the same DNA molecule.

[12] The polynucleotide construct according to [10], wherein said DNA-binding protein is RepA encoded by *Escherichia coli* R1 plasmid and said binding sequence for the DNA-binding protein is a CIS-ori sequence located downstream of the RepA-coding sequence in the same polynucleotide.

[13] The polynucleotide construct according to any one of [1] to [12], wherein said polynucleotide construct is a library wherein said Fab first chain-coding sequence and said Fab second chain-coding sequence comprise random sequences.

[14] The polynucleotide construct according to [13], wherein said library comprising random sequences is a (i) naive library or (ii) focused library.

[15] The polynucleotide construct according to [13] or [14], wherein said library comprising random sequences is a library comprising single amino acid substitutions in the complementarity-determining region(s) (CDR(s)) of the Fab first chain and/or the Fab second chain.

[16] A method for screening a Fab, said method comprising the steps of
  (i) introducing the polynucleotide construct according to any one of [1] to [15] into a cell-free translation system to synthesize Fabs, and displaying said synthesized Fabs on the polynucleotides encoding said Fabs;
  (ii) bringing said Fabs displayed on said polynucleotides into contact with an antigen;
  (iii) selecting a Fab of interest that reacts with said antigen; and
  (iv) amplifying the polynucleotide encoding said Fab of interest.

[17] The method for screening a Fab according to [16], said method comprising the steps of:
  (I) providing a plurality of types of the polynucleotide construct according to [15], in each of which the Fab first chain-coding sequence or the Fab second chain-coding sequence encodes an amino acid sequence comprising a single amino acid substitution at a single position in a CDR in the amino acid sequence of the Fab first chain or the Fab second chain of the parent antibody, such that single amino acid substitutions are contained for a plurality of positions in the CDRs of the Fab first chain and the Fab second chain;
  (II) carrying out first screening wherein said steps (i) to (iv) are repeated using said plurality of types of the polynucleotide construct, to screen a plurality of high-affinity Fabs;
  (III) analyzing single amino acid substitutions at respective positions in the CDRs of the Fab first chain and the Fab second chain in said plurality of Fabs selected in said first screening step;
  (IV) providing the polynucleotide construct according to [15] wherein the Fab first chain-coding sequence and the Fab second chain-coding sequence encode amino acid sequences comprising combinations of the single amino acid substitutions identified in said first screening at said respective positions in the CDRs of the Fab first chain and Fab second chain sequences of the parent antibody; and
  (V) carrying out second screening wherein said steps (i) to (iv) are repeated using said polynucleotide construct, to screen a high-affinity Fab.

[18] The method according to [16] or [17], wherein said in vitro translation system is composed of factors independently purified.

[19] The method according to [18], wherein said in vitro translation system contains at least one component selected from the group consisting of initiation factors, elongation factors, aminoacyl-tRNA synthetase and methionyl-tRNA transformylase.

[20] The method according to [18] or [19] wherein said in vitro translation system does not contain a releasing factor.

[21] The method according to [16] or [17], wherein said in vitro translation system is a cell extract containing ribosomes.

[22] A method for producing a Fab, said method comprising the step of introducing the polynucleotide construct according to any one of [1] to [15] into an in vitro translation system to produce a Fab.

[23] A kit for producing or screening a Fab, said kit comprising the polynucleotide construct according to any one of [1] to [15].

[24] A method for maximizing the affinity of a target-substance-binding protein to a target substance, said method comprising the steps of
  (I) constructing single-position libraries wherein one amino acid among all amino acid positions constituting a target-substance-binding site in a target-substance-binding protein is randomized to all the 20 types of naturally-occurring amino acids, to provide as many single-position libraries as the number of the all amino acid positions;
  (II) constructing a primary library by integrating all of, or an appropriate unit of, these single-position libraries;
  (III) selecting said primary library using a protein display system based on the affinity to a target;
  (IV) determining the polynucleotide sequence information of said selected sample of the primary library;
  (V) extracting single amino acid substitutions frequently observed in said nucleotide sequence information;
  (VI) constructing a secondary library comprising combinations of said frequently observed single amino acid substitutions; and
  (VII) selecting said secondary library using a protein display system based on the affinity to a target.

[25] The method according to [24], wherein the step of determining the polynucleotide sequence information of said selected sample of the primary library is carried out using a next-generation sequencer.

[26] The method according to [24] or [25], wherein said target-substance-binding protein is a full-length antibody or an antibody fragment and said target-substance-binding site is a CDR region.

[27] The method according to any one of [24] to [26], wherein said protein display system is ribosome display, CIS display, mRNA display, phage display, bacterial surface display, yeast cell surface display, or cell surface display with a higher eukaryote.

According to the present invention, a Fab of interest can be screened by efficiently expressing Fab without dissociation from the polynucleotide in a cell-free display system. Since the method of the present invention can be carried out in a cell-free translation system, the operation is simple, and the screening can be carried out in a short period. A large-scale library with a level of not less than $10^{12}$ can be easily constructed, and, by this, highly efficient screening is possible. Further, according to the Ymacs method of the present invention, a large number of Fabs having several hundred to not less than a thousand times higher affinity to an antigen can be obtained as compared to error prone PCR, CDR shuffling and the like.

BRIEF DESCRIPTION OF THE DRAWINGS

In the figures, the symbols on mRNA and DNA represent the followings:

"VL", coding sequence in the L chain variable region of Fab;

"CL", coding sequence in the L chain constant region of Fab;

"VH", coding sequence in the H chain variable region of Fab;

"CH1", coding sequence in the H chain constant region of Fab;

"Linker", coding sequence of the linker peptide;

"RBS (○)", ribosome-binding site;

"Pu", puromycin or a derivative thereof

"Pro Δ", promoter;

"RNAP", RNA polymerase;

"RSS(S)", ribosome stall sequence; and

"LP(P)", leader peptide sequence for secretory expression.

Figure 1:
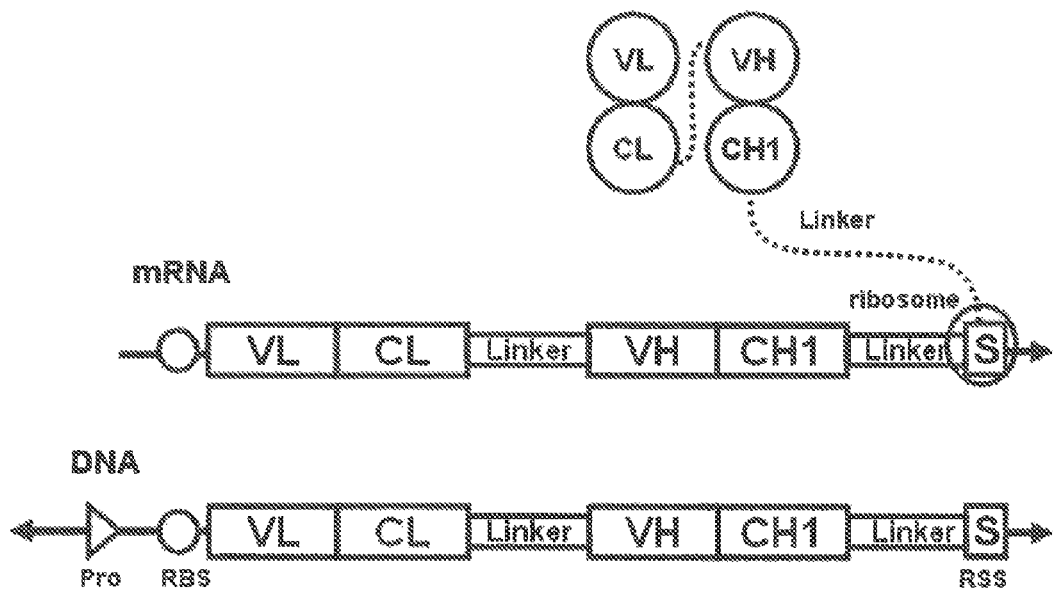

FIG. 1 is a schematic diagram showing display of Fab on a monocistronic polynucleotide construct (an embodiment utilizing ribosome display) (RBS (○) represents the ribosome-binding site; the same applies hereinafter).

Figure 2:
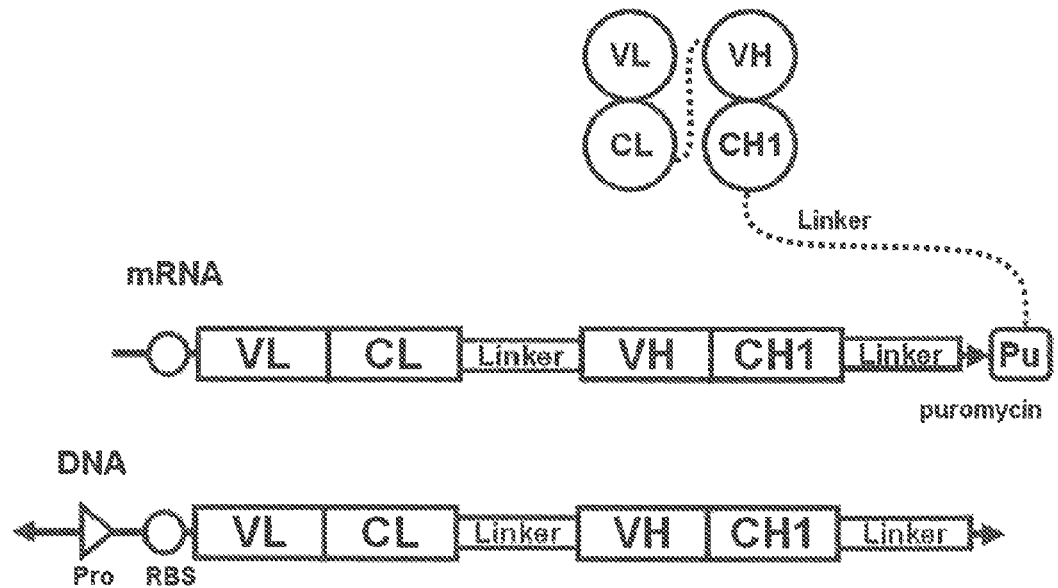

FIG. 2 is schematic diagram showing display of Fab on a monocistronic polynucleotide construct (an embodiment utilizing mRNA display).

Figure 3:
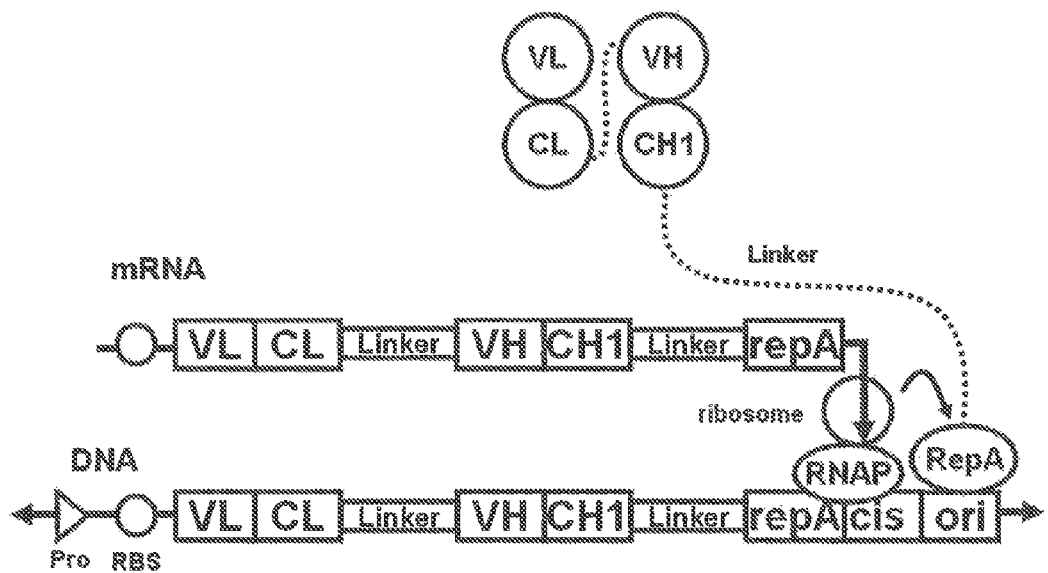

FIG. 3 is schematic diagram showing display of Fab on a monocistronic polynucleotide construct (an embodiment utilizing CIS display) (Δ represents a promoter; the same applies hereinafter).

Figure 4:
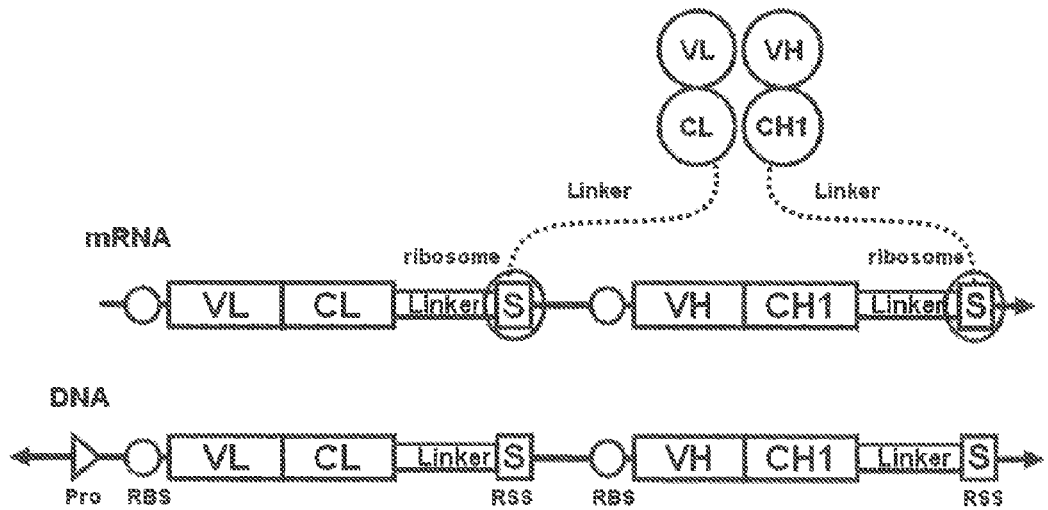

FIG. 4 is a schematic diagram showing display of Fab on a bicistronic polynucleotide construct (an embodiment utilizing ribosome display for both the 5'-side cistron and the 3'-side cistron).

Figure 5:
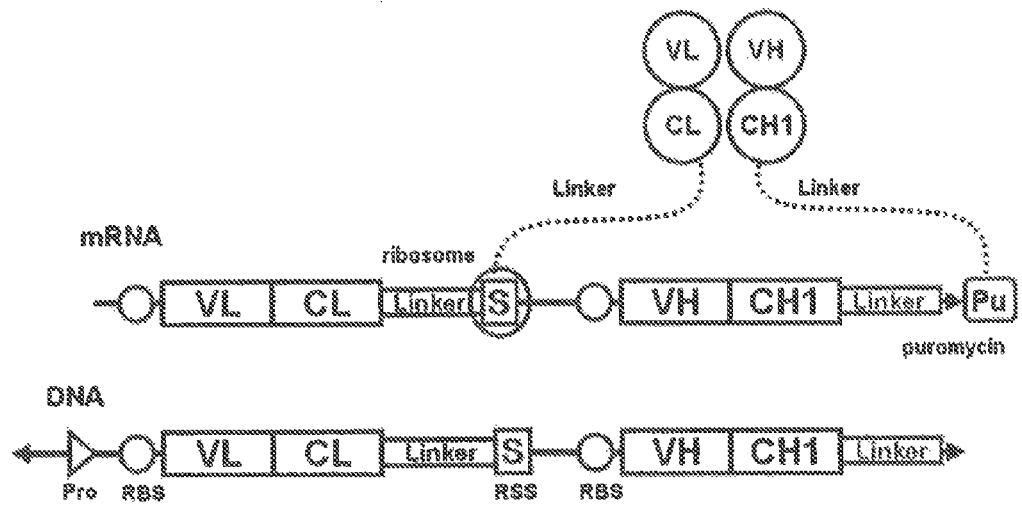

FIG. 5 is a schematic diagram showing display of Fab on a bicistronic polynucleotide construct (an embodiment utilizing ribosome display for the 5'-side cistron and utilizing mRNA display for the 3'-side cistron).

Figure 6:
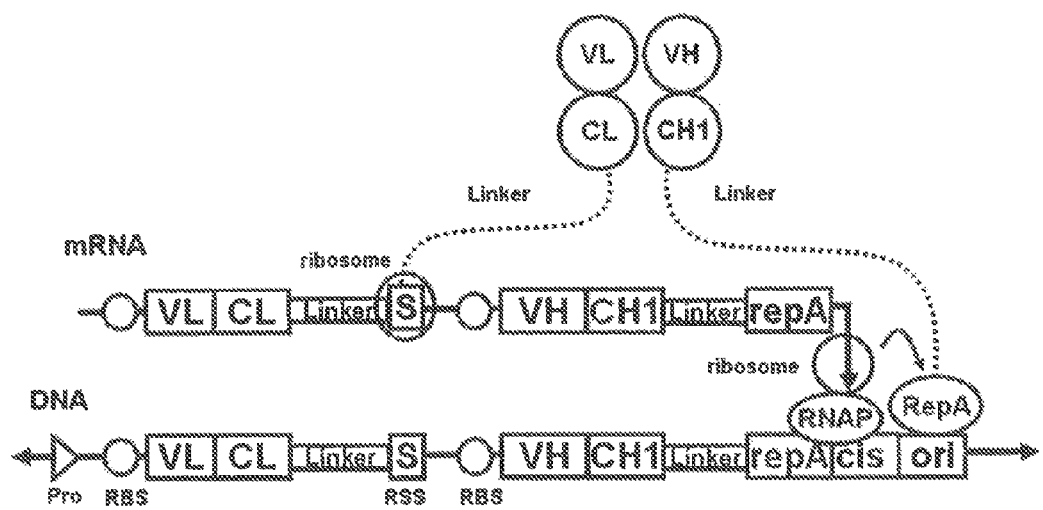

FIG. 6 is a schematic diagram showing display of Fab on a bicistronic polynucleotide construct (an embodiment utilizing ribosome display for the 5'-side cistron and utilizing CIS display for the 3'-side cistron).

Figure 7:
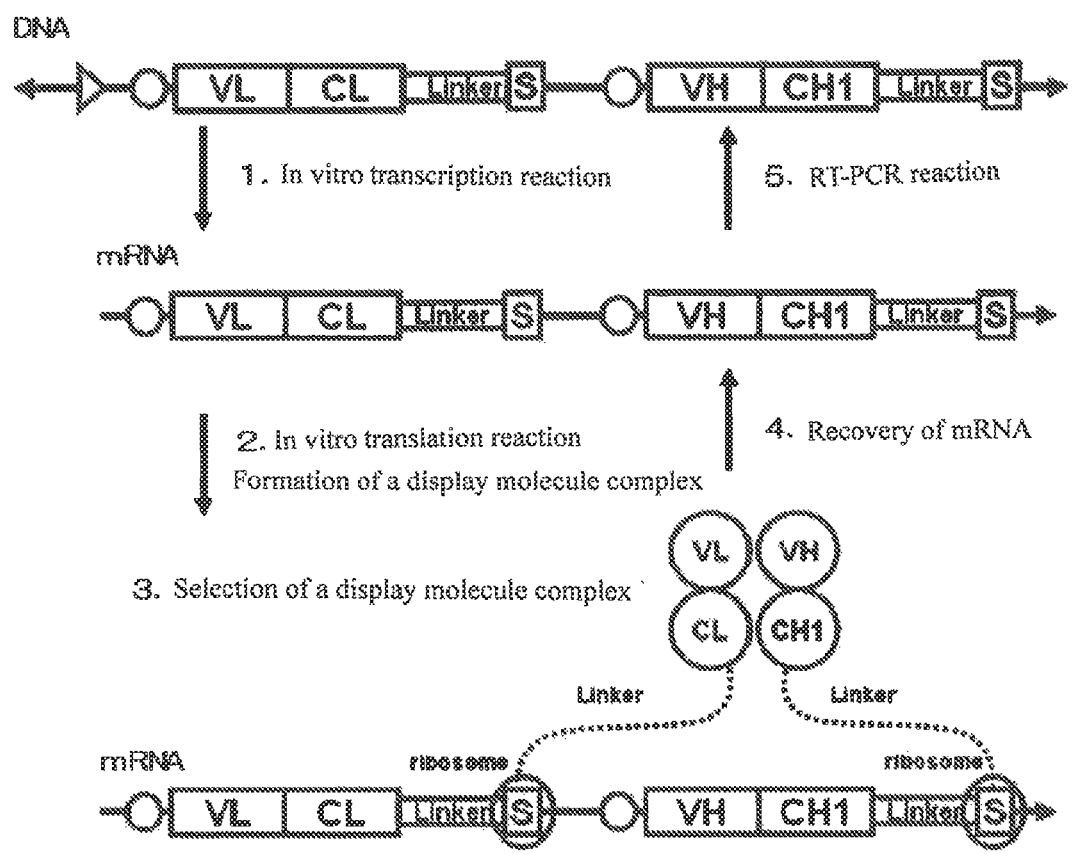

FIG. 7 is a schematic diagram showing a method for screening (ribosome display) of Fab.

Figure 8:
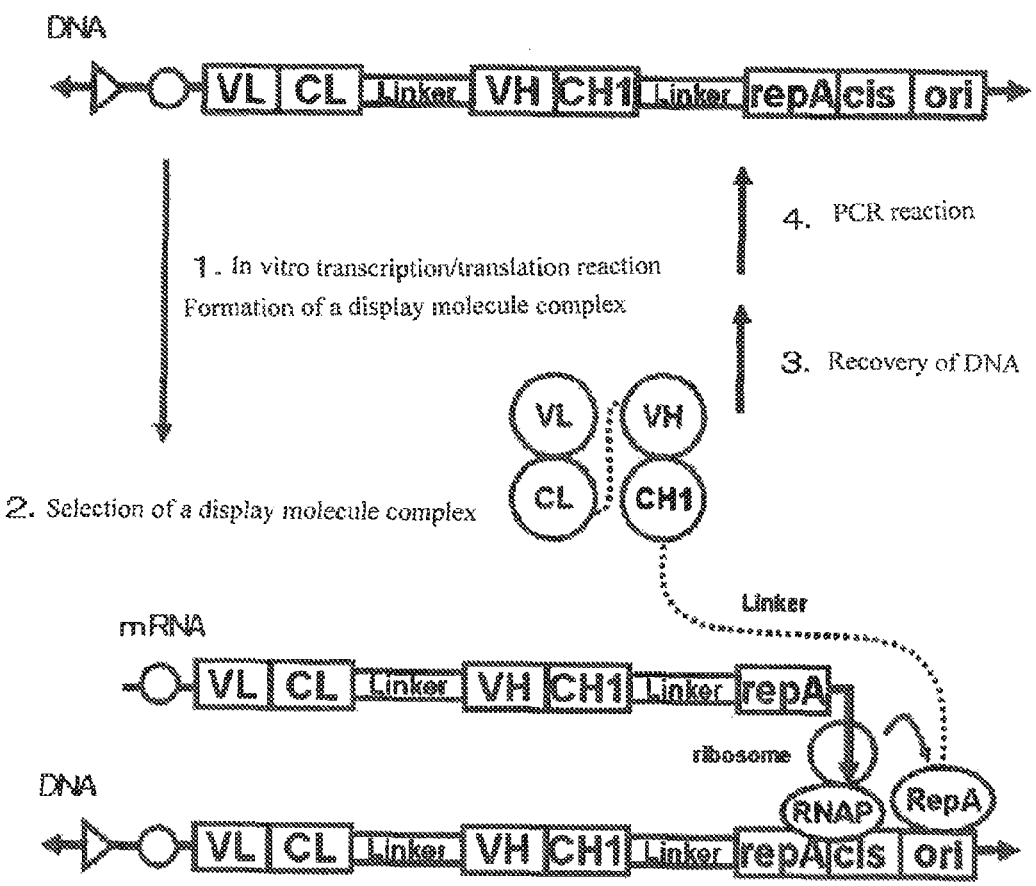

FIG. 8 is a schematic diagram showing a method for screening (CIS display) of Fab.

Figure 9:
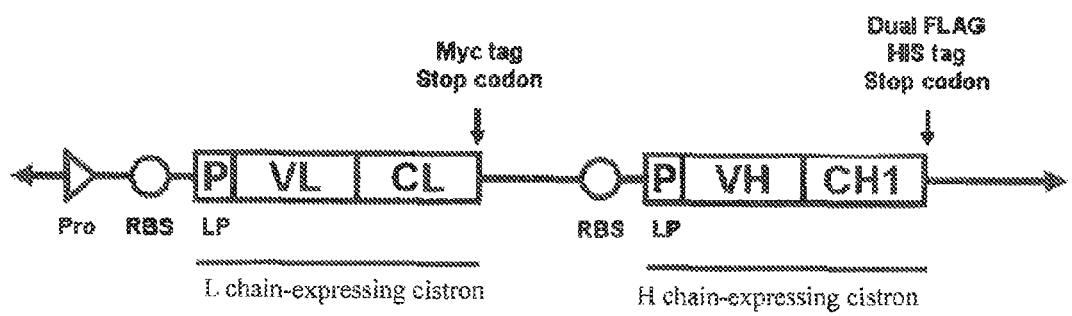

FIG. 9 is a schematic diagram showing a pTrc-Fab bicistronic Fab secretory expression unit.

Figure 10:
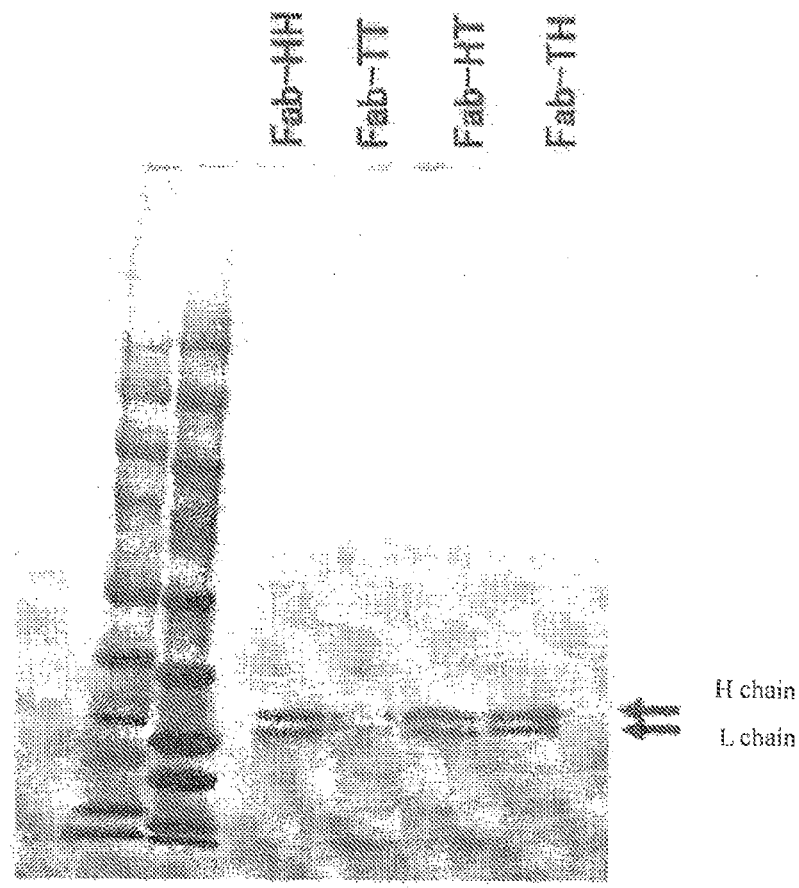

FIG. 10 is a photograph showing staining of model Fabs with CBB. The two lanes in the left side show markers.

Figure 11:
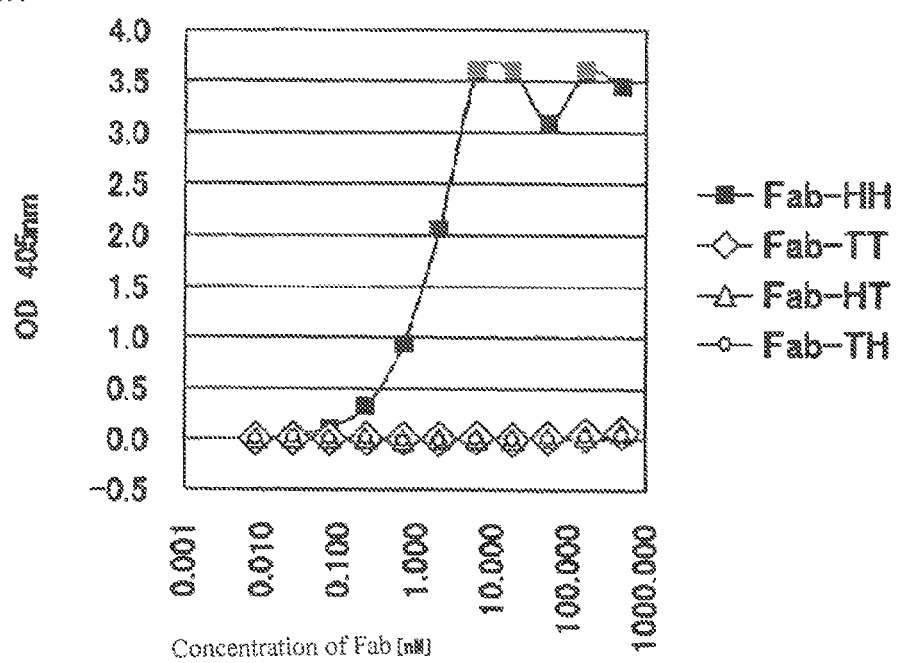

FIG. 11 is a graph showing the result of ELISA (low concentration, Her2 antigen) of model Fabs.

Figure 12:
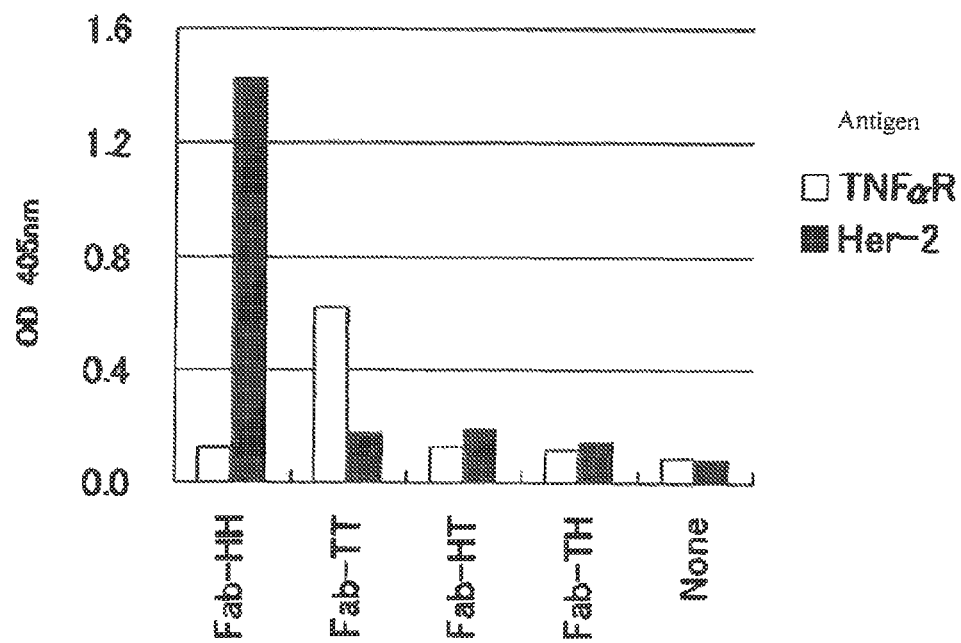

FIG. 12 is a graph showing the result of ELISA (high concentration) of model Fabs.

Figure 13:
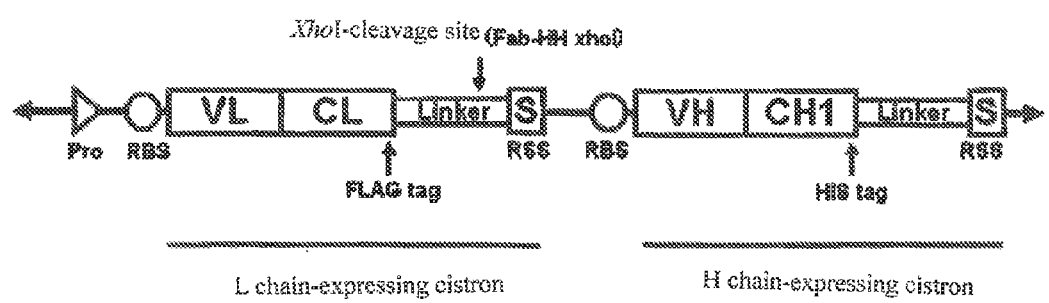

FIG. 13 is a schematic diagram showing a DNA fragment for bicistronic Fab-PRD (polynucleotide construct). RSS represents a ribosome stall sequence (the same applies to FIG. 14).

Figure 14:
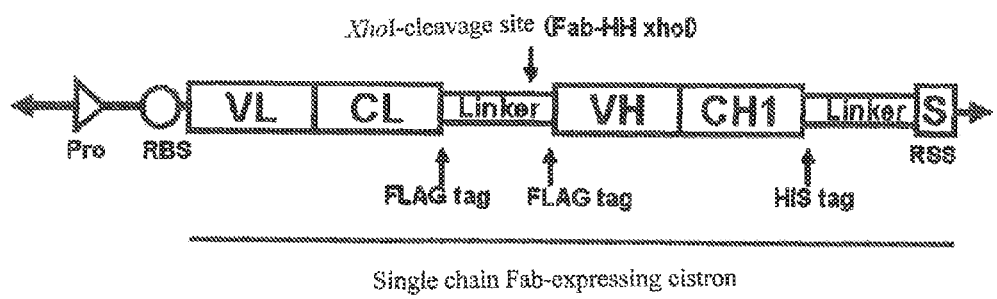

FIG. 14 is a schematic diagram showing a DNA fragment for monocistronic Fab-PRD (polynucleotide construct).

Figure 15:
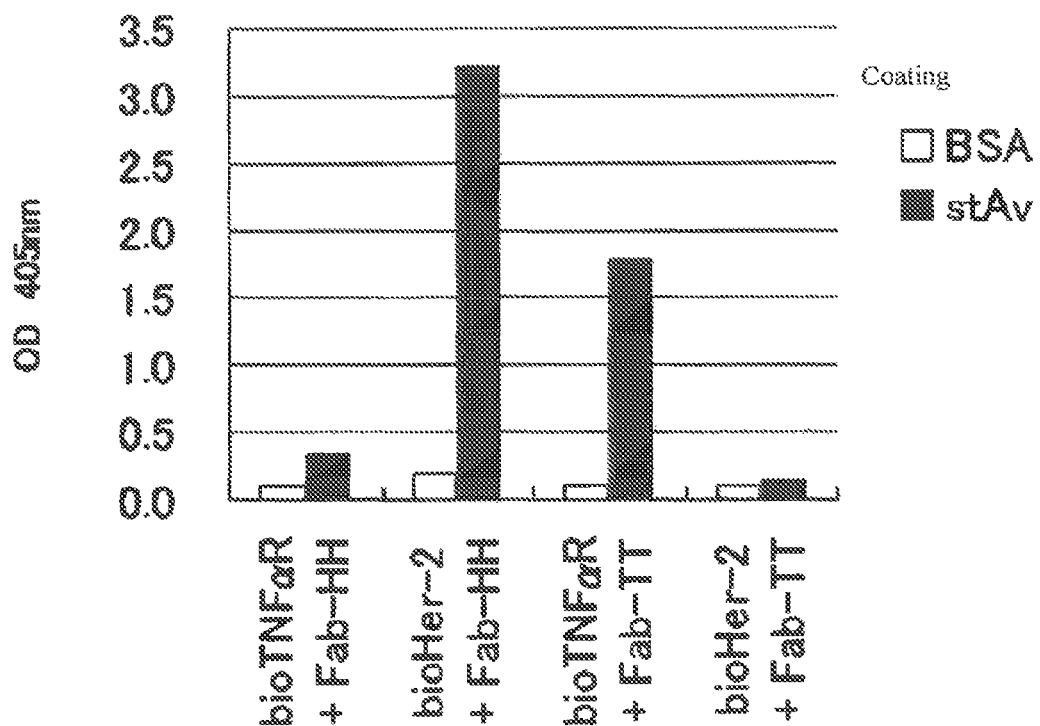

FIG. 15 is a graph showing the result of evaluation of biotinylated antigens by sandwich ELISA BSA represents bovine serum albumin (control), and stAv represents streptavidin.

Figure 16:
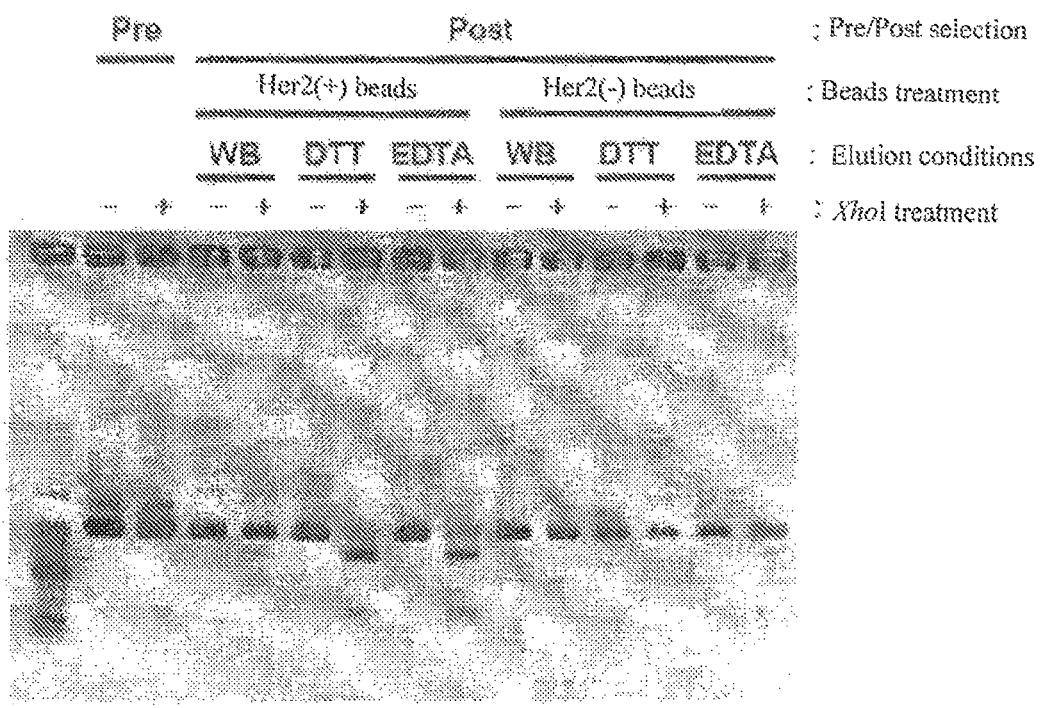

FIG. 16 is an electrophoretogram showing the result of Fab-HHxho enrichment in bicistronic Fab-PRD (for only the middle portion). WB represents a washing buffer.

Figure 17:
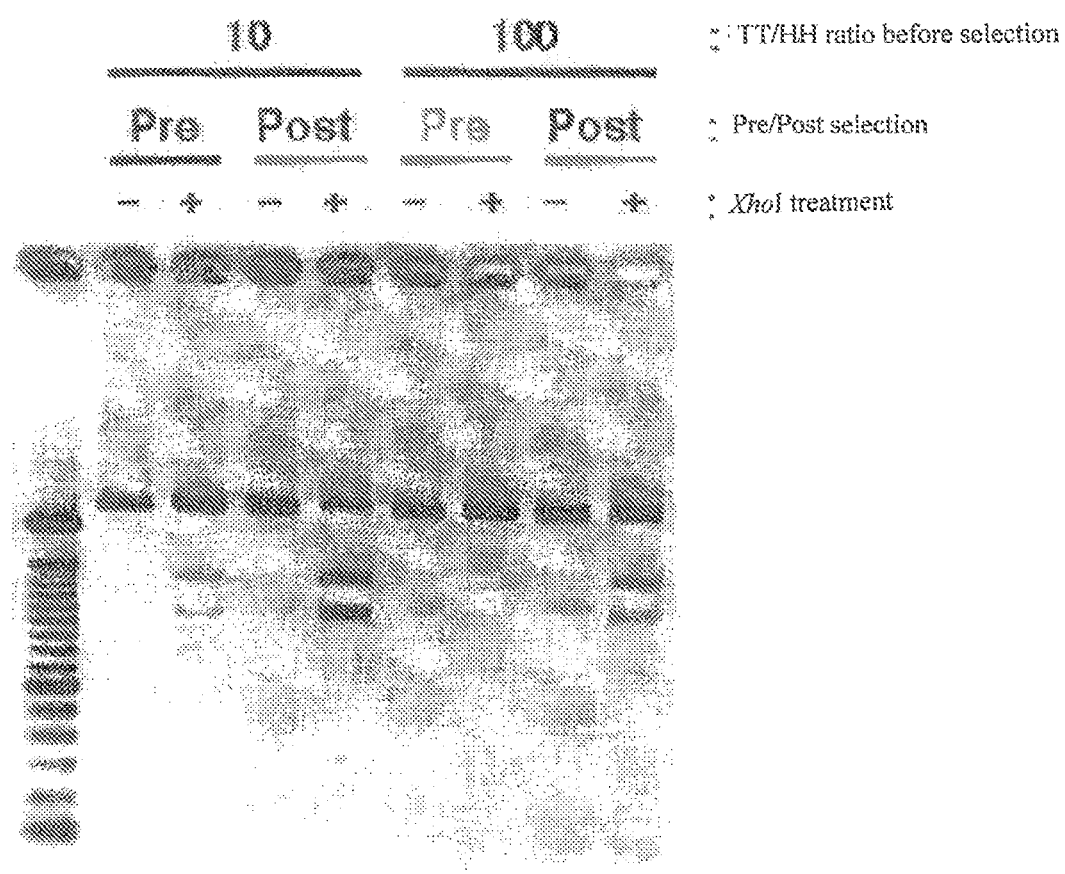

FIG. 17 is an electrophoretogram showing the result of Fab-HHxho enrichment in bicistronic Fab-PRD (for the full-length sequence).

Figure 18:
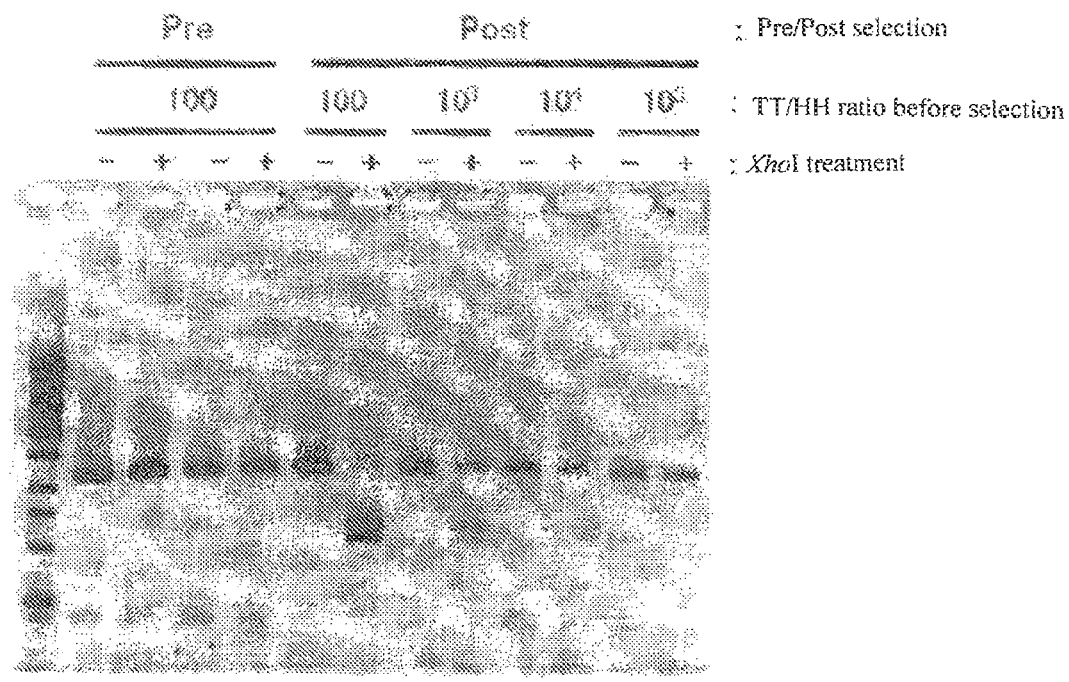

FIG. 18 is an electrophoretogram showing the result of Fab-HHxho enrichment in monocistronic Fab-PRD (for the full-length sequence).

Figure 19:
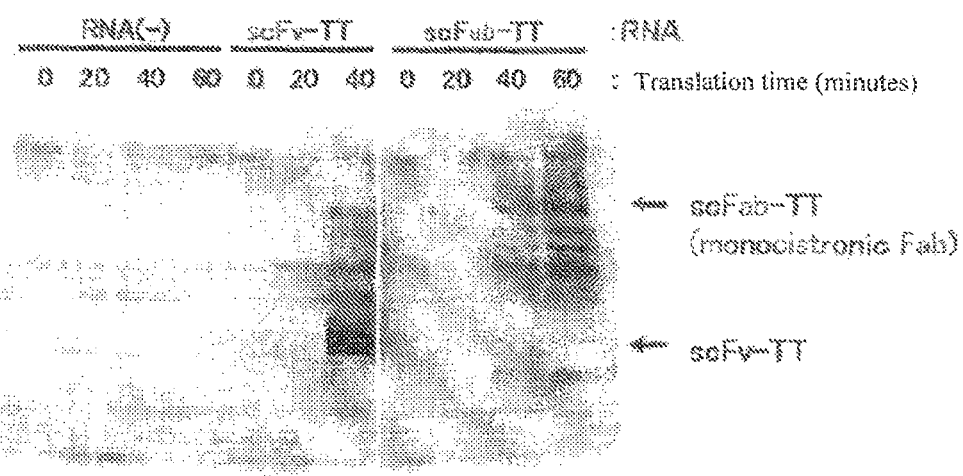

FIG. 19 is an electrophoretogram (Western blot) showing the result of detection of in vitro translation products of monocistronic Fab-PRD.

Figure 20:
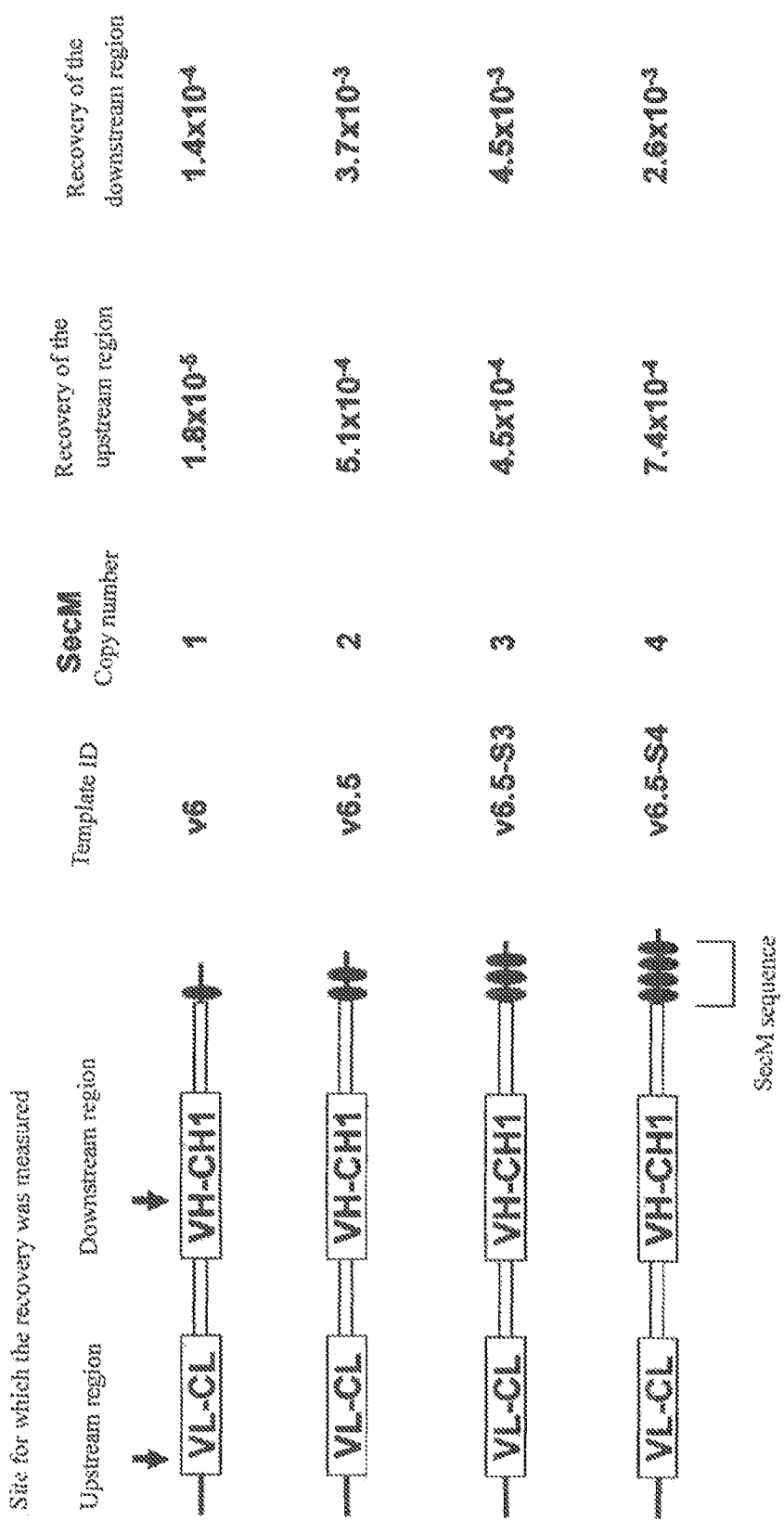

FIG. 20 is a diagram showing the relationship between the copy number of SecM and the recovery in monocistronic Fab-PRD.

Figure 21:
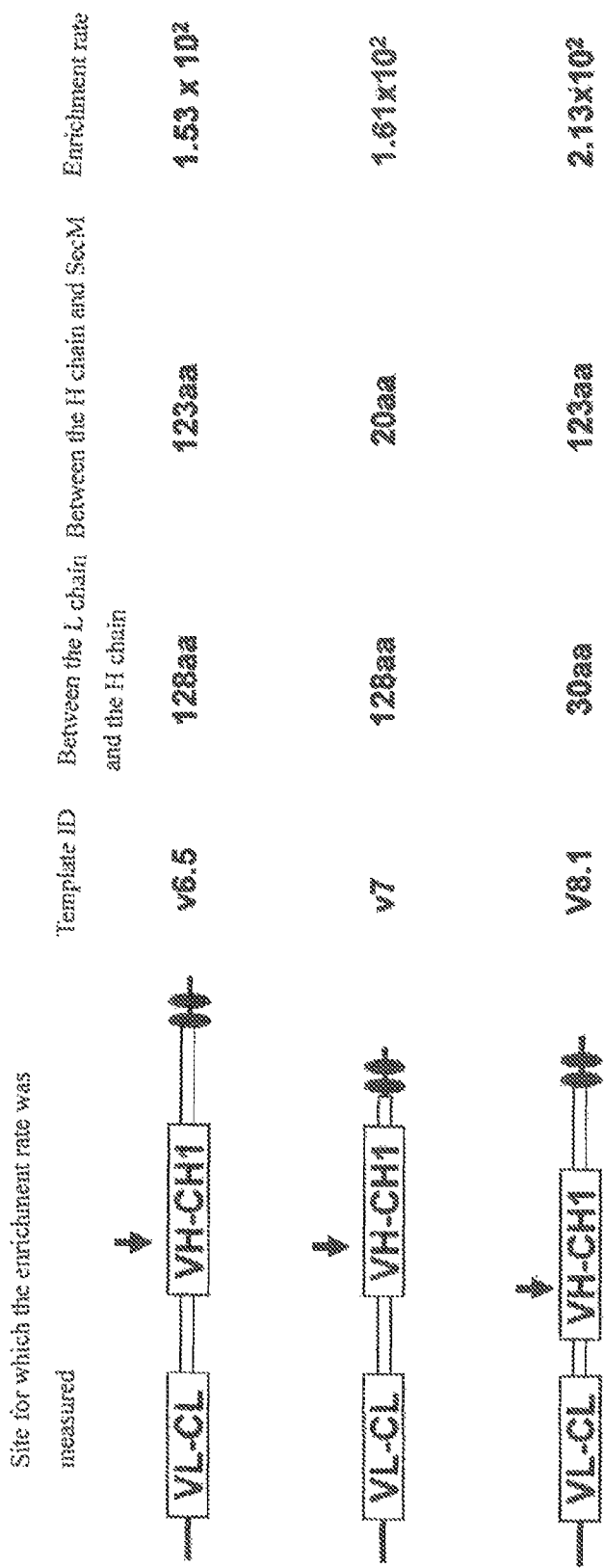

FIG. 21 is a diagram showing the relationship between the length of the linker and the enrichment ratio in monocistronic Fab-PRD.

Figure 22:
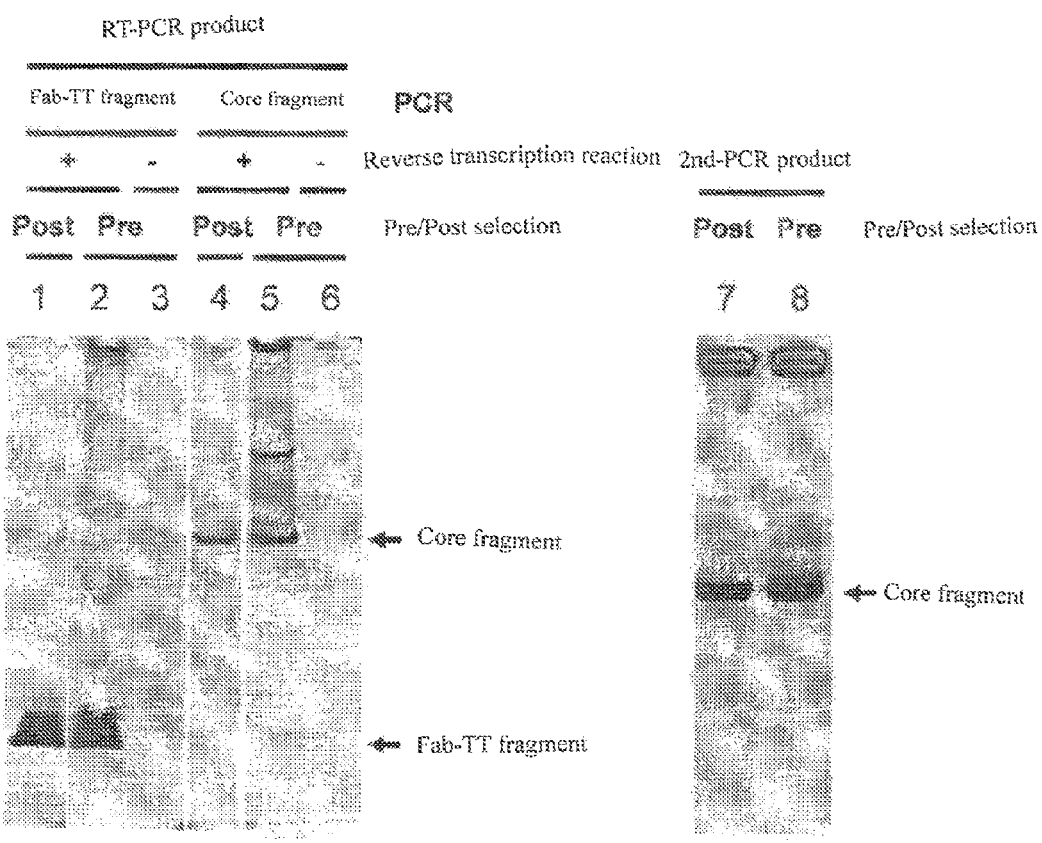

FIG. 22 is an electrophoretogram showing recovery of Fab-TT from a population of 400 molecules of Fab-TT and $1 \times 10^{12}$ molecules of Fab-HH in monocistronic Fab-PRD.

Figure 23:
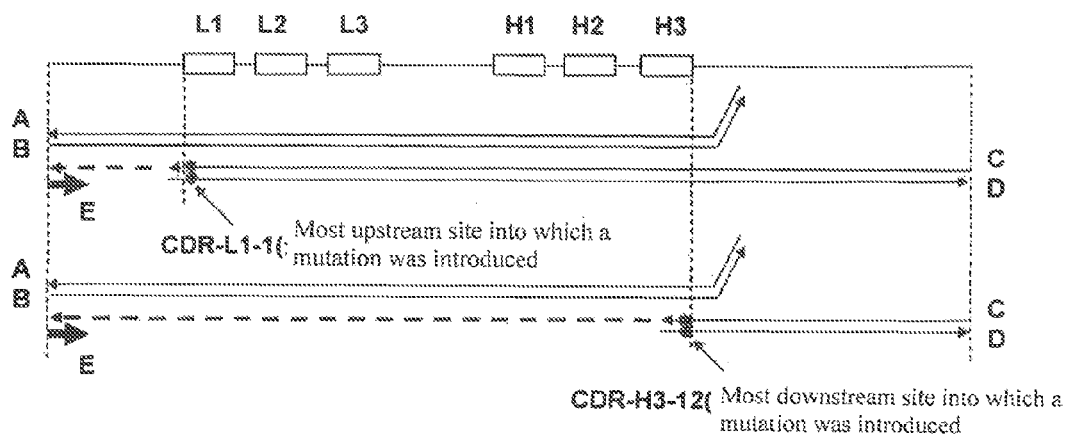

FIG. 23 is a diagram showing a summary of synthesis of a single-position/single-amino acid substitution library.

Figure 24:
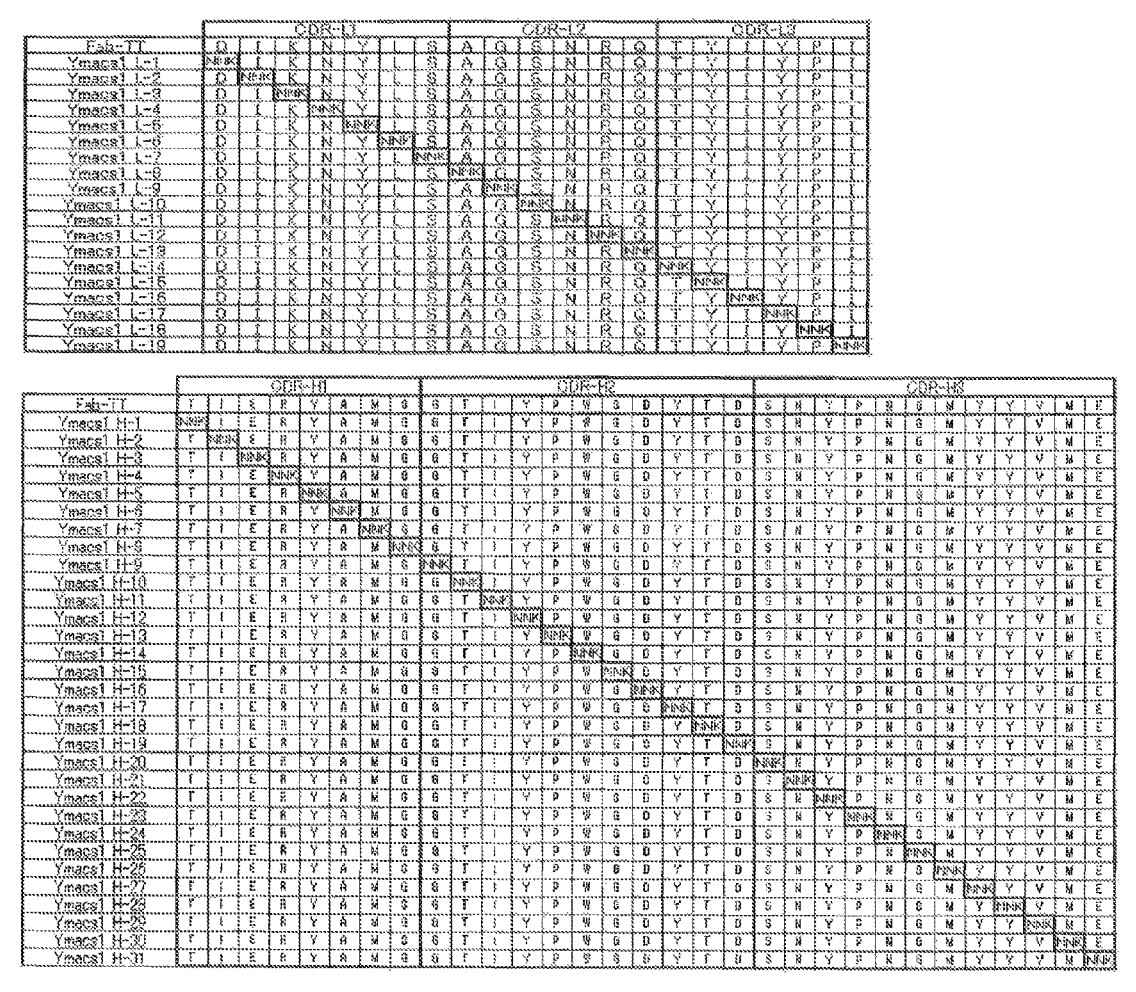

FIG. 24 is a diagram showing sequences of the CDRs in a Ymacs-primary library. NNK in the tables indicates the position into which a single amino acid substitution is to be introduced.

Figure 25:
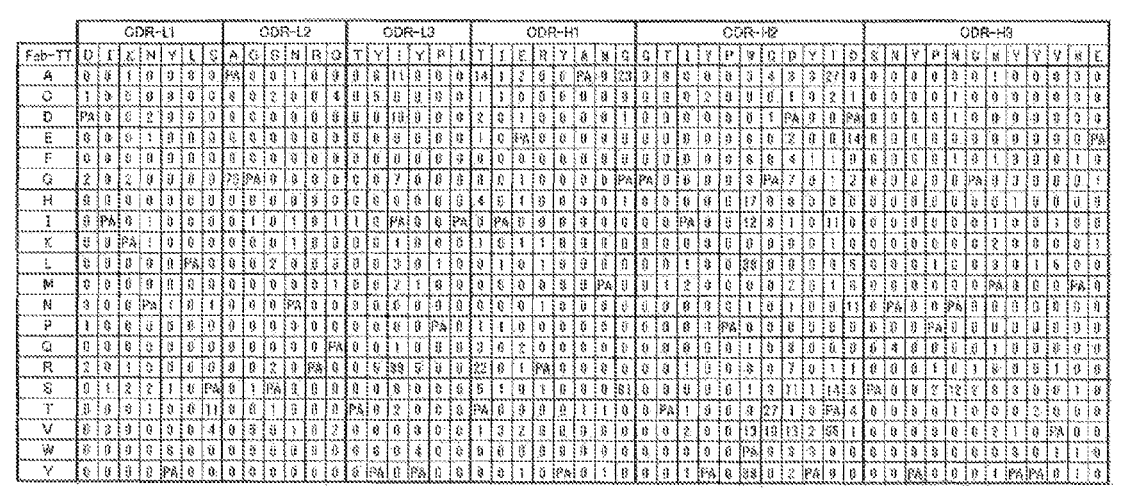

FIG. 25 is a summary of the mutations selected in the first screening. PA in the Table indicates the parent amino acid.

FIG. 26 is a diagram showing the mutations employed in the Ymacs-secondary library, and codons corresponding thereto.

FIG. 27 is a diagram showing the method for constructing the Ymacs-secondary library.

Figure 28:
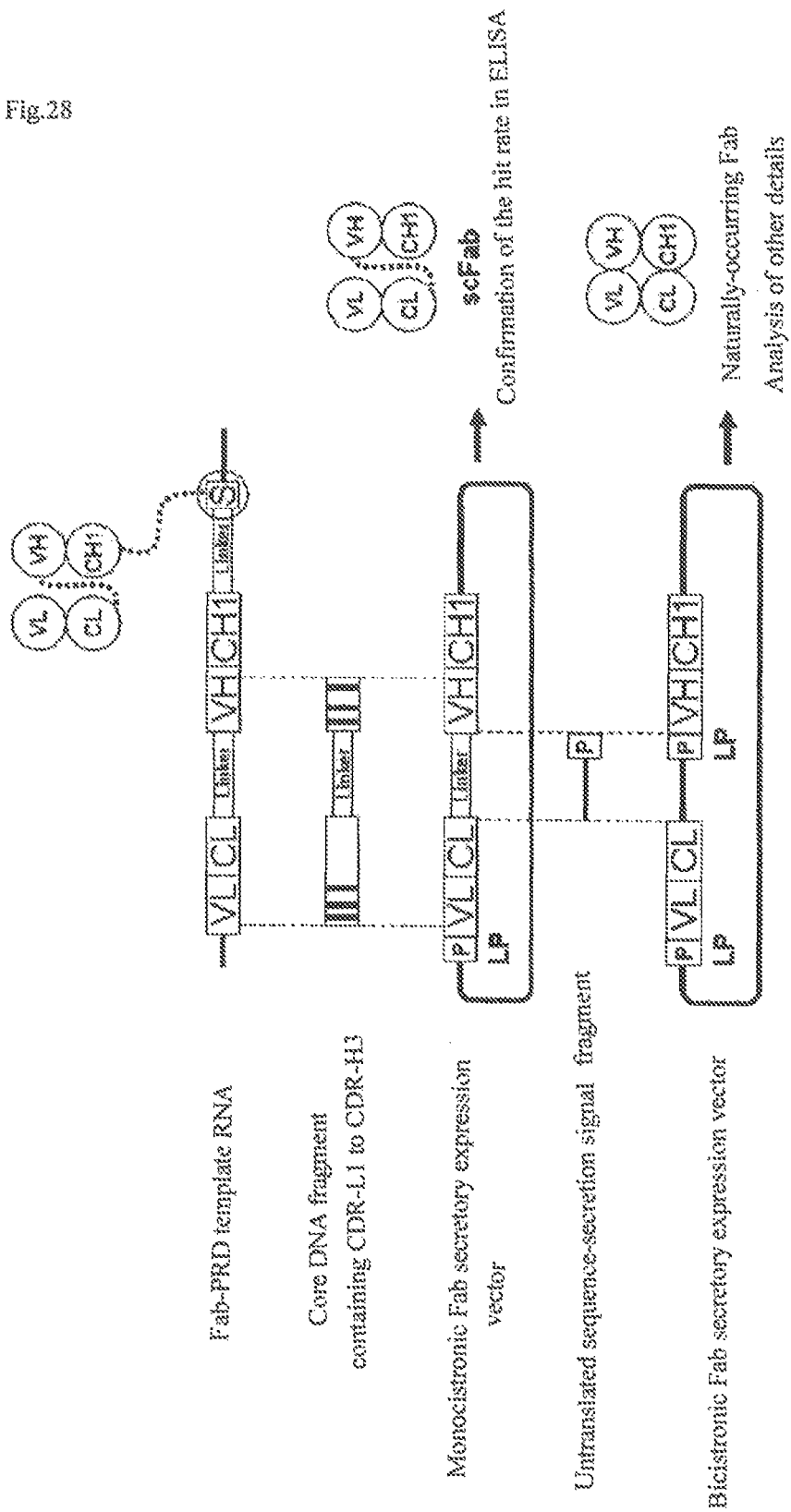

FIG. 28 is a schematic diagram showing conversion of a monocistronic secretory Fab expression vector to a bicistronic Fab secretory expression vector.

Figure 29:
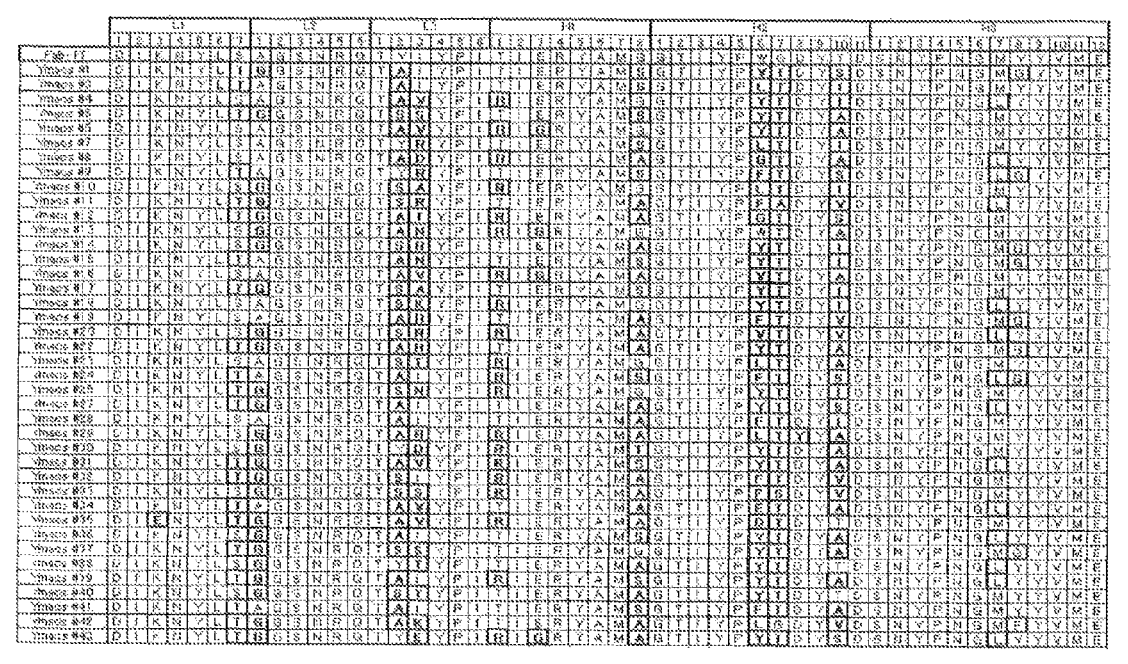

FIG. 29 is a diagram showing the sequences of the CDRs of the Fabs selected by screening of the Ymacs-secondary library.

Figure 30:
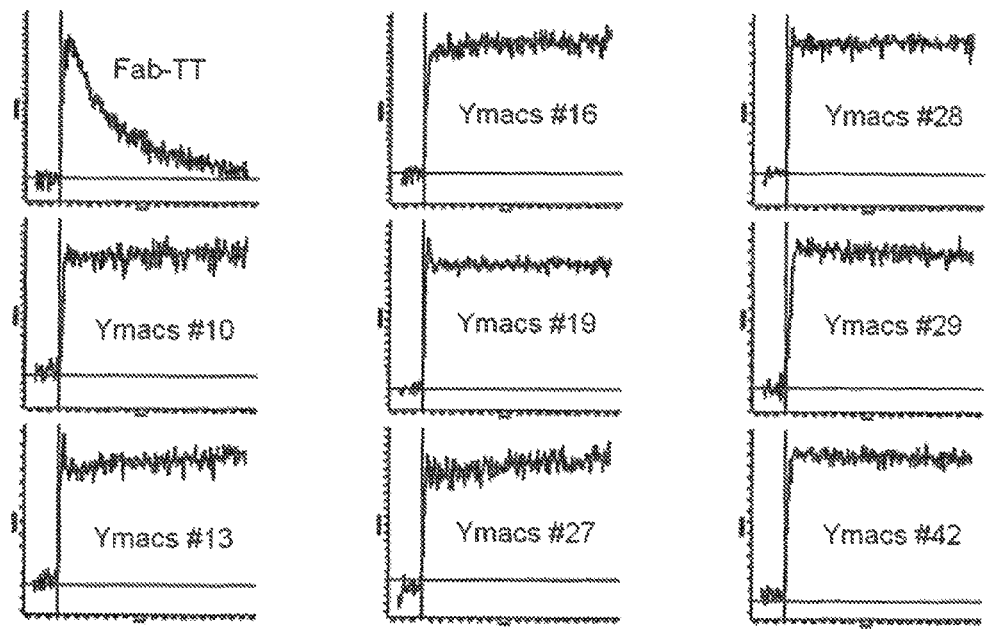

FIG. 30 is a diagram showing the result of koff measurement by SPR analysis of Fabs selected by screening of the Ymacs-secondary library.

Figure 31:
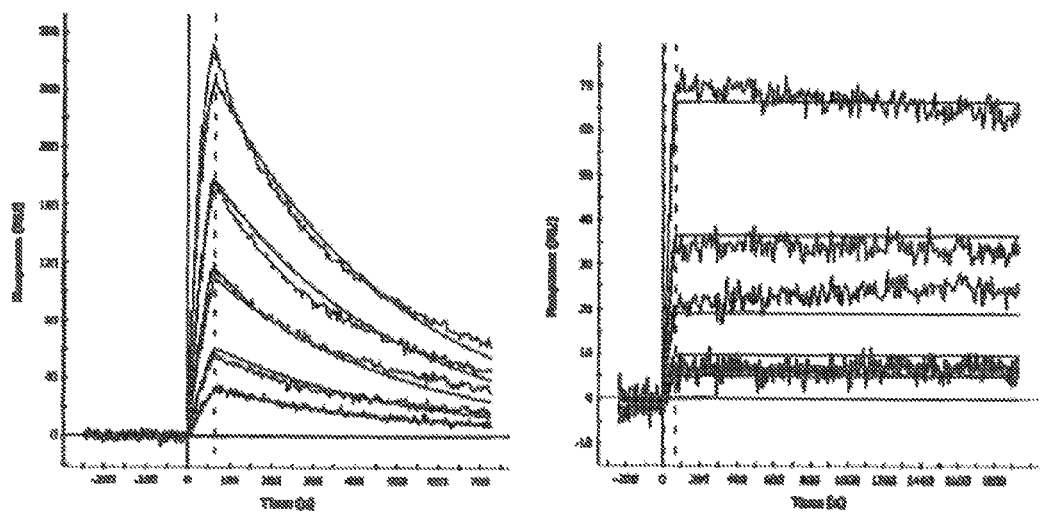

FIG. 31 is a diagram showing the result of KD measurement by SPR analysis of Fab-TT as a parent antibody and its affinity-improved mutant Ymacs #10.

FIG. 32 is a diagram showing the result of KD measurement by KinExA analysis of the affinity-improved mutants Ymacs #10 and Ymacs #19.

Figure 33:
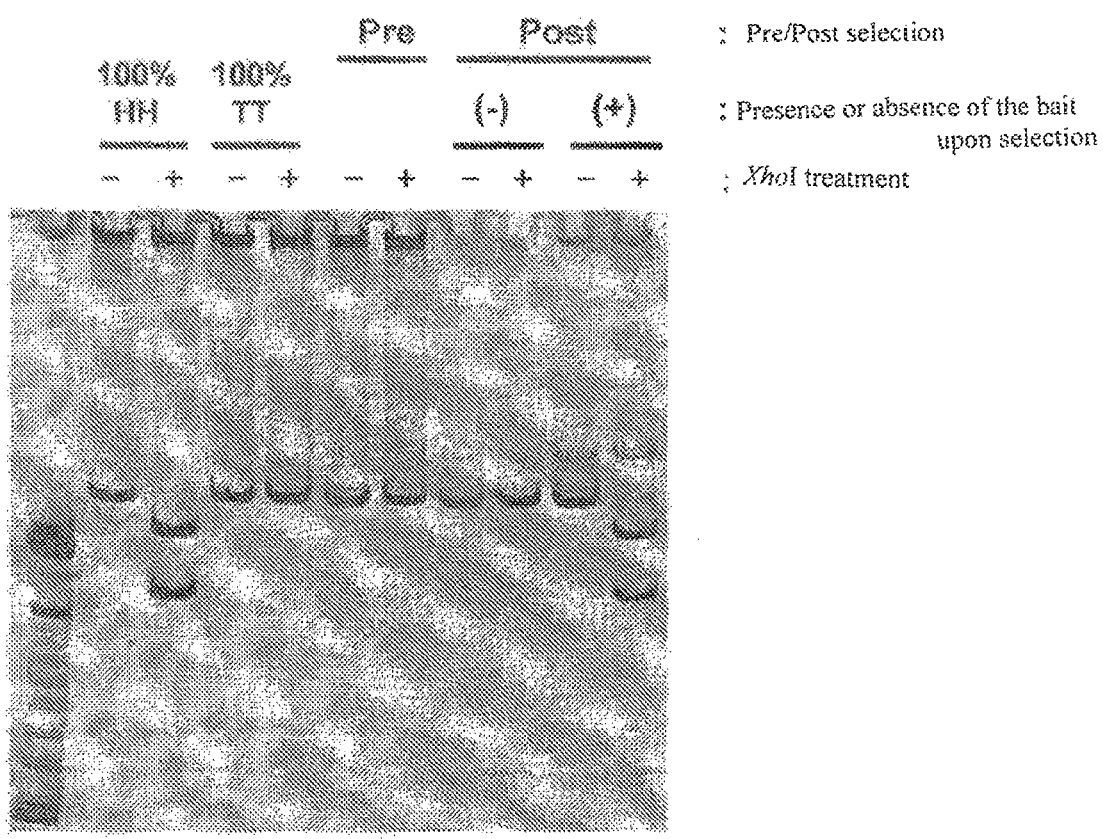

FIG. 33 is an electrophoretogram showing the result of Fab-HHxho enrichment (for full length) in CIS display.

Figure 34:
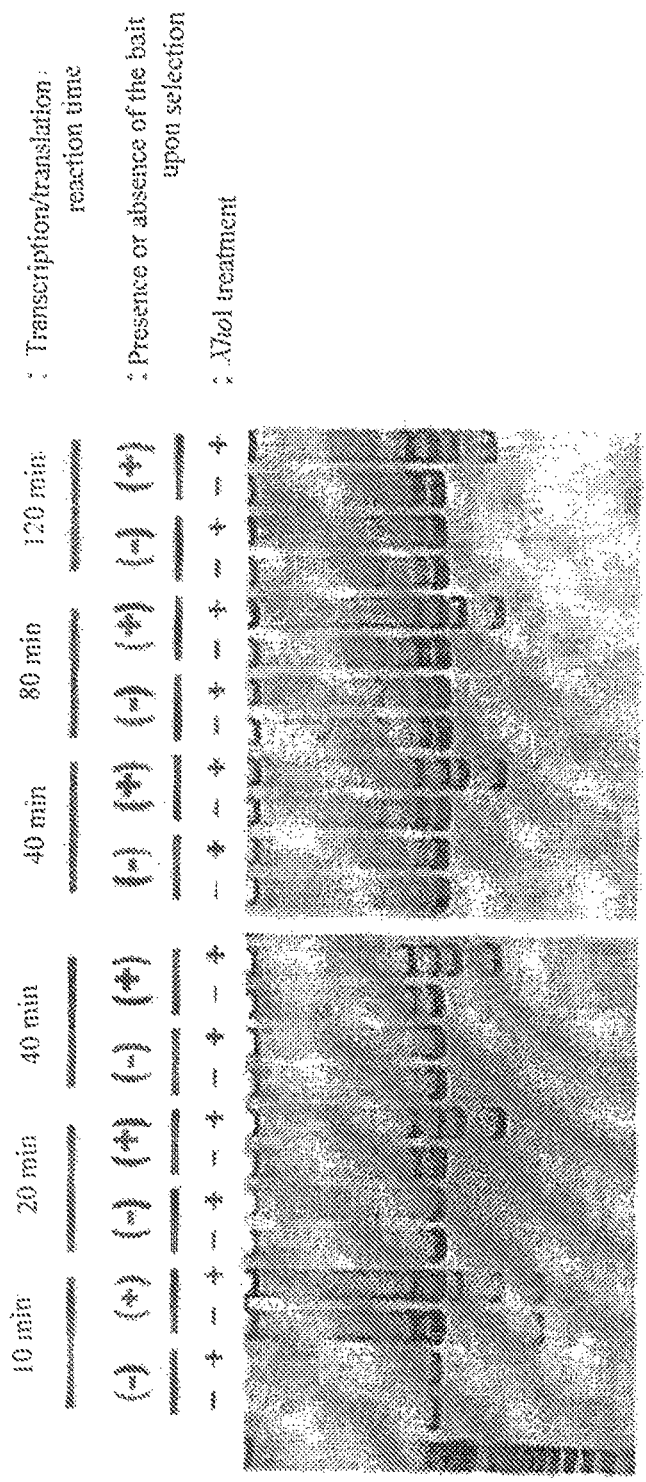

FIG. 34 is an electrophoretogram showing the result of study on the effect of the reaction time of transcription/translation in Fab-HHxho enrichment (for full length) in CIS display.

EMBODIMENTS FOR CARRYING OUT THE INVENTION

<Polynucleotide Construct>

The polynucleotide construct of the present invention comprises a Fab first chain-coding sequence and a Fab second chain-coding sequence, wherein the polynucleotide construct expresses the Fab encoded by itself without dissociation, and maintains a complex with a Fab, when it is introduced into a cell-free translation system containing ribosomes. The Fab first chain and the Fab second chain herein mean the two chains constituting Fab, and, usually, one of these is the Fab H chain and the other is the Fab L chain. However, each chain may be a chimeric chain of the H chain and the L chain. The Fab H chain means a protein containing the H-chain variable region (VH) and the H-chain constant region 1 (CH1), and the Fab L chain means a protein containing the L-chain variable region (VL) and the L-chain constant region (CL).

The term "maintains a complex with the Fab" means that the Fab is expressed in a state where the Fab is linked to the polynucleotide construct, and the complex is maintained. This is also expressed as "the Fab is displayed on the polynucleotide".

Polynucleotide Construct (Monocistronic)

The polynucleotide construct of the first embodiment of the present invention monocistronically comprises a ribosome-binding sequence, Fab first chain-coding sequence, linker peptide sequence, Fab second chain-coding sequence and scaffold-coding sequence in this order. The polynucleotide construct further comprises a structure necessary for maintaining a complex with the Fab encoded by itself, at the 3'-end of the coding region (cistron).

The ribosome-binding sequence means the sequence upstream of the initiation codon, where a ribosome is bound to initiate translation. In cases where a ribosome derived from E. coli is used as a cell-free translation system, the Shine-Dalgarno (SD) sequence is preferably used as the ribosome-binding sequence. As the SD sequence, AGGAGGT is generally known, but a modified sequence may be used as long as a ribosome can bind thereto. The ribosome-binding sequence may be appropriately selected depending on the host, and is not limited to the SD sequence.

Since sequences of the common region in Fab have been disclosed (Sakano et al., Nature (1980) vol. 286, p. 676; Ellison et al., Nucleic Acids Res. (1982) vol. 10, p. 4071; Huck et al., Nucleic Acids Res. (1986) vol. 14, p. 1779; Hieter et al., J. Biol. Chem. (1982) vol. 257, p. 1516; and Max et al., Cell (1980) vol. 22, p. 197), a Fab chain-coding sequence can be obtained by designing primers based on these sequences and amplifying the Fab H chain-coding sequence and the Fab L chain-coding sequence. Primers for cloning of the variable region and the constant region of the antibody are known (Marks et al., J. Mol. Biol. (1991) vol. 222, p. 581; Welschof et al., J. Immunol. Methods (1995) vol. 179, p. 203; Campbell et al., Mol. Immunol. (1992) vol. 29, p. 193). Alternatively, a Fab chain-coding sequence can be artificially synthesized in consideration of the codon bias and RNA processing of the host to be used in large-scale expression.

In cases where a specific Fab is to be expressed, the sequence may be amplified from a template of interest. Further, in cases where a Fab against an antigen of interest is to be screened, a library containing random Fab chain-coding sequences may be used. In cases where a Fab that binds to an antigen of interest is to be newly obtained, a naive library may be used. Further, in cases where a specific Fab which has already been obtained is to be optimized for a certain purpose, a focused library may be used In order to provide a very wide range of search space for newly obtaining a Fab that binds to an antigen of interest, various forms of naive libraries can be constructed as exemplified below. For example, it is possible to construct a natural naive library utilizing the antibody diversity produced by natural B cells, by performing reverse transcription-PCR using mRNA collected from B cells as a starting material to amplify cDNA fragments of the VH region and/or the VL region constituting Fab (Clackson et al., Nature (1991) vol. 352, p. 624-628). It is also possible to construct a semisynthetic naive library by artificially synthesizing the framework region in the VH region and/or the VL region and incorporating various naturally-occurring CDR sequences into the CDR regions (Soderlind et al., Nat. Biotechnol. (2000) vol. 18, p. 852-856). It is also possible to construct a semisynthetic naive library by incorporating a naturally-occurring sequence into the L chain (VL-CL), an artificial sequence into CDRs 1-2 in the H chain, and a naturally-occurring sequence into CDR3 in the H chain, of Fab (Hoet et al., Nat. Biotechnol. (2005) vol. 23, p. 344-348). It is also possible to construct a completely artificial naive library by artificially synthesizing the full region of the coding sequence, while giving diversity to the CDRs (Knappik et al., J. Mol. Biol. (2000) vol. 296, p. 57-86). In cases where the CDR sequences are artificially synthesized, the frequencies of amino acids that appear at each amino acid position can be controlled depending on the lengths of CDRs based on the result of analysis of naturally-occurring CDR sequences.

In cases of a focused library, various forms of the library can be constructed based on the sequence of a specific parent Fab which has already been obtained, such that the library contains, as a major component, mutants that are similar to, but different from, the parent Fab sequence. A focused library may be used for optimization for the purposes of improving the affinity, optimizing the specificity, humanizing an animal-derived antibody, eliminating a disadvantageous amino acid or sequence, improving the stability, improving the physical properties, and the like, while maintaining the antigen-binding property of the parent Fab.

For example, error-prone PCR may be used for randomly and sporadically introducing one or several single amino acid substitutions over the entire VH region and/or VL region (Boder et al., Proc Natl Acad Sci USA (2000) vol. 97, p. 10701-10705). Error-prone PCR utilizes the phenomenon that errors can be made to easily occur by controlling the concentrations of the 4 types of deoxynucleotides as substrates and the type and concentration of the divalent cation added. It is also possible to use artificially-designed mutation-introducing primers for targeting a specific amino acid (s) constituting Fab to introduce one or several single amino acid substitutions in consideration of the amino acid composition (Rajpal et al., Proc Natl Acad Sci USA (2005) vol. 102, p. 8466-8471). Further, it is also possible to use artificially-designed mutation-introducing primers for randomizing the sequence(s) of about 1 to 3 CDR(s) while the sequences of about 3 to 5 CDRs are maintained among the total of 6 CDRs, such that the randomization occurs not for single amino acids but for entire CDR sequences (Lee et al., Blood (2006) vol. 108, p. 3103-3111). Further, it is also possible to fix one of the L chain and the H chain while the other is randomized utilizing various naturally-occurring sequences (Kang et al., Proc Natl Acad Sci USA (1991) vol. 88, p. 11120-11123).

As the polynucleotide construct of the present invention, a library wherein one or more amino acids in the complementarity determining regions (CDRs) of the Fab first chain and/or the Fab second chain contain a single amino acid substitution(s) is preferred. Such a library can be prepared by, for example, PCR using primers designed such that the single amino acid substitution(s) is/are introduced.

By performing screening using such a polynucleotide construct library, an antibody against an antigen of interest can be obtained.

The sequence encoding the linker peptide that links the Fab first chain-coding sequence and the Fab second chain-coding sequence is preferably a sequence encoding a water-soluble polypeptide composed of 15 to 120 amino acid residues, more preferably a sequence encoding a water-soluble polypeptide composed of 20 to 30 amino acids in view of the screening efficiency of the library. Examples of the sequence include an amino acid sequence into which Arg was introduced for increasing the water solubility, and the sequence may also be one encoding the so-called GS linker, which mainly contains glycine and seine.

The sequence encoding the linker peptide may be placed between protease recognition sequences. By this, after translation of the polynucleotide construct into an amino acid sequence, the linker peptide is cleaved by protease, resulting in the display of a natural Fab. Examples of the protease recognition sequence include the enterokinase recognition sequence DDDDK (SEQ ID NO:31) and the factor Xa recognition sequence IEGR (SEQ ID NO:32).

Examples of the scaffold-coding sequence linked to the 3'-side of the Fab chain-coding sequence include those encoding an amino acid sequence having a length sufficient as a scaffold with which the first chain and the second chain of Fab can be translated and accurately folded on a ribosome, DNA and/or mRNA to form a complex and react with an antigen. The scaffold-coding sequence is a sequence preferably encoding at least 15 amino acids, more preferably encoding 15 to 120 amino acids. The scaffold sequence encoded preferably has high water solubility and does not form a special spatial structure. Specific examples of such a sequence which may be used include the so-called GS linker, which mainly contains glycine and serine, and partial sequences of gene III in phages As the structure necessary for maintaining a complex with the Fab chain encoded by itself, the construct may, for example, have a ribosome stall sequence at the 3'-end of the cistron (in cases of ribosome display); have a DNA-binding protein-coding sequence and a binding sequence for the DNA-binding protein (in cases of CIS display); or have puromycin or a derivative thereof added to the 3'-end (in cases of mRNA display). By this, the expressed Fab chain forms a complex with the polynucleotide, and hence the nucleotide sequences of the first and Fab second chain-coding sequences are physically associated with the amino acid sequences encoded thereby.

Polynucleotide Construct (Monocistronic) to be Subjected to Ribosome Display

Examples of the ribosome stall sequence include the sequence encoding SecM of E. coli. The SecM sequence is also called the SecM stall sequence, and is reported to cause translation arrest inside the ribosome GIRAGP, SEQ ID NO:30). Since, by introduction of this sequence, the complex of mRNA, ribosome and fusion protein can be efficiently maintained (Nakatogawa et al., Mol. Cell (2006) vol. 22, p. 545-552), the Fab chain can be associated with the nucleotide sequence encoding it. Two or more SecM sequences may be linked, and the number of SecM sequences to be linked is preferably 2 to 4, more preferably 2.

Further, a polyproline sequence such as diproline may be used as the ribosome stall sequence, and such a sequence may be used either alone or in combination with a SecM sequence(s).

In the 3'-side of the ribosome stall sequence, a stop codon is preferably placed in the same reading frame.

It is also possible to simply delete the stop codon instead of employing a ribosome stall sequence, for performing ribosome display.

The Fab first chain-coding sequence, linker-coding sequence, Fab second chain-coding sequence, scaffold-coding sequence and ribosome stall sequence are linked together in the same reading frame. The term "linked together in the same reading frame" herein means that these components are linked together such that they are translated as a fusion protein. The Fab first chain-coding sequence, linker-coding sequence, Fab second chain-coding sequence, scaffold-coding sequence and ribosome stall sequence may be linked together either directly, or via a tag sequence(s) and/or an arbitrary polypeptide sequences) placed between, before and/or after the components.

An example of the polynucleotide construct of the first embodiment of the present invention wherein ribosome display is utilized is shown in FIG. 1.

SEQ ID NO:19 shows the nucleotide sequence of a polynucleotide construct containing: a promoter sequence (nucleotide positions 9 to 31); a ribosome-binding sequence (SD sequence, nucleotide positions 81 to 87); and an anti-Her2 Fab L+H chain-expressing cistron (nucleotide positions 94 to 2220, see SEQ ID NO:20 for its amino acid sequence) containing an anti-Her2 Fab L chain-coding sequence, FLAG tag, linker sequence (GS linker), FLAG tag, anti-Her2 Fab H chain-coding sequence, His tag, scaffold sequence (GS linker) and ribosome stall sequence (secM+diproline).

SEQ ID NO:21 shows the nucleotide sequence of a polynucleotide construct containing: a promoter sequence (nucleotide positions 9 to 31); a ribosome-binding sequence (SD sequence, nucleotide positions 81 to 87); and an anti-TNFαR Fab L+H chain-expressing cistron (nucleotide positions 94 to 2226, see SEQ ID NO:22 for its amino acid sequence) containing an anti-TNFαR Fab L chain-coding sequence, FLAG tag, linker sequence (GS linker), FLAG tag, anti-TNFαR Fab H chain-coding sequence, His tag, scaffold sequence (GS linker) and ribosome stall sequence (secM+diproline).

However, needless to say, the polynucleotide construct of the present invention is not limited to these.

Polynucleotide Construct (Monocistronic) to be Subjected to mRNA Display

The amino acid sequence may be physically associated with the nucleotide sequence encoding it by utilizing, instead of the ribosome stall sequence, puromycin or a derivative thereof to allow formation of a complex between the Fab and the polynucleotide (mRNA display). That is, puromycin or a derivative thereof is linked to the 3'-end of the polynucleotide construct via a spacer, and the C-terminus of the translation product is covalently bound to the puromycin or a derivative thereof to allow formation of a complex between Fab and the polynucleotide. By this, association of the amino acid sequence of the Fab chain with the nucleotide sequence encoding it is possible.

As the puromycin or a derivative thereof, puromycin; and puromycin derivatives such as ribocytidyl puromycin, deoxycytidyl puromycin and deoxyuridyl puromycin; are especially preferred.

Examples of the spacer to be used for linking the puromycin or a derivative thereof to the 3'-end of the polynucleotide construct include macromolecular substances such as polyethylene and polyethylene glycol, and derivatives thereof and biomacromolecular substances such as oligonucleotides and peptides, and derivatives thereof as described in WO98/16636. Among these, polyethylene glycol is preferred.

In another embodiment of mRNA display, the amino acid sequence may be physically associated with the nucleotide sequence encoding it by linking a streptavidin-coding sequence to the 3'-end side of the polynucleotide construct and further linking biotin to the 3'-end, to allow binding of the streptavidin portion of the translated protein to the biotin, resulting in formation of a complex between Fab and the polynucleotide.

An example of the polynucleotide construct of the first embodiment of the present invention wherein mRNA display is utilized is shown in FIG. 2.

Polynucleotide Construct (Monocistronic) to be Subjected to CIS Display

Further, the amino acid sequence may be physically associated with the nucleotide sequence encoding it by utilizing a DNA-binding protein-coding sequence and the binding sequence for the DNA-binding protein instead of the ribosome stall sequence, to allow formation of a complex between Fab and the polynucleotide (CIS display, WO2004/22746). More specifically, a DNA-binding protein-coding sequence and the binding sequence for the DNA-binding protein are linked downstream of the scaffold sequence of the polynucleotide construct, and, Fab, the scaffold sequence and the DNA-binding protein are expressed as a fusion protein. Since the DNA-binding protein binds to the binding sequence for the DNA-binding protein downstream of the 3'-side cistron, a complex between Fab and the polynucleotide is formed, and hence the amino acid sequence of the Fab chain can be associated with the nucleotide sequence encoding it. Examples of the DNA-binding protein herein include the RepA protein, which has a cis-type binding mode wherein a DNA-binding protein is bound to the binding sequence for the DNA-binding protein displayed on the same DNA molecule without dissociation, during the transcription/translation reaction, from the DNA molecule used as the template for the transcription/translation. Examples of the RepA-binding sequence include the CIS sequence and the following on sequence (Proc. Natl. Acad. Sci. U.S.A., vol. 101, p. 2806-2810, 2004; and Japanese Translated PCT Patent Application Laid-open No. 2005-537795). Other examples of the DNA-binding protein having a cis-type binding mode include the RecC protein encoded by E. coli Ti plasmid (Pinto, et al., Mol. Microbiol. (2011) vol. 81, p. 1593-1606), A protein of φX174 phage (Francke, et al., Proc Natl Acad Sci USA (1972) vol. 69, p. 475-479) and Q protein of phage (Echols, et al., Genetics (1976) vol. 83, p. 5-10), each of which may be used in combination with its binding sequence. In cases where a cell-free translation system wherein transcription is well-coupled with translation is employed, the synthesized protein is released in the vicinity of the transcription termination site, so that a DNA protein generally considered to have a trans-type binding mode, such as a DNA-binding domain of a nuclear receptor including the estrogen receptor, or a DNA-binding domain of LexA or Gal4 used for the two-hybrid system, may be used in combination with its binding sequence.

An example of the polynucleotide construct of the first embodiment of the present invention wherein CIS display is utilized is shown in FIG. 3.

SEQ ID NO:70 shows the nucleotide sequence of a polynucleotide construct containing: a promoter sequence (nucleotide positions 612 to 639); a ribosome-binding sequence (SD sequence, nucleotide positions 672 to 675); an anti-Her2 Fab L+H chain-expressing cistron (nucleotide positions 689 to 3322, see SEQ ID NO:71 for its amino acid sequence) containing an anti-Her2 Fab L chain-coding sequence, FLAG tag, linker sequence (GS linker), FLAG tag, anti-Her2 Fab H chain-coding sequence, His tag, scaffold sequence (GS linker) and RepA-coding sequence; and CIS-ori (nucleotide positions 3326 to 4100).

SEQ ID NO:72 shows the nucleotide sequence of a polynucleotide construct containing: a promoter sequence (nucleotide positions 612 to 639); a ribosome-binding sequence (SD sequence, nucleotide positions 672 to 675); an anti-TNFαR Fab L+H chain-expressing cistron (nucleotide positions 689 to 3328, see SEQ ID NO:73 for its amino acid sequence) containing an anti-TNFαR Fab L chain-coding sequence, FLAG tag, linker sequence (GS linker), FLAG tag, anti-TNFαR H chain-coding sequence, His tag, scaffold sequence (GS linker) and RepA-coding sequence; and CIS-ori (nucleotide positions 3332 to 4106).

However, needless to say, the polynucleotide construct of the present invention is not limited to these.

Polynucleotide Construct (Bicistronic)

The polynucleotide construct of the second embodiment of the present invention comprises a Fab first chain-expressing cistron and a Fab second chain-expressing cistron each containing a ribosome-binding sequence, a Fab first chain-coding sequence or Fab second chain-coding sequence, and a scaffold-coding sequence in this order. The Fab first chain-expressing cistron (Fab chain-expressing cistron in the 5'-side) further comprises at its 3'-end a ribosome stall sequence, and the Fab second chain-expressing cistron (Fab chain-expressing cistron in the 3'-side) further comprises at its 3'-end side a structure necessary for maintaining a complex with the Fab encoded by itself. Examples of the structure necessary for maintaining a complex with the Fab encoded by itself herein include a ribosome stall sequence; a DNA-binding protein-coding sequence and a binding sequence for the DNA-binding protein; and puromycin or a derivative thereof; as described above.

That is, the Fab first chain-expressing cistron comprises a Fab first chain-coding sequence and a scaffold-coding sequence in the 3'-side of a ribosome-binding sequence in this order, and the Fab second chain-expressing cistron comprises a Fab second chain-coding sequence and a scaffold-coding sequence in the 3'-side of a ribosome-binding sequence in this order. The Fab first chain and the Fab second chain may be either the H chain and the L chain, respectively, or the L chain and the H chain, respectively, or each of the chains may be a chimeric chain between the H chain and the L chain.

The length between the Fab first chain-expressing cistron and the Fab second chain-expressing cistron is not restricted as long as an interval can be secured when translation has once terminated in the Fab first chain-expressing cistron and the ribosome is stalled, so that the ribosome can bind to the ribosome-binding sequence in the Fab second chain-expressing cistron. The length is preferably 50 to 200 bp.

The ribosome-binding sequence and the Fab chain-coding sequence may be those described above.

Examples of the scaffold-coding sequence linked to the 3'-side of each Fab chain-coding sequence include those encoding an amino acid sequence having a length sufficient as a scaffold with which the H chain or the L chain of Fab can be translated and precisely folded to form a complex on a ribosome, DNA and/or mRNA, and react with an antigen. The scaffold-coding sequence is a sequence preferably encoding at least 15 amino acids, more preferably encoding 15 to 120 amino acids. The scaffold sequence encoded preferably has high water solubility and does not form a special spatial structure. Specific examples of such a sequence which may be used include the so-called GS linker, which mainly contains glycine and serine, and partial sequences of gene III in phages Polynucleotide Construct (Bicistronic) to be Subjected to Ribosome Display In the polynucleotide construct of the second embodiment of the present invention, in order to allow formation of a complex between mRNA and a polypeptide (the first chain or the second chain of Fab) on a ribosome, a ribosome stall sequence as described above is placed at the 3'-end of the Fab first chain-expressing cistron. A stop codon is preferably placed in the 3'-side of the ribosome stall sequence in the same reading frame. It is also possible to simply delete the stop codon instead of employing a ribosome stall sequence, for performing ribosome display.

The Fab first chain-coding sequence or Fab second chain-coding sequence, scaffold-coding sequence and ribosome stall sequence are linked together in the same reading frame. The term "linked together in the same reading frame" herein means that these components are linked together such that they are translated as a fusion protein. The Fab first chain-coding sequence or Fab second chain-coding sequence, scaffold-coding sequence and ribosome stall sequence may be linked together either directly, or via a tag sequences) and/or an arbitrary polypeptide sequence(s) placed between, before and/or after the components.

An example of the polynucleotide construct of the second embodiment of the present invention wherein ribosome display is utilized for both the Fab first chain-expressing cistron and the Fab second chain-expressing cistron is shown in FIG. 4.

SEQ ID NO:13 shows the nucleotide sequence of a polynucleotide construct containing: a promoter sequence (nucleotide positions 9 to 31); a ribosome-binding sequence (SD sequence, nucleotide positions 81 to 87); an anti-Her2 Fab L chain-expressing cistron (nucleotide positions 94 to 1158, see SEQ ID NO:14 for its amino acid sequence) containing an anti-Her2 Fab L chain-coding sequence, FLAG tag, scaffold sequence (GS linker) and ribosome stall sequence (secM+diproline); a ribosome-binding sequence (SD sequence, base positions 1191 to 1197); and an anti-Her2 Fab H chain-expressing cistron (nucleotide positions 1264 to 2364, see SEQ ID NO:15 for its amino acid sequence) containing an anti-Her2 Fab H chain-coding sequence, His tag, scaffold sequence (GS linker) and ribosome stall sequence (secM+diproline).

SEQ ID NO 16 shows the nucleotide sequence of a polynucleotide construct containing: a promoter sequence (nucleotide positions 9 to 31); a ribosome-binding sequence (SD sequence, nucleotide positions 81 to 87); an anti-TNFα receptor (TNFαR) Fab L chain-expressing cistron (nucleotide positions 94 to 1158, see SEQ ID NO:17 for its amino acid sequence) containing an anti-TNFαR Fab L chain-coding sequence, FLAG tag, scaffold sequence (GS linker) and ribosome stall sequence (secM+diproline); a ribosome-binding sequence (SD sequence, base positions 1191 to 1197); and an anti-TNFαR Fab H chain-expressing cistron (nucleotide positions 1264 to 2370, see SEQ ID NO:18 for its amino acid sequence) containing an anti-TNFαR Fab H chain-coding sequence, His tag, scaffold sequence (GS linker) and ribosome stall sequence (secM+diproline).

However, needless to say, the polynucleotide construct of the present invention is not limited to these.

Polynucleotide Construct (Bicistronic) to be Subjected to mRNA Display

In terms of the Fab second chain-expressing cistron (the Fab chain-expressing cistron in the 3'-side), puromycin or a derivative thereof may be utilized to allow formation of a complex between the Fab chain and the polynucleotide in order to physically associate the amino acid sequence with the nucleotide sequence encoding it (mRNA display). That is, puromycin or a derivative thereof is linked to the end of the 3'-side cistron, that is, to the 3'-end of the polynucleotide construct, via a spacer, and, when the 3'-side cistron is translated, the C-terminus of the translation product is covalently bound to the puromycin or a derivative thereof to allow formation of a complex between the Fab chain and the polynucleotide. By this, association of the amino acid sequence of the Fab chain with the nucleotide sequence encoding it is possible.

An example of the polynucleotide construct of the second embodiment of the present invention wherein ribosome display is utilized for the Fab first chain-expressing cistron and mRNA display is utilized for the Fab second chain-expressing cistron is shown in FIG. 5.

Polynucleotide Construct (Bicistronic) to be Subjected to CIS Display

In terms of the Fab second chain-expressing cistron (the Fab chain-expressing cistron in the 3'-side), a DNA-binding protein-coding sequence and the binding sequence for the DNA-binding protein may be utilized to allow formation of a complex between the Fab chain and the polynucleotide in order to physically associate the amino acid sequence with the nucleotide sequence encoding it (CIS display, WO2004/22746). More specifically, a DNA-binding protein-coding sequence and the binding sequence for the DNA-binding protein are linked to the 3'-end-side of the Fab second chain-expressing cistron, that is, downstream of the Fab second chain-coding sequence and the scaffold sequence of the Fab second chain-expressing cistron, and the Fab second chain-expressing cistron is expressed as a fusion protein of the Fab second chain, scaffold sequence and DNA-binding protein. The DNA-binding protein is bound to the binding sequence for the DNA-binding protein located downstream of the Fab second chain-expressing cistron to allow formation of a complex between the Fab second chain and the polynucleotide. By this, association of the amino acid sequence of the Fab second chain with the nucleotide sequence encoding it is possible. Examples of the DNA-binding protein herein include the RepA protein, which has the so-called cis-type binding mode wherein a DNA-binding protein is bound to the binding sequence for the DNA-binding protein present on the same DNA molecule without dissociation, during the transcription/translation reaction, from the DNA molecule used as the template for the transcription/translation. Examples of the RepA-binding sequence include the CIS sequence and the following on sequence (Proc. Natl. Acad. Sci. U.S.A., vol. 101, p. 2806-2810, 2004; and Japanese Translated PCT Patent Application Laid-open No. 2005-537795). Other examples of the DNA-binding protein having a cis-type binding mode include the RecC protein encoded by *E. coli* Ti plasmid (Pinto, et al., Mol. Microbiol. (2011) vol. 81, p. 1593-1606), A protein of φX174 phage (Francke, et al., Proc Natl Acad Sci USA (1972) vol. 69, p. 475-479) and Q protein of λ phage (Echols, et al., Genetics (1976) vol. 83, p. 5-10), each of which may be used in combination with its binding sequence. In cases where a cell-free translation system wherein transcription is well-coupled with translation is employed, the synthesized protein is released in the vicinity of the transcription termination site, so that a DNA protein generally considered to have a trans-type binding mode, such as a DNA-binding domain of a nuclear receptor including the estrogen receptor, or a DNA-binding domain of LexA or Gal4 used for the two-hybrid system, may be used in combination with its binding sequence.

An example of the polynucleotide construct of the second embodiment of the present invention wherein ribosome display is utilized for the Fab first chain-expressing cistron and CIS display is utilized for the Fab second chain-expressing cistron is shown in FIG. 6.

The polynucleotide construct of the present invention may be either mRNA, or DNA from which mRNA is transcribed. In cases where the polynucleotide construct is mRNA, the term "expresses Fab" means translation of mRNA into the Fab protein, and, in cases where the polynucleotide construct is DNA, the term "expresses Fab" means transcription of DNA into mRNA and translation of the mRNA into the Fab protein. In cases where the polynucleotide construct is DNA, a promoter sequence recognized by RNA polymerase for transcription into mRNA is preferably additionally contained. The promoter may be appropriately selected depending on the expression system to be used. For example, in cases where an *E. coli* cell or a cell-free translation system derived from *E. coli* is employed, examples of the promoter include promoters that function in *E. coli*, such as T7 promoter, T3 promoter, SP6 promoter, and endogenous promoters in the *E. coli* genome.

The polynucleotide construct may be incorporated into a plasmid vector, phage vector, virus vector or the like. The type of the vector may be appropriately selected depending on the translation system and the screening system used. The polynucleotide constructs described above and vectors containing them may be prepared by known genetic engineering methods described in Molecular Cloning (Cold spring Harbor Laboratory Press, Cold spring Harbor (USA), 2001) and the like.

In the first embodiment and the second embodiment described above, either the Fab H chain-coding sequence or the Fab L chain-coding sequence may be placed upstream of the other. In cases where the Fab H chain-coding sequence is placed upstream (in the 5'-side) and the H chain is first translated and kept in the vicinity, followed by its pairing with the L chain immediately after completion of translation of the L chain, the risk of pairing between L chains, which is said to occur more easily than pairing between H chains, can be reduced, which is advantageous. On the other hand, in cases where the Fab L chain-coding sequence is placed upstream (in the 5'-side) and the L chain is first translated and kept in the vicinity, followed by its pairing with the H chain immediately after completion of translation of the H chain, the risk of occurrence of aggregation of H chains, which are said to generally have higher risk of aggregation because of worse physical properties than L chains, can be reduced.

<Method for Producing Fab>

The method of the present invention for producing Fab comprises the step of introducing the polynucleotide construct described above into a cell-free translation system containing ribosomes, to produce Fab. Examples of the cell-free translation system include cell-free translation systems obtained from cells of *E. coli*, yeasts, mammalian cells and the like, and the cell-free translation system is preferably derived from *E. coli*.

The cell-free translation system may be either a cell extract obtained by extracting a fraction containing ribosomes from cells, or a reconstruction-type cell-free translation system constructed from factors purified individually.

A cell extract-type cell-free translation system is generally prepared by homogenizing cells and removing unwanted substances by ultracentrifugation at about 30,000 g to obtain a cell extract called S30, which is then subjected to an appropriate treatment. As a starting material for S30, cells of various organisms have been tested so far, and 3 types of materials, *E. coli* (Zubay, Annual Review of Genetics (1973) vol. 7, p. 267-287), wheat germ (Roberts, et al., Proc Natl Acad Sci USA (1973) vol. 70, p. 2330-2334) and rabbit reticulocytes (Pelham, et al., Eur. J. Biochem. (1976) vol. 67, p. 247-256) are commonly used at present. In cases where *E. coli* is used as a starting material, various mutant strains may be used depending on the purpose, for preparing S30. For example, when one wants to stabilize linear double-stranded DNA to be used as a template in the reaction liquid, the SL119 strain (Lesley, et al., J. Biol. Chem. (1991) vol. 266, p. 2632-2638), which is a mutant strain deficient in RecD, a subunit of the RecBCD complex (Exonuclease V), may be used.

Examples of the reconstruction-type cell-free translation system constituted by factors purified individually include the PURE system described in JP 2003-102495 A and JP 2008-271903 A. Since this reconstruction-type cell-free translation system can prevent contamination of nuclease and protease more easily than a cell-free translation system using a cell extract, the efficiency of translation of mRNA into the polypeptide can be increased.

In cases of the CIS display, double-stranded DNA, which is relatively stable in a cell extract, is used as a gene medium, so that a cell extract obtained by extracting a fraction containing ribosomes from cells can also be used.

In cases of the ribosome display, there is the risk of degradation of RNA as a gene medium by ribonuclease contained in a large amount in the cell extract, so that a reconstruction-type cell-free translation system constituted by factors purified individually is preferred. Such ribosome display using the PURE system is called "PURE ribosome display (PRD)".

The factors can be obtained by purification from extracts of various cells. Examples of the cells from which the factors are purified include prokaryotic cells and eukaryotic cells. Examples of the prokaryotic cells include *E. coli* cells, extreme thermophile cells and *Bacillus subtilis* cells. Examples of the eukaryotic cells include yeast cells, plant cells, insect cells and mammalian cells.

It is more preferred to individually purify ribosomes and other factors to prepare the reconstruction-type cell-free translation system.

A ribosome is a huge complex constituted by ribosomal RNA and various ribosomal proteins, and composed of 2 subunits, that is, the large subunit and the small subunit. The ribosome and the subunits constituting it can be separated from each other by sucrose density gradient or the like, and their sizes are represented by the sedimentation coefficient. More specifically, in prokaryotes, the ribosome and the subunits constituting it have the following sizes. Since prokaryotes such as E. coli can be easily prepared by large-scale culture, a prokaryote such as E. coli is preferred as the organism from which ribosomes are to be prepared in a large amount.

| | Ribosome (70S) = | large subunit (50S) + | small subunit (30S) |
|---|---|---|---|
| Molecular weight: | about $2.5 \times 10^6$ | about $1.6 \times 10^6$ | about $0.9 \times 10^6$ |

Still more specifically, it is known that each of the 50S subunit and the 30S subunit is constituted by the following components.

50S subunit:
34 types of proteins L1 to L34 (ribosomal proteins)
23S RNA (about 3200 nucleotides)
5S RNA (about 120 nucleotides)
30S subunit:
21 types of proteins S1 to S21 (ribosomal proteins)
16S RNA (about 1540 nucleotides)

That is, each subunit can be isolated as a complex composed of these components. Further, a ribosome can be isolated as a complex of the subunits. A purified ribosome means, for example, in cases of a ribosome derived from a prokaryote, the complex purified as a 70S ribosome composed of the large and small subunits, or a complex formed by mixing the 50S subunit and the 30S subunit together which were individually purified.

On the other hand, in eukaryotes, the ribosome and the subunits constituting it have the following sizes: ribosome (80S)=large subunit (60S)+small subunit (40S). Therefore, in cases where the cell-free translation system is to be constituted with ribosomes derived from a eukaryote, ribosomes purified as 80S ribosomes can be used.

Examples of the factors other than ribosomes to be added to the cell-free translation system include the following factors. These factors are not limited to factors derived from prokaryotes such as E. coli, and factors derived from eukaryotes may also be used. These factors and the methods for purifying these factors are known (JP 2003-102495 A).

Initiation Factors (IFs)
Elongation factors (EFs)
Aminoacyl-tRNA synthetase
Methionyl-tRNA transformylase (MTF)

Although a releasing factor may also be contained, a releasing factor is preferably not contained, for stable maintenance of the complex between the protein and the polynucleotide on the ribosome.

The initiation factor is a factor that is indispensable for, or that remarkably promotes, formation of an initiation complex. As initiation factors derived from E. coli, IF1, IF2 and IF3 are known (Claudio O et al. (1990) Biochemistry, vol. 29, p. 5881-5889). The initiation factor IF3 promotes dissociation of the 70S ribosome into the 30S subunit and the 50S subunit, which is a step necessary for initiation of translation, and inhibits insertion of tRNAs other than formylmethionyl tRNA into the P site upon formation of the initiation complex. The initiation factor IF2 is bound to formylmethionyl tRNA and carries the formylmethionyl tRNA to the P site of the 30S ribosome subunit, to form an initiation complex. The initiation factor IF1 promotes the functions of the initiation factors IF2 and IF3. For example, in cases where initiation factors derived from E. coli are used, they may be used at 0.01 μM to 300 μM, preferably 0.04 μM to 60 μM.

As elongation factors derived from E. coli, EF-Tu, EF-Ts and EF-G are known. As the elongation factor EF-Tu, two types, the GTP type and the GDP type, are known, and the GTP type is bound to an aminoacyl-tRNA and carries the aminoacyl-tRNA to the A site of the ribosome. When EF-Tu is released from the ribosome, GTP is hydrolyzed to cause its conversion to the GDP type (Pape T et al, (1998) EMBO J, vol. 17, p. 7490-7497). The elongation factor EF-Ts is bound to EF-Tu (GDP type), to promote its conversion to the GTP type (Hwang Y W et al. (1997) Arch. Biochem. Biophys., vol. 348, p. 157-162). The elongation factor EF-G promotes the translocation reaction after the peptide bond formation reaction in the process of the peptide chain elongation (Agrawal R K et al, (1999) Nat. Struct. Biol., vol. 6, p. 643-647, Rodnina MW. et al, (1999) FEMS Microbiology Reviews, vol. 23, p. 317-333). For example, in cases where elongation factors derived from E. coli are used, they may be used at 0.005 μM to 200 μM, preferably 0.02 μM to 50 μM.

The aminoacyl-tRNA synthetase (AARS) is an enzyme that covalently binds an amino acid to a tRNA in the presence of ATP to synthesize an aminoacyl-tRNA, and there are specific relationships between amino acids and aminoacyl-tRNA synthetases (Francklyn C et al, (1997) RNA, vol. 3, p. 954-960; Proteins, Nucleic Acids and Enzymes, vol. 39, p. 1215-1225 (1994)). For example, in cases where aminoacyl-tRNA synthetases derived from E. coli are used, they may be used at 0.01 μg/ml to 10,000 μg/ml, preferably 0.05 μg/ml to 5,000 μg/ml.

Methionyl-tRNA transformylase (MTF) is an enzyme that synthesizes N-formylmethionyl (fMet) initiation tRNA, wherein a formyl group is attached to the amino group of methionyl initiation tRNA, in protein synthesis in prokaryotes. That is, methionyl-tRNA transformylase transfers the formyl group of FD to the amino group of the methionyl initiation tRNA corresponding to the initiation codon, to form the fMet-initiation tRNA (Ramesh V et al, (1999) Proc. Natl. Acad Sci. USA, vol. 96, p. 875-880). The attached formyl group is recognized by the initiation factor IF2 and acts as the initiation signal for protein synthesis. The protein synthesis system in the cytoplasm of eukaryotes does not have MTF, but the protein synthesis systems in mitochondria and chloroplasts in eukaryotes have MTF. Preferred examples of the MTF include those derived from E. coli, such as the one obtained from the E. coli K12 strain. In cases where MTF derived from E. coli is used, it may be used at, for example, 100 U/ml to 1,000,000 U/ml, preferably 500 U/ml to 400,000 U/ml. The activity herein is defined as 1 U when 1 pmol of fMet-initiation tRNA is formed in 1 minute. The formyl donor (FD) as the substrate of MTF may be used at, for example, 0.1 μg/ml to 1000 μg/ml, preferably 1 μg/ml to 100 μg/ml.

In cases where the polynucleotide to be added to the reaction liquid is DNA, RNA polymerase for transcription into mRNA may be contained. More specifically, the following RNA polymerases may be used. These RNA polymerases are commercially available.

T7 RNA polymerase
T3 RNA polymerase
SP6 RNA polymerase

In cases where T7 RNA polymerase is used, it may be used at 0.01 µg/ml to 5000 µg/ml, preferably 0.1 µg/ml to 1000 µg/ml. Further, in cases where a reconstruction-type cell-free translation system is used in CIS display for increasing the efficiency of formation of the complex between Fab and DNA, endogenous RNA polymerase purified from *E. coli* may be added as described in Nucleic Acid Research 2010, vol. 38, No. 13, e141. Further, a transcription termination factor rho protein purified from *E. coli* may also be added as described in Nucleic Acid Research 1988, vol. 16, No. 14, 6493.

The cell-free translation system may also contain, in addition to the factors for transcription and translation, auxiliary components. Examples of the auxiliary components include the following components.

Enzymes for regeneration of energy in the reaction system:
  creatine kinase;
  myokinase;
  nucleoside diphosphate kinase; and the like.

Enzymes for degradation of inorganic pyrophosphate produced in transcription/translation:
  Inorganic pyrophosphatase; and the like.

The above enzymes may be used at, for example, 0.01 µg/ml to 2000 µg/ml, preferably 0.05 µg/ml to 500 µg/ml.

The cell-free translation system preferably contains amino acids, nucleoside triphosphates, tRNAs and salts. Further, in cases where the reaction system is derived from a prokaryotic cell such as *E. coli*, the cell-free translation system preferably contains the methionyl-tRNA transformylase and 10-formyl 5,6,7,8-tetrahydrofolate (FD).

As the amino acids, naturally-occurring amino acids as well as non-naturally occurring amino acids may be used. These amino acids are carried by tRNAs by the action of aminoacyl-tRNA synthetases constituting the cell-free translation system. Alternatively, the amino acids may be preliminarily charged to tRNAs before addition into the cell-free translation system. The charging of an amino acid to tRNA herein means that tRNA is made to carry an amino acid such that the amino acid can be used in the translation reaction on a ribosome. By adding non-naturally occurring amino acids in the presence of artificial aminoacyl synthetases that recognize the non-naturally occurring amino acids, or by using tRNAs charged with non-naturally occurring amino acids, the non-naturally occurring amino acids can be introduced into specific codon sites of the protein. In cases where naturally occurring amino acids are used, they may be used at 0.001 mM to 10 mM, preferably 0.01 mM to 2 mM.

As the tRNAs, tRNAs purified from cells of *E. coli*, yeast or the like may be used Artificial tRNAs wherein anticodons and/or other bases are artificially modified may also be used (Hohsaka, T et al. (1996) J. Am. Chem. Soc., vol. 121, p. 34-40, Hirao I et al (2002) Nat. Biotechnol., vol. 20, p. 177-182). For example, by charging a non-naturally occurring amino acid to a tRNA having CUA as the anticodon, the UAG codon, which is originally a stop codon, can be translated to the non-naturally occurring amino acid. Further, by using an artificial aminoacyl-tRNA wherein a non-naturally occurring amino acid is charged to a tRNA having a 4-base codon as the anticodon, the non-naturally occurring 4-base codon can be translated to the non-naturally occurring amino acid (Hohsaka et al. (1999) J. Am. Chem. Soc., vol. 121, p. 12194-12195). As the method for preparing such an artificial tRNA, a method using RNA may also be used (Japanese Translated PCT Patent Application Laid-open No. 2003-514572). By such methods, a protein having site-specifically introduced non-naturally occurring amino acids can be synthesized. In cases where an *E. coli* tRNA mixture is used, the tRNAs may be used at, for example, 0.1 $A_{260}$/ml to 1000 $A_{260}$/ml, preferably 1 $A_{260}$/ml to 500 $A_{260}$/ml.

The reconstruction-type cell-free translation system can be prepared by adding the factors to a buffer with a constant pH of 7 to 8, which is suitable for transcription and translation. Examples of the buffer include potassium phosphate buffer (pH 7.3) and Hepes-KOH (pH 7.6). In cases where Hepes-KOH (pH 7.6) is used, it may be used, for example, at 0.1 mM to 200 mM, preferably 1 mM to 100 mM.

The cell-free translation system may also contain salts for the purposes of protecting the factors and maintaining the activities. Specific examples of the salts include potassium glutamate, potassium acetate, ammonium chloride, magnesium acetate, magnesium chloride and calcium chloride. These salts are used usually at 0.01 mM to 1000 mM, preferably at 0.1 mM to 200 mM.

The cell-free translation system may also contain other low-molecular-weight compounds as substrates for enzymes, and/or for the purpose of increasing or maintaining the activities. Specific examples of the compounds which may be added to the cell-free translation system include substrates such as nucleoside triphosphates (e.g., ATP, GTP, CTP and UTP); polyamines such as putrescine and spermidine; reducing agents such as dithiothreitol (MT); and substrates for regeneration of energy, such as creatine phosphate. These low molecular weight compounds may be used usually at 0.01 mM to 1000 mM, preferably at 0.1 mM to 200 mM.

The cell-free translation system may be prepared according to the specific compositions described in Shimizu et al. (Shimizu et al., Nat. Biotechnol. (2001) vol. 19, p. 751-755; Shimizu et al., Methods (2005) vol. 36, p. 299-304) or Ying et al. (Ying et al., Biochem. Biophys. Res. Commun. (2004) vol. 320, p. 1359-1364). However, the concentration of each factor may be increased or decreased as appropriate depending on the specific activity and/or the purpose of the purified factor. For example, in cases where the energy consumption is high, ATP may be increased. Further, depending on the codon usage in the mRNA to be translated, specific tRNAs may be added.

In cases where the protein is one which hardly forms a higher order structure, a group of proteins called molecular chaperones may be contained. Specific examples of the molecular chaperones which may be added to the cell-free translation system include Hsp100, Hsp90, Hsp70, Hsp60, Hsp40, Hsp10 and low molecular weight Hsp, and their homologues; and trigger factors in *E. coli*. Molecular chaperones are proteins known to assist formation of higher order structures of proteins and prevent aggregation of proteins in the cell (Bukau and Horwich, Cell (1998) vol. 92, p. 351-366; Young et al., Nat. Rev. Mol. Cell Biol (2004) vol. 5, p. 781).

When Fab is expressed, disulfide bonds are formed in the molecule, so that the oxidation-reduction potential of the reaction liquid is important. Therefore, DTT as a reducing agent may be removed from the reaction liquid, and/or a cell-free translation system supplemented with glutathione may be used. Further, a cell-free translation system supplemented with an enzyme(s) that promote(s) disulfide bonding and/or correct the bonds may be used Specific examples of such enzymes include protein disulfide isomerase (PDI) present in ER of eukaryotic cells, and DsbA and DsbC in *E. coli*.

By introducing the polynucleotide construct into the cell-free translation system as described above to perform translation reaction, Fab can be obtained. The obtained Fab may be purified using an affinity column and/or the like.

<Screening Method>

The screening method of the present invention comprises the steps of (i) introducing a polynucleotide construct encoding a Fab library into a cell-free translation system to synthesize Fabs, and displaying the synthesized Fabs on the polynucleotides encoding the Fabs; (ii) bringing the Fabs displayed on the polynucleotides into contact with an antigen; (iii) selecting a Fab of interest that reacts with the antigen; and (iv) amplifying the polynucleotide encoding the Fab of interest.

In the cell-free translation system as described above, Fab is displayed on a ribosome and/or mRNA based on the given genetic information. In ribosome display, the polypeptide containing Fab is kept accompanied by the genetic information (mRNA) encoding it by stalling of the ribosome on mRNA due to the presence of a ribosome stall sequence at the 3'-end. That is, a complex of the 3 factors, mRNA-ribosome-polypeptide is formed. On the other hand, in mRNA display utilizing puromycin or a derivative thereof, the C-terminus of the polypeptide containing Fab is covalently bound to the puromycin or a derivative thereof due to the presence of the puromycin or a derivative thereof at the 3'-end of the polynucleotide construct (mRNA), and the link between the polypeptide containing Fab and the mRNA encoding it is maintained. Further, in CIS display, the polypeptide containing Fab is expressed as a fusion protein with a DNA-binding protein, and the link between the polypeptide containing Fab and the DNA encoding it is maintained by binding of the DNA-binding protein to its target sequence on the DNA. In either method, by selecting Fabs bound to the antigen and recovering mRNAs bound thereto, the genetic information of the Fabs is also recovered. From the mRNAs in the complexes each containing a Fab bound to the target antigen and mRNA, cDNAs are synthesized, and the cDNAs are then amplified by PCR. Transcription/translation reaction is then performed again. By repeating these steps, antibodies against the antigen of interest can be obtained.

The above process is described below more concretely.

The size of the Fab gene library is usually not less than $1\times10^8$, preferably not less than $1\times10^9$, more preferably not less than $1\times10^{10}$, still more preferably not less than $1\times10^{12}$.

The Fab library expressed from the Fab gene library is brought into contact with the target substance (antigen), and Fabs that bind to the target substance are selected from the Fab library, followed by amplification of the polynucleotides encoding the Fabs.

For selection of the Fabs bound to the target substance, the Fabs bound to the target substance need to be screened from numerous Fabs that are not bound to the target substance. This is carried out by the known method called panning (Coomber (2002) Method Mol. Biol., vol. 178, p. 133-145). A basic protocol for panning is as follows.

(1) The Fab library is brought into contact with the target substance. The target substance may be bound to a carrier such as a bead, plate or column, and a sample containing the complex between the Fab and the polynucleotide may be brought into contact therewith (solid-phase selection). Alternatively, selection in the liquid phase may be carried out wherein, for example, the target substance is biotinylated and bound to the Fab, and the complex between the target substance and the Fab is recovered with streptavidin magnetic beads. Further, the solid-phase selection and the liquid-phase selection may be used in combination. By carrying out a plurality of rounds of screening such that the solid-phase selection is first performed and the liquid-phase selection is performed later, high-affinity antibodies can be efficiently selected.

(2) Other Fabs which are unbound to the target substance and contained in the library are removed. For example, such Fabs can be removed by washing. The washing can be carried out with a washing liquid which is used for washing after usual antigen-antibody reaction, and, in cases where screening is carried out for obtaining a Fab having higher affinity than the parent Fab, the washing is preferably carried out under conditions where the bond between the parent Fab and the antigen is maintained while weaker bonds are removed.

(3) The Fabs that were not removed, that is, the Fabs that were specifically bound to the target substance, are recovered.

(4) The operations of (1) to (3) are repeated a plurality of times as required.

In cases of ribosome display, mRNA display or CIS display, when the series of steps are repeated, the polynucleotide in the recovered complex containing the polypeptide-polynucleotide is amplified before Step (1). For example, mRNA can be amplified by RT-PCR. By the RT-PCR, DNA is synthesized using the mRNA as a template. The DNA may be transcribed into mRNA again to use it for formation of the complex. FIGS. 7 and 8 are schematic diagrams showing examples of the screening method for Fab, wherein the series of operations, that is, transcription of DNAs into mRNAs; translation of the mRNAs to produce Fabs; selection of Fabs bound to an antigen; and recovery and amplification of the mRNAs therefrom; are shown.

By the above operations, polynucleotides encoding Fabs that specifically bind to the antigen of interest are enriched. The amino acid sequence information of the Fab of interest can be identified by analyzing the sequence of the obtained polynucleotide.

In cases where an antibody against the antigen of interest has already been obtained and the sequences of the CDRs of the antibody are known, an antibody having even higher affinity can be obtained by using the screening method of the present invention.

That is, the present invention provides a method for screening Fab, which method comprises the steps of:

(I) providing a plurality of types of the polynucleotide construct of the present invention, in each of which the Fab first chain-coding sequence or the Fab second chain-coding sequence encodes an amino acid sequence comprising a single amino acid substitution at a single position in a CDR in the amino acid sequence of the Fab first chain or the Fab second chain of the parent antibody, such that single amino acid substitutions are contained for a plurality of positions in the CDRs of the Fab first chain and the Fab second chain;

(II) carrying out first screening wherein the Steps (i) to (iv) are repeated using the plurality of types of the polynucleotide construct, to screen a plurality of high-affinity Fabs;

(III) analyzing single amino acid substitutions at respective positions in the CDRs of the Fab first chain and the Fab second chain in the plurality of Fabs selected in the first screening step;

(IV) providing the polynucleotide construct of the present invention wherein the Fab first chain-coding sequence and the Fab second chain-coding sequence encode amino acid sequences comprising combinations of the single amino acid substitutions identified in the first screening at the respective positions in the CDRs of the Fab first chain and Fab second chain sequences of the parent antibody; and (V) carrying out second screening wherein the Steps (i) to (iv) are repeated using the polynucleotide construct, to screen a high-affinity Fab.

The "plurality" in Step (I) is not restricted as long as it is 2 or more, and the "plurality" preferably means the number of all amino acids in the CDRs.

The screening method for increasing the affinity of Fab is concretely described below.

However, the screening method of the present invention is not limited to this embodiment.

First, the amino acid sequence (parent sequence) of an antibody (parent antibody) against the antigen of interest is provided. Subsequently, as shown in FIG. 24, polynucleotide constructs of the present invention each containing: an H chain-coding sequence having the same amino acid sequence as in the parent antibody except that one of the total amino acids in the CDRs of the H chain (8 amino acids in CDR-H1, 11 amino acids in CDR-H2 and 12 amino acids in CDR-H3—a total of 31 amino acids) has a single amino acid substitution (which preferably allows appearance of all 20 naturally-occurring amino acids including the parent amino acid); and the L chain-coding sequence of the parent antibody; are provided in a number equal to the number of all amino acids (31 amino acids in total) in the CDRs of the H chain (H-chain library).

Further, polynucleotide constructs each containing: an L chain-coding sequence having the same amino acid sequence as in the parent antibody except that one of the total amino acids in the CDRs of the L chain (7 amino acids in CDR-L1, 6 amino acids in CDR-L2 and 6 amino acids in CDR-L3—a total of 19 amino acids) has a single amino acid substitution (which preferably allows appearance of all 20 naturally-occurring amino acids including the parent amino acid); and the H chain-coding sequence of the parent antibody; are provided in a number equal to the number of all amino acids (19 amino acids in total) in the CDRs of the L chain (L-chain library).

Using the above H-chain library and the L-chain library as a primary library, Steps (i) to (iv) are repeated to carry out screening of high-affinity antibodies (first screening)

Since the polynucleotide sequences encoding the high-affinity antibodies are enriched by the first screening, the plurality of enriched sequences are analyzed to select amino acid substitutions frequently observed at respective positions in the CDRs of the H chain and the L chain as amino acid substitutions preferred for increasing the affinity Although sequence analysis of the polynucleotides can be carried out by conventional sequencing, a next-generation sequencer is preferably used since cloning of the Fab-coding sequences amplified by the screening is not necessary; large-scale comprehensive sequence analysis is possible; and the time required for screening can be largely reduced.

There term "next-generation sequencer" herein is used in contrast to the first-generation sequencer represented by the fluorescent capillary sequencer utilizing the Sanger sequencing method. This term actually includes various apparatuses and techniques, and invention of various modes of such a sequencer can be expected also in the future (Mardis, Annu. Rev. Genom. Human Genet. (2008) vol. 9, p. 387-402; Persson et al., Chem. Soc. Rev. (2010) vol. 39, p. 985-999).

In contrast to the first-generation sequencer which is generally used for sequencing of DNA cloned using a vector-host system, the next-generation sequencer enables rapid determination of DNA sequences in samples without cloning of DNA using a vector-host system, while DNA samples having various sequences can be analyzed therewith.

In determination of DNA sequences using a first-generation sequencer, the DNA sequences of individual clones are determined by the following process:

(i) incorporation of each DNA fragment into a vector such as a plasmid, and transformation of a host such as *E. coli* with the resultant;

(ii) cloning by isolation of host colonies;

(iii) culture of clones in a number dependent on the scale of the analysis, and extraction of their plasmids;

(iv) sequencing reaction by PCR or the like using each plasmid or the like as a template; and (v) separation, detection and analysis of the sequencing reaction product by capillary electrophoresis and/or the like. In cases where the DNA sequences of a large number of clones are to be determined at once, the reactions/treatments in the Steps (ii) to (v) after cloning need to be carried out separately for each clone, so that the amount of labor required is proportional to the number of clones to be analyzed.

On the other hand, in DNA sequencing using a next-generation sequencer, DNA fragments having various sequences are individually cloned on a vast number of analytical spots on a substrate for analysis and subjected to massively parallel sequence analysis, by application of an amplification technique such as single-molecule PCR including Emulsion PCR and Bridge PCR, or a highly sensitive detection technique such as single molecule observation. Therefore, the sequences of, for example, $10^6$ to $10^9$ clones formed on a single substrate for analysis can be determined by a single reaction/treatment irrespective of the number of clones to be analyzed.

The next-generation sequencer which is most common at present is based on a principle in which sequential DNA synthesis with DNA polymerase or DNA ligase is used for massively parallel determination of nucleotide sequences by optical detection of fluorescence, luminescence or the like. Examples of known methods using DNA polymerase include GS FLX (Roche Diagnostics) and Solexa (Illumina), and examples of known methods using DNA ligase include SOLiD (Applied Biosystems) and Polonator (Dover Systems). Further, HeliScope (Helicos Biosciences), SMRT (Pacific Biosciences) and the like are known, which determine nucleotide sequences by single-molecule real-time observation wherein a single molecule of DNA is used as a template for synthesis of DNA by DNA polymerase and the reaction for each single base is optically detected with fluorescence, luminescence or the like. Other reported examples include a principle called Post-light sequencing, wherein massively parallel determination of nucleotide sequences is carried out by a detection method other than optical detection of fluorescence, luminescence or the like. Examples of methods that correspond to this principle include Ion Torrent Systems, wherein a semiconductor (CMOS) chip is used to detect hydrogen ions (pH change) released upon incorporation of each base by DNA polymerase, in order to determine nucleotide sequences. Other known examples include Nanopore (Oxford Nanopore Technologies).

The amino acid sequences obtained by the first screening, containing the combinations of single amino acid substitutions in the amino acids of CDRs in the H chain and the L chain, are used as the secondary library. For example, in cases where the first screening suggested that the first amino acid is preferably substituted to Ala or Thr and the second amino acid is preferably substituted to Ile or Leu in the first CDR of the H chain (H1), the library to be used in the second screening, that is, the secondary library, is prepared by designing nucleotide sequences such that the first amino acid is Ala or Thr and the second amino acid is Ile or Leu, and other amino acids also show preferred combinations of amino acids obtained in the first screening. It should be noted that the preferred mutant amino acids obtained in the first screening and the amino acids in the parent sequence may be combined to provide the secondary library.

Using the thus obtained secondary library, Steps (i) to (iv) are repeated to carry out the second screening. By this, many types of antibodies having remarkably improved affinity to the antigen relative to the parent antibody can be obtained. The remarkable improvement of affinity to the antigen relative to the parent antibody can be analyzed by SPR, ELISA or the like.

The polynucleotide construct of the present invention may be used as a component of a kit for production and/or screening of Fabs.

The principle of two-step affinity maturation in the Ymacs method of the present invention, which comprises the steps of searching of potentially beneficial single amino acid substitutions from the primary library and searching of the optimal combination of these beneficial single amino acid substitutions from the secondary library, can be applied to improvement of the affinity of not only Fab fragments of antibodies but also scFv, full-length antibodies and other target-binding proteins to the target, in combination with a wide range of protein display systems.

That is, the present invention provides a method for maximizing the affinity of a target-substance-binding protein to a target substance (method for obtaining a mutant-type target-substance-binding protein having improved affinity to a target substance), which method comprises the steps of:

(I) constructing single-position libraries wherein one amino acid among all amino acid positions constituting a target-substance-binding site in a target-substance-binding protein is randomized to all the 20 types of naturally-occurring amino acids, to provide as many single-position libraries as the number of the all amino acid positions;

(II) constructing a primary library by integrating all of, or an appropriate unit of, these single-position libraries (preparation of primary-library polynucleotide constructs);

(III) selecting the primary library using a protein display system based on the affinity to a target;

(IV) determining the polynucleotide sequence information of the selected sample of the primary library obtained in (III);

(V) extracting single amino acid substitutions frequently observed (preferably 2 or more times) in the nucleotide sequence information;

(VI) constructing a secondary library comprising combinations of the frequently observed single amino acid substitutions (preparation of secondary-library polynucleotide constructs); and (VII) selecting the secondary library using a protein display system based on the affinity to a target.

In cases where the primary library is constructed by integration of an appropriate unit in Step (II), the single-position libraries constructed in Step (I) may be divided into 2 or more groups, to provide 2 or more types of primary libraries. Further, the secondary library constructed in (VI) may contain, in addition to the frequently observed single amino acid substitutions, the parent amino acids encoded by the parent antibody.

Examples of the target-substance-binding protein herein include antigen-binding proteins and cytokines.

Examples of the antigen-binding protein include Fab, scFv and full-length antibodies, and the antigen-binding protein may also be a protein that is not classified as an antibody, as long as it specifically binds to an antigen.

Further, a mutation(s) may also be introduced into a cytokine for increasing its binding capacity to a receptor.

The protein display system is not limited as long as the system allows association of proteins with the polynucleotides encoding them, and examples of the protein display system include not only the above-described cell-free systems such as ribosome display, mRNA display and CIS display, but also other protein display systems such as phage display (Non-patent Document 1), bacterial surface display (Jose, Appl. Microbiol. Biotechnol. (2006) vol. 69, p. 607-614), yeast surface display (Feldhaus et al., Nat. Biotechnol. (2003) vol. 21, p. 163-70), and cell surface display with a higher eukaryote (Horlick, WO2008/103475). The part other than the coding region for the target substance-binding protein in the single-position library polynucleotide may have the same constitution as a known vector for each protein display. The coding region for the target substance-binding protein contained in the library polynucleotide may encode either the full-length of the target substance-binding protein or a part of the target substance-binding protein wherein the target substance-binding site is contained.

A more concrete description is given below by way of an example.

For example, in cases where the target substance-binding site in the target substance-binding protein (wild type) is a region composed of 10 amino acids, a total of 10 types of single-position libraries in each of which 20 amino acids appear at a single position among the 1st to 10th positions are provided.

These 10 types of single-position libraries are combined to prepare a primary library, and this library is subjected to the selection based on the affinity to the target substance. More specifically, the Steps (I') to (iv') described below are repeated to concentrate sequences having high affinity to the target substance (first screening):

(i') the step of introducing the library into a protein display system to allow expression of the target substance-binding proteins, and displaying the target substance-binding proteins on the polynucleotides encoding the proteins;

(ii') the step of bringing the target substance-binding proteins into contact with a target substance;

(iii') the step of selecting target substance-binding proteins of interest that react with the target substance; and (iv') the step of amplifying the polynucleotides encoding the target substance-binding proteins of interest.

These steps may be carried out in the same manner as the operations in normal protein display.

In Step (ii'), the target substance may be bound to a carrier such as a bead, plate or column, and a sample containing complexes between the target substance-binding proteins and the polynucleotides may be brought into contact therewith (solid-phase selection). Alternatively, selection in the liquid phase may be carried out wherein, for example, the target substance is biotinylated and bound to the target substance-binding proteins, and the complexes between the target substance and the target substance-binding proteins are recovered with streptavidin magnetic beads. Further, the solid-phase selection and the liquid-phase selection may be used in combination. By carrying out a plurality of rounds of screening such that the solid-phase selection is first performed and the liquid-phase selection is performed later, high-affinity proteins can be efficiently selected.

For removing non-specific binding, a washing operation is preferably carried out between (ii') and The washing is preferably carried out under conditions where the bond between the wild-type target substance-binding protein and the target substance is maintained while weaker bonds are removed.

Since the polynucleotide sequences encoding proteins having high affinity to the target substance are enriched by the first screening, the sequences of the plurality of enriched target substance-binding sites are analyzed to select amino acid substitutions frequently observed at respective positions in the CDRs of the H chain and the L chain as amino acid substitutions preferred for increasing the affinity.

Although sequence analysis of the polynucleotides may be carried out by conventional sequencing, a next-generation sequencer is preferably used since cloning of the coding sequences for the target substance-binding proteins amplified by the screening is not necessary; large-scale comprehensive sequence analysis is possible; and the time required for screening can be largely reduced.

There term "next-generation sequencer" herein is used in contrast to the first-generation sequencer represented by the fluorescent capillary sequencer utilizing the Sanger sequencing method. This term actually includes various apparatuses and techniques, and invention of various modes of such a sequencer can be expected also in the future (Mardis, Annu. Rev. Genom. Human Genet. (2008) vol. 9, p. 387-402; Persson et al., Chem. Soc. Rev. (2010) vol. 39, p. 985-999).

In contrast to the first-generation sequencer which is generally used for sequencing of DNA cloned using a vector-host system, the next-generation sequencer enables rapid determination of DNA sequences in samples without cloning of DNA using a vector-host system, while DNA samples having various sequences can be analyzed therewith.

In determination of DNA sequences using a first-generation sequencer, the DNA sequences of individual clones are determined by the following process:
  (i) incorporation of each DNA fragment into a vector such as a plasmid, and transformation of a host such as $E.\ coli$ with the resultant;
  (ii) cloning by isolation of host colonies;
  (iii) culture of clones in a number dependent on the scale of the analysis, and extraction of their plasmids;
  (iv) sequencing reaction by PCR or the like using each plasmid or the like as a template; and
  (v) separation, detection and analysis of the sequencing reaction product by capillary electrophoresis and/or the like.
In cases where the DNA sequences of a large number of clones are to be determined at once, the reactions/treatments in the Steps (ii) to (v) after cloning need to be carried out separately for each clone, so that the amount of labor required is proportional to the number of clones to be analyzed.

On the other hand, in DNA sequencing using a next-generation sequencer, DNA fragments having various sequences are individually cloned on a vast number of analytical spots on a substrate for analysis and subjected to massively parallel sequence analysis, by application of an amplification technique such as single-molecule PCR including Emulsion PCR and Bridge PCR, or a highly sensitive detection technique such as single molecule observation. Therefore, the sequences of, for example, $10^6$ to $10^9$ clones formed on a single substrate for analysis can be determined by a single reaction/treatment irrespective of the number of clones to be analyzed.

The next-generation sequencer which is most common at present is based on a principle in which sequential DNA synthesis with DNA polymerase or DNA ligase is used for massively parallel determination of nucleotide sequences by optical detection of fluorescence, luminescence or the like. Examples of known methods using DNA polymerase include GS FLX (Roche Diagnostics) and Solexa (Illumina), and examples of known methods using DNA ligase include SOLiD (Applied Biosystems) and Polonator (Dover Systems). Further, HeliScope (Helicos Biosciences), SMRT (Pacific Biosciences) and the like are known, which determine a nucleotide sequence by single-molecule real-time observation wherein a single molecule of DNA is used as a template for synthesis of DNA by DNA polymerase and the reaction for each single base is optically detected with fluorescence, luminescence or the like. Other reported examples include a principle called Post-light sequencing, wherein massively parallel determination of nucleotide sequences is carried out by a detection method other than optical detection of fluorescence, luminescence or the like. Examples of methods that correspond to this principle include Ion Torrent Systems, wherein a semiconductor (CMOS) chip is used to detect hydrogen ions (pH change) released upon incorporation of each base by DNA polymerase, in order to determine nucleotide sequences. Other known examples include Nanopore (Oxford Nanopore Technologies).

By comprehensively analyzing the sequences obtained by the first screening using a next-generation sequencer, the sequences can be used in the second screening without cloning (cloning into a vector followed by expression of the individual sequences), so that the time required for screening can be largely reduced, which is advantageous. However, the sequences may be partially cloned and subjected to investigation of the binding capacity for the purpose of, for example, confirmation of the efficiency of the first screening.

Subsequently, the single amino acid substitutions of the respective amino acids in the target substance-binding site, obtained by the sequence analysis in the first screening, are combined to prepare the secondary library. For example, in cases where the first screening suggested that the first amino acid is preferably substituted to Ala or Thr and the second amino acid is preferably substituted to Ile or Leu in the target substance-binding site, the library to be used in the second screening, that is, the secondary library, is prepared by designing nucleotide sequences such that the first amino acid is Ala or Thr and the second amino acid is Ile or Leu, and other amino acids also show preferred combinations of amino acids obtained in the first screening. It should be noted that the preferred mutant amino acids obtained in the first screening and the amino acids in the parent sequence may be combined to provide the secondary library.

Using this secondary library, Steps (i') to (iv') are repeated to carry out the second screening. By this, many types of proteins having remarkably improved affinity to the target substance relative to the parent protein can be obtained. The remarkable improvement of affinity to the target substance relative to the parent protein can be analyzed by SPR, ELISA or the like.

EXAMPLES

The present invention is described below more concretely by reference to Examples. However, the present invention is not limited to the embodiments below.

[Example 1] Preparation of Model Fab

As the framework of the Fab to be used in the cell-free Fab display system, the combination of VL k subgroup I and VH subgroup III, which is one of the major antibody subclasses in human, excellent in expression efficiency in *E. coli* (Kanappik et al., J Mol Biol. (2000) vol. 296, p. 57-86) and reported to be effective in a cell-free scFv display system (Shibui et al., Appl Microbiol Biotechnol. (2009) vol. 84, p. 725-732), was selected. As a model Fab having the above-described framework to be used for confirmation of the performance of the cell-free Fab display system, the human EGFR-2 (Her-2)-reactive Fab reported by Carter et al. (Carter et al., Proc Natl Acad Sci USA. (1992) vol. 89, p. 4285-4289) was selected to provide Fab-HH.

As another model Fab, Fab-TT was provided by substituting the CDR 1-3 regions in the L chain and the H chain of Fab-HH by the sequence of the TNFαR-reactive scFv discovered by the cell-free scFv display system by Shibui et al. (Shibui et al., Biotechnol. Lett. (2009) vol. 31, p. 1103-1110).

cDNAs encoding the VL domain and the VH domain of these 2 types of model Fabs were artificially synthesized. Further, cDNAs encoding the CL domain and the CH1 domain were obtained by PCR using the genomic DNA of a human cancer cell line as a template. The obtained cDNA fragments were incorporated into an *E. coli* expression vector pTrc99A to construct pTrc Fab-HH and pTrc Fab-TT as vectors to be used for bicistronic secretory expression of the model Fabs. Further, the original combinations of the L chain and the H chain were intentionally changed to provide Fab-HT (the combination of the Her-2-reactive L chain and the TNFαR-reactive H chain) and Fab-TH (the combination of the TNFαR-reactive L chain and the Her-2-reactive H chain), and pTrc Fab-HT and pTrc Fab-TH which express these were constructed. In this process, a myc tag was attached to the C-terminus of the L chain, and a dual FLAG tag and a His tag were consecutively attached to the C-terminus of the H chain. A schematic view of the structure of the unit that bicistronically expresses Fab in the pTrc Fab vector is shown in FIG. 9.

The nucleotide sequence of pTrc Fab-HH is shown in SEQ ID NO:1, and the amino acid sequence encoded thereby is shown in SEQ ID NOs:2 and 3. The nucleotide sequence of pTrc Fab-TT is shown in SEQ ID NO:4, and the amino acid sequence encoded thereby is shown in SEQ ID NOs:5 and 6. The nucleotide sequence of pTrc Fab-HT is shown in SEQ ID NO:7, and the amino acid sequence encoded thereby is shown in SEQ ID NOs:8 and 9. The nucleotide sequence of pTrc Fab-TH is shown in SEQ ID NO:10, and the amino acid sequence encoded thereby is shown in SEQ ID NOs:11 and 12.

The *E. coli* DH5α strain having the pTrc Fab vector was cultured in LB medium supplemented with 100 μg/ml ampicillin, and IPTG was added thereto during the logarithmic phase at a final concentration of 0.1 mM to induce expression of the model Fab into the culture supernatant. The culture supernatant was recovered 18 hours after the addition of IPTG, and the model Fab contained therein was bound to Ni-NTA agarose beads (QIAGEN) using the His tag attached at the C-terminus of the H chain. After washing the beads, elution was carried out with PBS supplemented with imidazole at a final concentration of 250 mM. The eluted fraction was dialyzed against PBS, to prepare a high-purity model Fab. The concentration of the model Fab was calculated based on the absorbance at 280 nm under the assumption of 1 OD=1 mg/ml. The model Fab samples were separated by 5-20% gradient gel SDS-PAGE, followed by staining with Coomassie Blue. The result is shown in FIG. 10. It can be seen that the purity of each prepared model Fab is sufficient.

[Example 2] Evaluation of Activities, Specificities and L Chain-H Chain Interdependencies of Model Fabs Each of Her-2 and TNFαR (R&D systems) as an antigen protein for the model Fab was diluted with PBS to 1 μg/ml. The diluted antigen was placed on an ELISA plate, and immobilized on the plate by incubation at 4° C. overnight. After washing the well, the model Fab was added thereto to bind the model Fab to the antigen. After washing the well, a 1000-fold diluted HRP-labeled anti-FLAG antibody (Sigma) as a detection antibody was added to the well, to bind the detection antibody to the FLAG tag attached to the model Fab. After washing the well, a colorimetric substrate for HRP was added thereto. When an appropriate degree of coloring was achieved, a stop solution was added to the well, and the absorbance was measured at OD 405 nm. FIG. 11 shows the result of titration of the 4 types of model Fabs over a wide range of concentration using Her-2 as the antigen protein. It can be seen that Fab-HH binds to Her-2 strongly (ED50=2 nM). FIG. 12 shows the result obtained by bringing each of the 4 types of model Fabs at high concentrations (7.1, 1.8, 2.9 and 5.8 μM, respectively, for HH, TT, HT and TH) into contact with each of the two types of antigen proteins. It can be seen that Fab-HH binds to Her-2 but does not bind to TNFαR, and that Fab-TT binds to TNFαR but does not bind to Her-2. Further, since neither of the hybrid Fabs, Fab-HT and Fab-TH, binds to any of the antigens, it can be seen that the binding of Fab-HH to Her-2 and the binding of Fab-TT to TNFαR are L chain-H chain interdependent, and that a correct combination of the L chain and the H chain is necessary for binding to an antigen protein.

[Example 3] Construction of Vector for Bicistronic Fab-PRD

A sequence having a very similar amino acid sequence to that of the above-described Fab-HH and reported by Fellouse et al. (Fellouse et al., J. Mol. Biol. (2007) vol. 373, p. 924-940) to show even higher expression efficiency in *E. coli* was provided as Fab-SS. For the display of this sequence in a cell-free system, a DNA fragment for bicistronic Fab-PRD was artificially synthesized using codons optimized for *E. coli*. The synthesized fragment was incorporated into a general-purpose phagemid vector pBluescript SK(+) to construct pGAv2-SS. Subsequently, the CDR 1-3 regions in the L chain and the CDR 1-3 regions in the H chain of pGAv2-SS were replaced by the corresponding regions in pTrc Fab-HH, to construct pGAv2-HH. Similarly, using pGAv2-SS and pTrc Fab-TT, pGAv2-TT was constructed. Subsequently, by introducing a XhoI recognition site into the most downstream part of the GS linker downstream of the L chain of pGAv2-HH without changing the amino acid sequence, pGAv2-HH xhoI was constructed. A schematic view of the structure of the DNA fragment for bicistronic Fab-PRD is shown in FIG. 13.

[Example 4] Construction of Vector for Monocistronic Fab-PRD

In pGAv2-HH xhoI and pGAv2-TT for bicistronic Fab-PRD, the region from the first amino acid in the ribosome stall sequence downstream of the L chain to the first methionine in the H chain was replaced by a sequence encoding a FLAG tag and, via this FLAG tag, the C-terminus of the GS linker downstream of the L chain was linked in-frame to the H chain, to construct vectors for monocistronic Fab-PRD, pGAv6-HH xhoI and pGAv6-TT. A schematic view of the structure of the DNA fragment for monocistronic Fab-PRD is shown in FIG. 14.

[Example 5] Preparation of Template DNA

Template DNA fragments for in vitro transcription were amplified by PCR using, as a template, each of pGAv2-HH xhoI and pGAv2-TT for bicistronic Fab-PRD and each of pGAv6-HH xhoI and pGAv6-TT for monocistronic Fab-PRD. As an enzyme for PCR, PrimeStarMax (Takara) was used, and, as primers, the combination of PURE-rt-1F and PURE-3R or the combination of SL-1F and SL-2R was used. The amplified template DNA fragments for in vitro transcription were purified by phenol/chloroform extraction and isopropanol precipitation. The concentration of each template DNA fragment for in vitro transcription was calculated based on the absorbance at 260 nm under the assumption of 1 OD=50 μg/ml. The sequences of the template DNA fragments for in vitro transcription amplified from the 4 types of vectors using the primer set of SL-1F and SL-2R were as follows.
For Bicistronic Fab-PRD
    pGAv2-HH xhoI, SEQ ID NO:13 (for the amino acid sequence, see SEQ ID NOs:14 (L) and 15 (H))
    pGAv2-TT, SEQ ID NO:16 (for the amino acid sequence, see SEQ ID NOs:17 (L) and 18 (H))
For monocistronic Fab-PRD
    pGAv6-HH xhoI, SEQ ID NO:19 (for the amino acid sequence, see SEQ ID NO:20)
    pGAv6-TT, SEQ ID NO:21 (for the amino acid sequence, see SEQ ID NO:22)
The sequences of the primers used were as follows.

```
PURE-rt-1F:
                                         (SEQ ID NO: 23)
(caatttcggtaatacgactcactatagggagaatttaggtgacact atagaagtg)

PURE-3R:
                                         (SEQ ID NO: 24)
(caggtcagacgattggccttg)

SL-1F:
                                         (SEQ ID NO: 25)
(caatttcggtaatacgactcactatagggagaccacaacggtttcc catttaggtgacactatagaagtg)

SL-2R:
                                         (SEQ ID NO: 26)
(ccgcacaccagtaaggtgtgcggcaggtcagacgattggccttgat attcacaaacg)
```

[Example 6] mRNA Synthesis mRNA synthesis was carried out using 500 ng of a template DNA fragment and 2.7 μg of purified T7 RNA polymerase, at a scale of 50 μl. After the synthesis reaction at 37° C. for 60 minutes, 1 μl of RNase-free DNase (Promega) was added to the reaction solution to degrade the template DNA by the reaction at 37° C. for 10 minutes. The mRNA was purified by phenol/chloroform extraction and isopropanol precipitation, and dissolved in 30 μl of nuclease-free water (Promega). The concentration of the mRNA was calculated based on the absorbance at 260 nm under the assumption of 1 OD=40 μg/ml.

[Example 7] Translation of mRNA by Reconstruction-Type Cell-Free Translation System (PURE System)

The translation factors and the ribosomes constituting the PURE system were prepared according to the methods described in reports by Shimizu et al. (Shimizu et al., Nat Biotechnol. (2001) vol. 19, p. 751-755) and Ohashi et al. (Ohashi et al., Biochem Biophys Res Commun. (2007) vol. 352, p. 270-276). Translation reaction was carried out using 2 pmol of mRNA and 20 pmol of ribosomes at a scale of 20 μl. In terms of the oxidation-reduction conditions, oxidized glutathione and reduced glutathione, and protein disulfide isomerase were removed, and 1 mM DTT was added to perform the translation reaction under reducing conditions. After the translation reaction at 37° C. for 20 minutes, oxidized glutathione was added at a final concentration of 2.5 mM to neutralize DTT.

[Example 8] Biotinylation, and Confirmation of Quality of Antigen

Each of Her-2 and TNFαR (R&D systems) was dissolved in PBS at 0.5 mg/ml. As a biotinylation reagent, 1.1 μl (for Her-2) or 3.6 μl (for TNFαR) of Sulfo-NHS-SS-Biotin (Thermo Scientific) prepared at a concentration of 0.6 mg/ml (for Her-2) or 4.0 mg/ml (for TNFαR) in PBS was added to 100 μl of the antigen solution, and the reaction was allowed to proceed at mom temperature of 1 hour. The reaction product was passed through a gel filtration spin column to remove unreacted biotinylation reagent. Avidin (Calbiochem) was diluted to 2 μg/ml with PBS. The diluted avidin was placed on an ELISA plate and incubated at 4° C. overnight for immobilization on the plate. After washing the well, the biotinylated antigen was added thereto to bind the biotinylated antigen to the avidin After washing the well, the high-purity model Fab prepared in Example 1 was added thereto to bind the model Fab to the biotinylated antigen. After washing the well, a 1000-fold diluted HRP-labeled anti-FLAG antibody (Sigma) as a detection antibody was added to the well, to bind the detection antibody to the FLAG tag attached to the model Fab. After washing the well, a colorimetric substrate for HRP was added thereto. When an appropriate degree of coloring was achieved, a stop solution was added to the well, and the absorbance was measured at OD 405 nm. The obtained result is shown in FIG. 15. It can be seen that the 2 types of biotinylated antigens have simultaneous reactivity to avidin and the corresponding model Fab.

[Example 9] Selection of Fab by PRD (Fab-PRD)

By reference to the method reported by Ohashi et al. (Ohashi et al., Biochem Biophys Res Commun. (2007) vol. 352, p. 270-276), in vitro selection of Fab was carried out by ribosome display based on the PURE system (PRD). Thirty microliters of M-280 streptavidin magnetic beads (DYNAL) were washed, and 5 pmol of the biotinylated antigen protein prepared in Example 8 was added thereto, followed by allowing the reaction to proceed at room temperature for 30 minutes in order to immobilize the bait protein on the magnetic beads. The magnetic beads were washed to provide beads for selection. By the same procedure, beads for preclearing, on which the bait protein was not immobilized, were prepared.

A small amount of Fab-HH xho was added to Fab-TT as a template DNA or mRNA to an arbitrary content, to provide a sample before selection. This sample was used to prepare an in vitro translation product by the method described in Example 7. The prepared product was mixed with the beads for preclearing, and the reaction was allowed to proceed at 4° C. for 30 minutes, followed by recovering the supernatant. The supernatant was mixed with the beads for selection, and the reaction was allowed to proceed at 4° C. for 30 minutes, followed by recovering the magnetic beads. The magnetic beads were washed, and 100 µl of an elution buffer was added thereto, followed by allowing the reaction to proceed at mom temperature for 10 minutes. The elution buffer was prepared using (50 mM Tris-Cl pH 7.6, 150 mM NaCl, 10 µg/ml budding yeast RNA) as a base, and DTT was further added thereto to a final concentration of 100 mM in the case of reducing elution, or EDTA was added thereto to a final concentration of 50 mM in the case of chelate elution. The mRNA bound to the magnetic beads via Fab was eluted by reductive cleavage of the S—S bond in the biotin linker, in the case of reducing elution; or by dissociating the display molecule complex (complex of the 3 components, mRNA-ribosome-polypeptide) which is dependent on magnesium ions, in the case of chelate elution. From the eluted sample, mRNA was purified by phenol/chloroform extraction and isopropanol precipitation, or using RNaeasy RNA purification kit (QIAGEN).

By the reaction using SuperScript III (Invitrogen) as reverse transcriptase, the eluted mRNA was converted to cDNA. As a primer for the reverse transcription reaction, PURE-2R or PURE-3R was used. After amplification of cDNA by PCR reaction using PrimeStarMax (Takara), the amplification product was purified by phenol/chloroform extraction and isopropanol precipitation, to provide a DNA sample after selection. As PCR primers for amplification of the full-length sequence of mRNA, the combination of PURE-rt-1F and PURE-3R or the combination of SL-1F and SL-2R was used. Further, as PCR primers for amplification of a partial fragment corresponding to the region from CDR3 in the L chain to CDR1 in the H chain, the combination of L-CDRex-1F and H-CDRex-2R was used. The sequences of the primers used were as shown below.

```
PURE-2R:
                                      (SEQ ID NO: 27)
(gacgattggccttgatattcacaaacg)

L-CDRex-1F:
                                      (SEQ ID NO: 28)
(attaaacgtaccgttgcagcaccgagc)

H-CDRex-2R:
                                      (SEQ ID NO: 29)
(tgagcctccaggctgaaccagaccac)
```

[Example 10] Confirmation of Specific Enrichment by Fab-PRD

The DNA samples before selection and after selection were digested with XhoI, and separated with 1% agarose gel, followed by staining with ethidium bromide. It is expected that the DNA sample before selection is hardly digested with XhoI since it contains Fab-TT as the major component, but the DNA sample after selection has higher sensitivity to XhoI since the content of Fab-HH xho is higher. Based on such an increase in the sensitivity of the DNA sample to XhoI, enrichment of Fab-HH DNA was confirmed. The result of Fab-HH selection by single-round bicistronic or monocistronic Fab-PRD using Her-2 as a bait protein is shown below.

From a sample with a TT/HH ratio of 10, Fab-HH was selected by bicistronic Fab-PRD, and a partial fragment corresponding to the region from CDR3 in the L chain to CDR1 in the H chain was amplified to evaluate the sensitivity to XhoI. The result is shown in FIG. 16. In the cases where an mock elution buffer (WB) which does not contain a component necessary for specific elution such as DTT or EDTA was used, no increase in the sensitivity to XhoI could be observed relative to the DNA sample before selection, either when the selection was carried out using the magnetic beads untreated with biotinylated Her-2 or when the selection was carried out using the magnetic beads treated with biotinylated Her-2. On the other hand, in the cases where the selection was carried out using the magnetic beads treated with biotinylated Her-2 and the elution buffer containing DTT or EDTA was used, an increase in the sensitivity to XhoI could be observed. Based on these results, it can be seen that Fab-HH was specifically enriched.

Similarly, from DNA samples with TT/HH ratios of 10 and 100, Fab-HH was selected by bicistronic Fab-PRD, and the selected Fab-HH was eluted with DTT, followed by amplifying the full-length sequence of mRNA in order to evaluate the sensitivity to XhoI. The result is shown in FIG. 17. In the both cases of TT/HH ratios of 10 and 100, an increase in the sensitivity to XhoI was observed, so that it can be seen that Fab-HH was specifically enriched.

Further, from DNA samples with TT/HH ratios of 100 to 100,000, Fab-HH was selected by monocistronic Fab-PRD. The result is shown in FIG. 18. In the cases of TT/HH ratios of 100 to 1000, an increase in the sensitivity to XhoI was observed, so that it can be seen that Fab-HH was specifically enriched.

[Example 11] Confirmation of In Vitro Translation Product of Monocistronic Fab

By the method described in Example 7, a cell-free translation product was prepared using mRNA for monocistronic Fab-PRD. The translation product was separated by SDS-PAGE with 5-20% gradient gel, and transferred to a PVDF membrane. Western blotting was then performed using a 1000-fold diluted HRP-labeled anti-FLAG antibody (Sigma) as a detection antibody. The result is shown in FIG. 19. It can be seen that, although the full-length translation product of scFab-TT can be observed, the ratio of the full-length translation product is extremely smaller than the amount of scFv-TT translated, which was used as a positive control.

[Example 12] Relationship Between Copy Number and Recovery of SecM

PCR was carried out using pGAv6-HH xhoI as a template to synthesize a DNA fragment in which the ribosome stall sequence (SecM sequence) was duplicated into 2 copies, to provide the v6.5 fragment. By similar PCR, the v6.5-S3 fragment having 3 copies of the SecM sequence, and the v6.5-S4 fragment having 4 copies of the SecM sequence were prepared. Using each prepared template DNA fragment (100% Fab-HH), the recovery of Fab-HH by monocistronic Fab-PRD was measured. The monocistronic Fab-PRD was carried out by the solid-phase selection described in Example 9, and the recovered reverse transcription product was quantified by quantitative PCR using, as samples for preparing a calibration curve, the template DNA fragment at known concentrations. As detection primers to be used for the quantitative PCR, 2 types of primers, the upstream primers and the downstream primers, were prepared, and the recovery (the number of molecules of the 1st strand cDNA/the number of input RNA molecules) was determined for each of the upstream region in the vicinity of CDR-L1 and the downstream region in the vicinity of CDR-H3. The result is shown in FIG. 20. By duplicating the SecM sequence into 2 copies, the recovery of Fab-HH by Fab-PRD increased about 10-fold. In this experiment, increasing of the copy number of the SecM sequence to 3 or more did not further increase the recovery, but it is considered that the recovery might further increase by increasing the copy number of the SecM sequence to 3 or more in cases where the experimental conditions are changed by, for example, extending the period of translation reaction.

The primers used for the quantitative PCR were as follows.

```
Upstream primers for FabHH
RT-1F:
                                      (SEQ ID NO: 33)
gatattcagatgacccagagcccgagc RT-1R:
                                      (SEQ ID NO: 34)
cagcttcggggcttttcctgg Downstream primers for FabHH
HH-4F:
                                      (SEQ ID NO: 35)
ccagggaactttggttactgtttc Model-4R:
                                      (SEQ ID NO: 36)
ctttaaccagacaacccagtgc
```

The sequences downstream of the SecM region in the v6.5, v6.5-S3 and v6.5-S4 DNA fragments used in the Fab-PRD are shown in SEQ ID NOs:37, 40 and 44, respectively.

[Example 13] Relationship Between Linker Length and Enrichment Ratio

The template DNA to be used in monocistronic Fab-PRD has a total of 2 linker sequences which are located between the L chain and the H chain and between the H chain and SecM. In the v6.5 fragment in Example 12, the linker between the L chain and the H chain has a length of 128 amino acids, and the linker between the H chain and SecM has a length of 123 amino acids. In order to study the effect of the linker length on the c enrichment ratio in the monocistronic Fab-PRD, the v6.5 fragment having 2 copies of the SecM sequence was used as the basic structure for modification of each of Fab-HH xhoI and Fab-TT, to prepare the v7 fragment by minimizing the length of the linker between the H chain and SecM, and the v8.1 fragment by minimizing the length of the linker between the L chain and the H chain. The length of the linker between the H chain and SecM in the v7 fragment was 20 amino acids in terms of the length from the cysteine as the last amino acid of the H chain to the alanine as the first amino acid of SecM. The length of the linker between the L chain and the H chain in the v8.1 fragment was 30 amino acids in terms of the length from the cysteine at the C-terminus of the L chain to the glutamic acid at the N-terminus of the H chain. For each structure, the template DNAs were mixed at a TT/HH ratio of 100, and Fab-HH xhoI was selected by the Fab-PRD by solid-phase selection described in Example 9. Using the obtained reverse transcription products as samples, the recoveries of Fab-HH and Fab-TT were measured by quantitative PCR to determine the c enrichment ratio (the recovery of Fab-HH/the recovery of Fab-TT). As detection primers to be used for the quantitative PCR, the downstream primers in the vicinity of CDR-H3 were used. The result is shown in FIG. 21. Since a practical enrichment ratio was observed either in the case where the linker between the H chain and SecM was minimized or in the case where the linker between the L chain and the H chain was minimized, it is considered that the linker length can be flexibly selected depending on the situation.

The primers used for the quantitative PCR were as follows.

```
Downstream primers for FabHH
HH-4F:
                                      (SEQ ID NO: 35)
ccagggaactttggttactgtttc Model-4R:
                                      (SEQ ID NO: 36)
ctttaaccagacaacccagtgc Downstream primers for Fab-TT
TT-5F:
                                      (SEQ ID NO: 49)
gcaccctggttaccgtgag Model-4R:
                                      (SEQ ID NO: 36)
ctttaaccagacaacccagtgc
```

The sequences of the linker portions in the v7 and v8.1 DNA fragments used in the Fab-PRD are shown in SEQ ID NOs:50 and 52, respectively.

[Example 14] Study of Minimum Required Copy Number in Monocistronic Fab-PRD

The v7 fragments of Fab-HH xhoI and Fab-TT (Example 13) were prepared as template DNAs and used for preparation of a 10-fold dilution series of the Fab-TT template DNA in a carrier solution containing 0.125 mg/ml yeast RNA and $7\times10^9$ molecules/µl of the Fab-HH template DNA. DNA samples containing $1\times10^6$ molecules/µl to $1\times10^{-5}$ molecules/µl of the Fab-TT template DNA were subjected to amplification by single-molecule PCR using Fab-TT-specific primers, and the PCR products were separated by 5-20% gradient PAGE. It was confirmed that a Fab-TT-specific band is detected in PCR with samples containing 1 or more Fab-TT molecules as the template DNA while the Fab-TT-specific band is not detected in PCR with samples containing 0.1 or less Fab-TT molecule.

From a diluted sample of the Fab-TT template DNA whose quality was confirmed by the single-molecule PCR, an aliquot corresponding to 400 molecules was collected, and the collected sample was added to $1\times10^{12}$ molecules of the Fab-HH template DNA. RNA was synthesized from this, to provide RNA before selection. The RNA was subjected to the Fab-PRD, and recovery of the Fab-TT in an amount corresponding to 400 molecules was attempted. The translation reaction was carried out at a scale of 20 µl at 30° C. for 40 minutes, and, thereafter, an equal volume of WBTBR buffer (50 mM Tris-HCl (pH=7.6), 90 mM NaCl, 50 mM Mg(OAc)$_2$, 5 mg/ml BSA, 1.25 mg/ml yeast RNA, 0.5% Tween 20, 0.04 U/µl RNase Inhibitor) supplemented with 1 µM biotinylated TNFαR was mixed therewith, followed by incubation at 4° C. overnight. To this mixture, an M-280 streptavidin magnetic bead pellet in an amount corresponding to 25 µl was added, and the Fab-TT was recovered. RNA eluted from the M-280 beads with DTT was provided as RNA after selection. Each of the RNAs before and after selection by Fab-PRD was reverse transcribed, and RT-PCR was performed to amplify a Fab-TT fragment (lanes 1 and 2 in FIG. 22) with Fab-TT-specific primers in the vicinity of CDR-H3, and a core fragment containing important genetic information corresponding to the region from CDR-L1 to CDR-H3 (lanes 4 and 5 in FIG. 22) with primers that recognize DNA sequences which are common between Fab-HH and Fab-TT. The band for the core DNA fragment was recovered from 5-20% gradient gel, and reamplified by 2nd PCR (lanes 7 and 8 in FIG. 22).

Using the core DNA fragment obtained by 2nd PCR, PCR was performed using the Fab-TT-specific primers to amplify the Fab-TT fragment. As a result, the Fab-TT fragment was detected not only from the sample before selection but also from the sample after selection, so that it was considered that recovery of the core fragment from the 400 molecules of Fab-TT was successful. Subsequently, for confirmation of the fact that the recovery was specific, the enrichment ratio of Fab-TT was measured by quantitative PCR. The Fab-TT fragment and the core fragment were independently quantified, and the enrichment ratio (the relative amount of Fab-TT in the sample after selection/the relative amount of Fab-TT in the sample before selection) was calculated. As a result, it was found that the content of Fab-TT was 582 times higher in the core DNA fragment after selection (lane 7 in FIG. 22) than in the core DNA fragment before selection (lane 8 in FIG. 22) (enrichment ratio=582). From these results, it was suggested that a target-binding clone contained in the library can be specifically recovered by Fab-PRD in cases where at least 400 molecules of the clone are contained. This rate of recovery is considered to be comparable to those of phage display systems.

The primers used were as follows.

```
Fab-TT-specific primers
T1P-F:
                                          (SEQ ID NO: 54)
gttttactattgaacgttatgcgatgggt T1P-R:
                                          (SEQ ID NO: 55)
cgtagtacataccgttcgggtagttag
```

Primers for amplification of the core region which is common between Fab-HH and Fab-TT

```
Core-1F:
                                          (SEQ ID NO: 56)
gcgcaagcgttggtgatc Core-1R:
                                          (SEQ ID NO: 57)
gctcggacctttggtgcttg
```

[Example 15] Construction of Ymacs-Primary Library (First Half of First Step of Affinity Maturation)

As an example of application the Fab-PRD, affinity maturation of Fab-TT, which is one of the model Fabs, was attempted. On the antigen-antibody binding interface, there are not less than 100 van der Waals forces, and several hydrogen bonds and salt bridges. In order to realize overall optimization of the network of these interactions, a fundamental 2-step strategy called Ymacs was employed, wherein mutations in CDRs which are considered to be beneficial for increasing the affinity are searched in the first step, and the optimal combination of these mutations is searched in the second step.

As an operation of the first half of the first step, a library (Ymacs-primary library) for matrix scanning of the CDR positions corresponding to 50 amino acids was constructed such that every single amino acid among the total of 50 amino acids constituting the CDRs of Fab-TT was randomized into 20 types of amino acids.

First, in order to substitute each of the total of 50 amino acids constituting the CDRs of Fab-TT with the NNK codon, a total of 50 types of forward primers for introduction of single amino acid substitutions were synthesized. These forward primers for introduction of single amino acid substitutions were designed such that a 15-bp annealing region is placed upstream of the NNK codon, and a 12-bp annealing region is placed downstream of the NNK codon. As examples, the primers corresponding to the most upstream site and the most downstream site among the 50 sites where the single amino acid substitutions were introduced are shown below.

FabTT Ymacs-1 L1-1: tgtcgtgcaagccagNNKattaaaaattat (SEQ ID NO:58) (the primer for introduction of a single amino acid substitution at the first amino acid in CDR1 in the L chain)

FabTT Ymacs-1 H3-12: atgtactacgttatgNNKtattggggtcag (SEQ ID NO:59) (the primer for introduction of a single amino acid substitution at the 12th amino acid in CDR3 in the H chain)

By performing PCR using pGAv6.5-Fab-TT as a template and each of the above-described 50 types of forward primers for introduction of single amino acid substitutions in combination with the PURE-3R primer, 50 types of mutated downstream DNA fragments were individually synthesized. The PCR products were separated with 1% agarose gel, and stained with ethidium bromide to confirm their bands. Subsequently, a common constant-sequence upstream DNA fragment was synthesized by PCR, for use as a template in the reaction to extend the reverse strand of the mutated downstream DNA fragment in the upstream direction to provide a full-length DNA. The constant-sequence upstream DNA fragment was synthesized by PCR using PURE-rt-1F and H3checkR Not TA6 as primers such that the fragment has a misanneal region in the 3'-end side in order to avoid production of the full-length DNA from its own forward strand. The PCR product was separated with 1% agarose gel, and stained with ethidium bromide for confirmation of its band.

```
PURE-rt-1F:
                                          (SEQ ID NO: 60)
caatttcggtaatacgactcactatagggagaatttaggtgacactat agaagtg H3checkR Not TA6:
                                          (SEQ ID NO: 61)
tatatatatagcggccgcagaactgccggaaaggtatg
```

A summary of synthesis of the single-position/single-amino acid substitution library is shown in FIG. 23. Two cases of the synthesis wherein the site into which the amino acid substitution was introduced is located most upstream and most downstream are shown. After mixing the constant-sequence upstream DNA fragment (A and B in the figure) and the mutated downstream DNA fragment (C and D in the figure) together, asymmetric PCR was carried out in the presence of the PURE-rt-1F primer (E in the figure). By this, the C strand as the reverse strand of the mutated downstream DNA fragment is extended in the upstream direction to produce a full-length DNA, and the full-length C strand is converted into a double strand by PURE-rt-1F. By mixing 4 µl of each mutated downstream DNA fragment with 0.6 µl of the constant-sequence upstream DNA fragment and performing asymmetric PCR at a scale of 50 µl, 50 types of single-position/single-amino acid substitution libraries were synthesized. The obtained PCR product was separated with 1% agarose gel, and stained with ethidium bromide for confirmation of its band.

The single-position/single-amino acid substitution libraries were divided into the L chain group and the H chain group, and equal volumes of the libraries in each group were mixed together, to provide the L-chain Ymacs-primary library and the H-chain Ymacs-primary library. As shown in FIG. 24, the L-chain Ymacs-primary library is constituted by 19 types of, and the H-chain Ymacs-primary library is constituted by 31 types of, single-position/single-amino acid substitution libraries.

[Example 16] Selection and Next-Generation Sequence Analysis of Ymacs-Primary Libraries (Latter Half of First Step of Affinity Maturation)

As an operation of the latter half of the first step, the Ymacs-primary libraries of the L chain and the H chain were independently selected by Fab-PRD, and the result of next-generation sequence analysis of the obtained DNA samples was used to identify mutations in CDRs which are considered to be beneficial for affinity improvement.

In the selection of the Ymacs-primary libraries by Fab-PRD, the solid-phase selection described in Example 9 and the liquid-phase selection described in Example 14 were used in combination. In round 1, solid-phase selection was carried out, and, in round 2, solid-phase selection was carried out followed by a long period (13 h) of washing. In the final round, round 3, liquid-phase selection was carried out at a bait concentration of 1 nM. In every round, $1 \times 10^{12}$ molecules of RNA were translated at a scale of 20 µl. In the reverse transcription-PCR, the core DNA fragment described in Example 14 was recovered. To the core DNA fragment, an appropriate upstream fragment and downstream fragment were added, and overlapping extension-PCR was performed using PURE-rt-1F and PURE-3R as primers to synthesize the full-length DNA fragment, which was then purified and used as the template DNA in the following round.

The nucleotide sequences of the CDR 1-3 regions in each of the L chain and the H chain in the core DNA fragment obtained in round 3 were analyzed with a Roche GS FLX next-generation sequencer, and 1812 reads of the L-chain CDR 1-3 sequences in the sample derived from the L-chain library and 2288 reads of the H-chain CDR 1-3 sequences in the sample derived from the H-chain library were collected as nucleotide sequence data. From these data, 468 reads from the L chain and 1293 reads from the H chain having a continuous ORF in the CDR1-3 regions were selected as effective reads, and mutations at the CDR positions for a total of 50 amino acids, that is, 19 amino acids in the L chain and 31 amino acids in the H chain constituting the CDRs, were summarized. The number of times each mutation was counted was summarized in the matrix table shown in FIG. 25, wherein the 20 types of amino acids are arranged in the longitudinal direction and the total of 50 CDR positions are arranged in the horizontal direction. Mutations with a large number of counts, except for the parent amino acid at each CDR position, were determined to be potentially beneficial mutations.

[Example 17] Construction of Ymacs-Secondary Library (First Half of Second Step of Affinity Maturation)

As an operation of the first half of the second step, a Ymacs-secondary library was constructed by combining the beneficial mutations identified in Example 16. As the beneficial mutations, a total of 21 mutations at a total of 12 CDR positions were employed, and mixed-base codons were determined such that each of these can encode the parent amino acid and the beneficial mutant amino acid(s) at the respective CDR positions. Some of the mixed-base codons may introduce an unintended amino acid other than the parent amino acid and the beneficial mutant amino acids. The employed beneficial mutations and the mixed-base codons are summarized in FIG. 26. The theoretical diversity of the Ymacs-secondary library was $1.9 \times 10^7$ based on the nucleic acid-level estimation, and $4.9 \times 10^6$ based on the protein-level estimation. Since the 12 CDR positions were dispersed among all 6 CDRs, one mutation-introducing forward primer for each CDR, that is, a total of 6 mutation-introducing forward primers, were synthesized. Using these, a total of 6 mutated DNA fragments, that is, the fragment 2 to fragment 7 shown in FIG. 27, were synthesized. A total of 7 mutated DNA fragments which include these 6 fragments and the fragment 1 were linked together by overlapping extension reaction to prepare a full-length DNA, which was then amplified by PCR reaction. After purification of the obtained PCR product, occurrence of randomization as designed with the mixed bases at the sites of introduction of mutations was confirmed, to provide a Ymacs-secondary library.

The following are the mutation-introducing forward primers.

FabTT Ymacs-2 L1-Fwd:
(SEQ ID NO: 62)
tgtcgtgcaagccaggatattaaaaattatttgWCTtggtatcaacaa
caa
(L-chain CDR1)

FabTT Ymacs-2 L2-Fwd:
(SEQ ID NO: 63)
gccccgaagccactgatttatGSTggttctaaccgccaatctggagtt
cct
(L-chain CDR2)

FabTT Ymacs-2 L3-Fwd:
(SEQ ID NO: 64)
acctattattgccaacaaactKMTRNMtaccctatcacctttggccag
(L-chain CDR3)

FabTT Ymacs-2 H1-Fwd:
(SEQ ID NO: 65)
agctgtgcagcaagcggttttASAattGRGcgttatgcgatgRSTtgg
gtgcgtcaggct
(H-chain CDR1)

FabTT Ymacs-2 H2-Fwd:
(SEQ ID NO: 66)
ggcctggaatgggttggtacgatttatcctKDSRSCgattatRBYgat
tatgccgatagc -continued (H-chain CDR2)

FabTT Ymacs-2 H3-Fwd:
(SEQ ID NO: 67)
tactactgcgctcgctctaactacccgaacggtMTGKRCtacgttat ggaatat
(H-chain CDR3)

[Example 18] Selection of Ymacs-Secondary Library and Analysis of Affinity of Clones (Latter Half of Second Step of Affinity Maturation)

As an operation of the latter half of the second step, the Ymacs-secondary library was selected by Fab-PRD, and the obtained DNAs were cloned into a secretory expression vector for *E. coli*. High-affinity clones were selected by ELISA and SPR (ProteOn XPR36, BioRad), and 2 representative clones of Fab-TT mutants (Ymacs #10 and #19 in FIGS. 29 to 32) were subjected to measurement of KD using KinExA (KinExA 3200, Sapidyne).

Selection of the Ymacs-secondary library by Fab-PRD was carried out by a total of 5 rounds of selection, in each of which liquid-phase selection was performed. The operation proceeded from round 1 to 5 while the bait concentration was gradually decreased from 100 nM to 60 nM, 20 nM, 1 nM, 100 pM and then 10 pM, to increase the selection pressure. The core DNA fragment recovered in round 5 was cloned such that the core region of Fab-HH in a monocistronic scFab-HH expression vector was replaced by the fragment (FIG. 28). Using the culture supernatants of 48 clones randomly picked up, ELISA was carried out with TNFαR as an antigen. After confirming that the hit rate in ELISA was about 50%, the remaining several hundred colonies were recovered at once in the polyclonal state, and their plasmids were purified. The GS linker region between the L chain and the H chain of the scFab-TT mutant encoded by each plasmid was replaced by an untranslated sequence-secretion signal fragment for bicistronic expression, to convert the expression mode from the monocistronic type to the bicistronic type (FIG. 28). By this operation, a vector that expresses the Fab-TT mutant as a naturally-occurring Fab rather than scFab was constructed, and cloning was carried out again. Using the culture supernatants of 96 clones randomly picked up, ELISA was carried out with TNFαR as an antigen. The ELISA hit clones were subjected to determination of the sequences of their CDRs (FIG. 29). The ELISA hit clones were subjected to screening by SPR with a binding time of 1 minute and a dissociation time of 30 minutes, to select high-affinity clones using Koff as an index (FIG. 30). As a result of an attempt to measure the affinities of the parent Fab Fab-TT and an affinity-improved mutant Ymacs #10 by SPR, KD was determined as follows: Fag-TT, KD=7.28×10$^{-9}$; Ymacs #10, KD<1.57×10$^{-11}$. Thus, an about 460-fold increase in the affinity was observed (FIG. 31). Subsequently, as a result of an attempt to measure the affinities of 2 clones, Ymacs#10 and Ymacs #19, having highly improved affinities by KinExA, KD was determined as follows: Ymacs #10, KD=1.87×10$^{-11}$; Ymacs #19, KD=3.45×10$^{-12}$. Thus an about 2100-fold increase in the affinity was observed for Ymacs #19 (FIG. 32).

The experiment for measurement of KD of Ymacs #19 by KinExA was carried out at 2 different Fab concentrations, 35 pM and 350 pM. In terms of the concentration of TNFαR as an antigen, a 2-fold dilution series from 2 nM to 976 fM was prepared for 35 pM Fab, and a 2-fold dilution series from 5 nM to 2.44 pM was prepared for 350 pM Fab. Each sample was incubated at room temperature for 48 hours until the antigen-antibody reaction reaches equilibrium, and the fraction of free Fab after reaching the equilibrium was quantified by KinExA using azlactone beads on which TNFαR was immobilized. The fraction of free Fab (ordinate) was plotted against the antigen concentration (abscissa), to draw 2 dose-response curves corresponding to the different concentrations of Fab. The curves were subjected to global fitting analysis by KinExA Pro Software, to calculate KD.

[Example 19] Selection of Fabs by CIS Display (Fab-CIS)

By reference to a report by Odegrip et al. (Odegrip et al., Proc Natl Acad Sci USA. (2004) vol. 101, p. 2806-2810), selection of Fabs by CIS display was attempted. As shown in FIG. 8, overlapping extension-PCR was performed to add a promoter sequence for *E. coli* RNA polymerase and the RepA-CIS-ori sequence in the upstream region and the downstream region, respectively, of the scFab-coding region in the v7 fragment, to provide the v10.1 fragment. Since the RepA-coding sequence was different between the sequence reported by Odegrip et al. and the sequence of GenBank V00351, the sequence of V00351 was employed. A mixture wherein v10.1 fragments of Fab-HH xhoI and Fab-TT were mixed at a TT/HH ratio of 10 was used as a template DNA for in vitro transcription/translation reaction. Purified template DNA (1.2 μg) was subjected to an *E. coli*-derived S30-based transcription/translation system (25 μL, derived from the *E. coli* SL119 strain, for linear DNA, L1030, Promega), to synthesize the display molecule complex at 30° C. for 40 minutes. Thereafter, by reference to the report by Odegrip et al., Fab-HH was recovered by liquid-phase selection in the same manner as in Example 14, and PCR was carried out by using the eluted DNA as a template and Cis-1F and Cis-6R as primers, to amplify the full-length fragment. By the same evaluation system as in Example 10 using the sensitivity to XhoI as an index, the performance of the Fab-HH selection system by CIS display was checked. The result is shown in FIG. 33. When the selection was carried out without addition of biotinylated Her-2, no increase in the sensitivity to XhoI was observed relative to the DNA sample before selection. On the other hand, when the selection was carried out by addition of biotinylated Her-2, an increase in the sensitivity to XhoI could be observed. From these results, it can be seen that Fab-HH was specifically enriched.

Further, a mixture wherein v10.1 fragments of Fab-HH xhoI and Fab-TT were mixed at a TT/HH ratio of 100 was used to perform the same experiment, to study the optimal transcription/translation time. The result is shown in FIG. 34. With every transcription/translation time studied, specific enrichment of Fab-HH could be observed. With a transcription/translation time of 10 minutes, the enrichment ratio was insufficient. However, the enrichment ratio sufficiently increased with 20 minutes to 40 minutes of the transcription/translation, and the ratio tended to gradually decrease after 80 minutes to 120 minutes of the transcription/translation. From these results, the optimal transcription/translation time was considered to be 20 minutes to 40 minutes.

The sequences of the primers for amplification of the full-length v10.1 fragment were as follows.

INDUSTRIAL APPLICABILITY

Cis-1F
(SEQ ID NO: 68)
cagttgatcggcgcgagatttaatcgccgc

Cis-6R
(SEQ ID NO: 69)
cgtaagccggtactgattgatagatttcaccttacccatc

The present invention is useful in the fields of genetic engineering, protein engineering and the like. Fabs obtained by the method of the present invention are useful in the fields of diagnosis, medical care, research and the like.

---

The invention claimed is:

1. A polynucleotide construct comprising a Fab first chain-coding sequence and a Fab second chain-coding sequence, wherein said polynucleotide construct expresses a Fab encoded by itself without dissociation, and maintains a complex with the Fab, when it is introduced into a cell-free translation system containing ribosomes.

2. The polynucleotide construct according to claim 1, wherein said polynucleotide construct monocistronically comprises a ribosome-binding sequence, Fab first chain-coding sequence, linker peptide-coding sequence, Fab second chain-coding sequence and scaffold-coding sequence in this order, and further comprises at its 3'-end a structure necessary for maintaining a complex with the Fab encoded by itself.

3. The polynucleotide construct according to claim 1, wherein said polynucleotide construct comprises a Fab first chain-expressing cistron and a Fab second chain-expressing cistron each containing a ribosome-binding sequence, a Fab first chain-coding sequence or Fab second chain-coding sequence, and a scaffold-coding sequence in this order, said first Fab-expressing cistron further comprising at its 3'-end a ribosome stall sequence, said Fab second chain-expressing cistron further comprising at its 3'-end a structure necessary for maintaining a complex with the Fab encoded by itself.

4. The polynucleotide construct according to claim 2, wherein said structure necessary for maintaining a complex with the Fab encoded by itself is a ribosome stall sequence, puromycin or a derivative thereof, or a DNA-binding protein-coding sequence and a binding sequence for said DNA-binding protein.

5. The polynucleotide construct according to claim 4, wherein said structure necessary for maintaining a complex with the Fab encoded by itself is a ribosome stall sequence.

6. The polynucleotide construct according to claim 5, wherein said ribosome stall sequence is a SecM sequence, diproline sequence, or both of them.

7. The polynucleotide construct according to claim 5, wherein said ribosome stall sequence is composed of 2 to 4 repeats of the SecM sequence.

8. The polynucleotide construct according to claim 4, wherein a stop codon is present in the 3'-side of said ribosome stall sequence.

9. The polynucleotide construct according to claim 4, wherein said structure necessary for maintaining a complex with the Fab encoded by itself is puromycin or a derivative thereof.

10. The polynucleotide construct according to claim 4, wherein said structure necessary for maintaining a complex with the Fab encoded by itself is a DNA-binding protein-coding sequence and a binding sequence for said DNA-binding protein.

11. The polynucleotide construct according to claim 10, wherein said DNA-binding protein is a cis-binding protein which is never dissociated during transcription/translation reaction from the DNA molecule used as a template for said transcription/translation and which binds to said binding sequence for the DNA-binding protein located in the same DNA molecule.

12. The polynucleotide construct according to claim 10, wherein said DNA-binding protein is RepA encoded by *Escherichia coli* R1 plasmid and said binding sequence for the DNA-binding protein is a CIS-ori sequence located downstream of the RepA-coding sequence in the same polynucleotide.

13. The polynucleotide construct according to claim 1, wherein said polynucleotide construct is a library wherein said Fab first chain-coding sequence and said Fab second chain-coding sequence comprise random sequences.

14. The polynucleotide construct according to claim 13, wherein said library comprising random sequences is a (i) naive library or (ii) focused library.

15. The polynucleotide construct according to claim 13, wherein said library comprising random sequences is a library comprising single amino acid substitutions in the complementarity-determining region(s) (CDR(s)) of the Fab first chain and/or the Fab second chain.

16. A method for screening a Fab, said method comprising the steps of:
(i) introducing the polynucleotide construct according to claim 1 into a cell-free translation system to synthesize Fabs, and displaying said synthesized Fabs on the polynucleotides encoding said Fabs;
(ii) bringing said Fabs displayed on said polynucleotides into contact with an antigen;
(iii) selecting a Fab of interest that reacts with said antigen; and
(iv) amplifying the polynucleotide encoding said Fab of interest.

17. The method for screening a Fab according to claim 16, said method comprising the steps of:
(I) providing a plurality of types of the polynucleotide construct according to claim 15, in each of which the Fab first chain-coding sequence or the Fab second chain-coding sequence encodes an amino acid sequence comprising a single amino acid substitution at a single position in a CDR in the amino acid sequence of the Fab first chain or the Fab second chain of the parent antibody, such that single amino acid substitutions are contained for a plurality of positions in the CDRs of the Fab first chain and the Fab second chain;
(II) carrying out first screening wherein said steps (i) to (iv) are repeated using said plurality of types of the polynucleotide construct, to screen a plurality of high-affinity Fabs;
(III) analyzing single amino acid substitutions at respective positions in the CDRs of the Fab first chain and the Fab second chain in said plurality of Fabs selected in said first screening step;
(IV) providing the polynucleotide construct according to claim 15 wherein the Fab first chain-coding sequence and the Fab second chain-coding sequence encode amino acid sequences comprising combinations of the single amino acid substitutions identified in said first screening at said respective positions in the CDRs of the Fab first chain and Fab second chain sequences of the parent antibody; and
(V) carrying out second screening wherein said steps (i) to (iv) are repeated using said polynucleotide construct, to screen a high-affinity Fab.

18. The method according to claim 16, wherein said in vitro translation system is composed of factors independently purified.

19. The method according to claim 18, wherein said in vitro translation system contains at least one component selected from the group consisting of initiation factors, elongation factors, aminoacyl-tRNA synthetase and methionyl-tRNA transformylase.

20. The method according to claim 18, wherein said in vitro translation system does not contain a releasing factor.

21. The method according to claim 16, wherein said in vitro translation system is a cell extract containing ribosomes.

22. A method for producing a Fab, said method comprising the step of introducing the polynucleotide construct according to claim 1 into an in vitro translation system to produce a Fab.

23. A kit for producing or screening a Fab, said kit comprising the polynucleotide construct according to claim 1.

* * * * *